United States Patent [19]
Vitetta et al.

[11] Patent Number: 5,767,072
[45] Date of Patent: Jun. 16, 1998

[54] THERAPEUTIC COMPOSITIONS COMPRISING A CD4 PEPTIDE AND METHODS OF TREATMENT OF HIV INFECTIONS

[75] Inventors: Ellen S. Vitetta; Jonathan W. Uhr, both of Dallas, Tex.

[73] Assignee: Board of Regents, The University of Texas System, Austin, Tex.

[21] Appl. No.: 171,206

[22] Filed: Dec. 21, 1993

Related U.S. Application Data

[63] Continuation of Ser. No. 792,212, Nov. 13, 1991, abandoned, which is a continuation-in-part of Ser. No. 519,240, May 3, 1990, abandoned, which is a continuation of Ser. No. 407,479, Sep. 14, 1989, abandoned.

[51] Int. Cl.$^6$ .................. A61K 38/10; A61K 38/16
[52] U.S. Cl. .................. 514/12; 424/185.1; 424/193.1; 424/194.1; 514/8; 514/13; 530/391.7; 530/391.9; 530/402
[58] Field of Search .................. 530/350, 363, 530/367, 395, 402, 408, 409, 391.7, 391.9; 514/2, 8, 12, 13; 424/85, 91, 185.1, 193.1, 194.1

[56] References Cited

U.S. PATENT DOCUMENTS

| | | | |
|---|---|---|---|
| 4,935,465 | 6/1990 | Garman et al. | 525/54.1 |
| 5,116,944 | 5/1992 | Sivam et al. | 530/362 |
| 5,206,353 | 4/1993 | Berger et al. | 536/23.4 |

FOREIGN PATENT DOCUMENTS

| | | |
|---|---|---|
| 0 314 317 A1 | 5/1989 | European Pat. Off. |
| WO87/02987 | 5/1987 | WIPO |
| WO89/02922 | 4/1989 | WIPO |

OTHER PUBLICATIONS

Schniffman et al. (1988) J. Immunol. 141, 4181–4186.
Ghetie et al. (1991) Proc. Natl. Acad. Sci. 88, 5690–5693.
"HIV-Infected Cells Are Killed by rCD4-Ricin A Chain", *Science,* Nov. 25, 1988, vol. 242, pp. 1166–1168.
"Studies are Exploring Potential of Soluble CD4 Therapy for HIV", *Exchange,* published by NIAID, May/Jun., 1989, pp. 5–9.

*Primary Examiner*—Keith C. Furman
*Attorney, Agent, or Firm*—Arnold, White & Durkee

[57] ABSTRACT

Disclosed are methods and compositions for the treatment of HIV infections through the specific elimination of cells which express HIV env determinants such as gp120. The compositions of the invention include toxin conjugates composed of a CD4 derived gp120 binding ligand conjugated to a toxin A chain moiety such as ricin A chain or deglycosylated ricin A chain. Where a therapeutic composition is desired, the conjugates are formed by means of a cross linker which includes a disulfide bond. Disulfide linkages are not crucial where non-therapeutic uses, such as antibody generation, is intended. In preferred aspects of the invention, conjugates incorporating shorter CD4 peptides, such as those incorporating amino acids 41–57 or 41–84 of CD4, are disclosed. Therapeutic amounts of conjugates composed of soluble CD4 or a CD4 peptide cross-linked to deglycosylated A chain by means of as SMPT linker is administered to an HIV infected patient so as to specifically eliminate HIV infected cells without exerting significant toxicity against uninfected or class II cells.

17 Claims, 18 Drawing Sheets

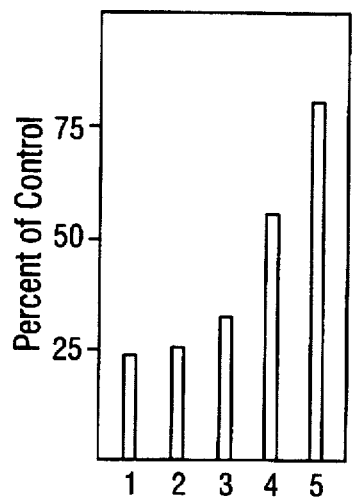 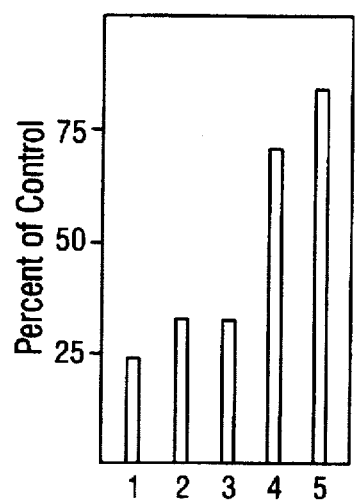 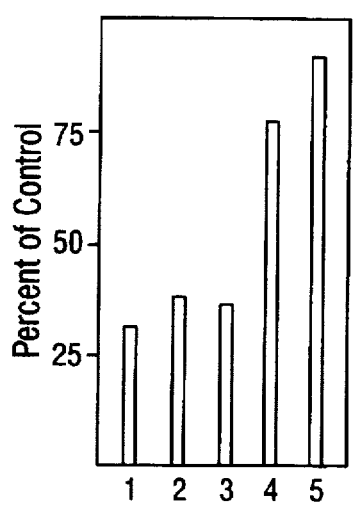
FIG. 4A  FIG. 4B  FIG. 4C
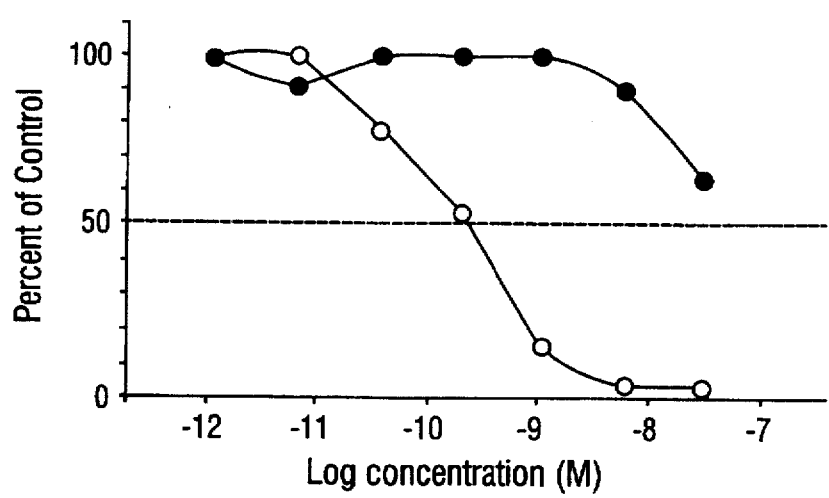
FIG. 5

1   ASN-LYS-VAL-VAL-LEU-GLY-LYS-LYS-GLY-ASP-THR-VAL-GLU-LEU-THR-CYS-THR-ALA-SER-GLN 20
21  LYS-LYS-SER-ILE-GLN-PHE-HIS-TRP-LYS-ASN-SER-ASN-GLN-ILE-LYS-ILE-LEU-GLY-ASN-GLN 40
41  GLY-SER-PHE-LEU-THR-LYS-GLY-PRO-SER-LYS-LEU-ASN-ASP-ARG-ALA-ASP-SER-ARG-ARG-SER 60
61  LEU-TRP-ASN-GLN-GLY-ASN-PHE-PRO-LEU-ILE-ILE-LYS-ASN-LEU-LYS-ILE-GLU-ASP-SER-ASP 80
81  THR-TYR-ILE-CYS-GLU-VAL-GLU-ASP-GLN-LYS-GLU-GLU-VAL-GLN-LEU-LEU-VAL-PHE-GLY-LEU 100

FIGURE 13

```
  1                                                    10                                    20
ILE-PHE-PRO-LYS-GLN-TYR-PRO-ILE-ILE-ASN-PHE-THR-THR-ALA-GLY-ALA-THR-VAL-GLN-SER 21                                                    30                                    40
TYR-THR-ASN-PHE-LEU-ARG-ALA-VAL-ARG-GLY-ARG-LEU-THR-THR-GLY-ALA-ASP-VAL-ARG-HIS 41                                                    50                                    60
GLU-ILE-PRO-VAL-LEU-PRO-ASN-ARG-VAL-GLY-LEU-PRO-ILE-ASN-GLN-ARG-PHE-ILE-LEU-VAL

------------------------------------------------------------------------------------

140                                                   150                                   160
GLY-ASN-GLY-PRO-LEU-GLU-GLU-ALA-ILE-SER-ALA-LEU-TYR-TYR-TYR-SER-THR-GLY-GLY-THR-GLN 161                                                   170                                   181
LEU-PRO-THR-LEU-ALA-ARG-SER-PHE-ILE-ILE-CYS-ILE-GLN-MET-ILE-SER-GLU-ALA-ALA-ARG-PHE 182                                                   190                                   202
GLN-TYR-ILE-GLU-GLY-GLU-MET-ARG-ILE-ILE-ARG-THR-ARG-ILE-ARG-TYR-ASN-ARG-SER-ALA-PRO-ASP-PRO

------------------------------------------------------------------------------------

246                                                   255                                   265
ILE-LEU-LEU-PRO-ILE-ILE——ALA-MET-VAL-TYR-ARG-CYS-ALA-PRO-PRO-PRO-SER-SER-GLN-PHE
```

FIGURE 16

THERAPEUTIC COMPOSITIONS COMPRISING A CD4 PEPTIDE AND METHODS OF TREATMENT OF HIV INFECTIONS

This application is a continuation, of application Ser. No. 07/792,212, filed Nov. 13, 1991, now abandoned, which is a continuation-in-part of U.S. Ser. No. 07/519,240, filed May 3, 1990, now abandoned, which is a continuation of U.S. Ser. No. 07/407,479, filed Sep. 14, 1989, now abandoned.

The government may own certain rights in the present invention pursuant to NIH grants CA-28149, CA-41081, CA-09082, and RR-00890.

BACKGROUND OF THE INVENTION

1. Field of the Invention

The present invention relates to methods and compositions for the treatment of HIV infections. In particular, the invention relates to the targeting of cytotoxic reagents to HIV-infected cells through the use of toxin-conjugated ligands capable of specific recognition of such cells, as well as associated technology directed to the preparation of such toxin-conjugated ligands.

2. Description of the Related Art

Acquired immunodeficiency syndrome (AIDS) is caused by a retrovirus identified as human immunodeficiency virus (HIV) (1–6). Most individuals infected with HIV go on to develop AIDS (7), which is characterized by the progressive depletion of those cells expressing a cellular receptor for the HIV retrovirus (8). A number of immunologic abnormalities have been described in AIDS including abnormalities in B-cell function, abnormal antibody response, defective monocyte cell function, impaired cytokine production (9–12), depressed natural killer and cytotoxic cell function (13), and defective ability of lymphocytes to recognize and respond to soluble antigens (14). Other immunologic abnormalities associated with AIDS have been reported (15,16). Among the more important immunologic defects in patients with AIDS is the depletion of the T4 (CD4) helper/inducer lymphocyte population (1,2,11,12).

In spite of the profound immunodeficiency observed in AIDS, the mechanism(s) responsible are not clearly understood. Several postulates exist. One view is that defects in immune responsiveness are due to selective infection of helper T cells by HIV, resulting in impairment of helper T cell function and eventual depletion of cells necessary for a normal immune response (1–6,17). Recently, in vitro and in vivo studies showed that HIV can also infect monocytes which are known to play an essential role as accessory cells in the immune response (18,19). HIV may also lead to immunodeficiency by interfering with normal cytokine production in an infected cell resulting in secondary immunodeficiency as for example, IL-1 and IL-2 deficiency (20). None of these models resolves the question of whether a component of HIV per se, rather than infection by replicative virus, is responsible for the immunologic abnormalities associated with AIDS.

The primary immunologic abnormality resulting from infection by HIV is the progressive depletion and functional impairment of T lymphocytes expressing the CD4 cell surface glycoprotein (29). CD4 is a non-polymorphic glycoprotein with homology to the immunoglobulin super gene superfamily (30). Together with the CD8 surface antigen, CD4 defines two distinct subsets of mature peripheral T cells (31), which are distinguished by their ability to interact with nominal antigen targets in the context of class I and class II major histocompatibliity complex (MHC) antigens, respectively (32–36). For the most part, CD4+ T-cells display the helper/inducer T cell phenotype (37–39), although CD4+ T-cells characterized as cytotoxic suppressor T cells have been identified. The loss of CD4+ helper inducer T cell function probably underlies the profound defects in cellular and humoral immunity leading to the opportunistic infections and malignancies characteristics of the acquired immunodeficiency syndrome (AIDS) (29).

The possibility that CD4 itself is an essential component of the cellular receptor for "HIV-1" was first indicated by the observation that monoclonal antibodies directed against CD4 block "HIV-1" infection and syncytia induction (40–42). This hypothesis has been confirmed by the demonstration that a molecular complex forms between CD4 and gp120, the major envelope glycoprotein of "HIV-1" (43), and the finding that "HIV-1" tropism can be conferred upon ordinarily non-permissive human cells following the stable expression of a CD4 cDNA (44). Furthermore, the neurotropic properties of "HIV-1", reflected by a high incidence of central nervous system dysfunction in "HIV-1" infected individuals (45), and the ability to detect "HIV-1" in the brain tissue and cerebrospinal fluid of AIDS patients (46–50), appears to have its explanation in the expression of CD4 in cells of neuronal glial and monocyte macrophage origin (51–53).

The known sequence of the CD4 precursor predicts a hydrophobic signal peptide, an extracellular region of approximately 370 amino acids, a highly hydrophobic stretch with significant identity to the membrane-spanning domain of the class II MHC beta chain, and a highly charged intracellular sequence of 40 residues (58). The extracellular domain itself of CD4 is found to consist of four contiguous regions each having amino acid and structural similarity to the variable and joining (V-J) domains of immunoglobulin light chins as well as related regions in other members of the immunoglobulin gene superfamily (a subclass of which have been defined by the coined term "adhesions"). These structurally similar regions of CD4 have been termed the $V_1J_1$, $V_2J_2$, $V_3J_3$ and $V_4J_4$ domains (denominated domains 1–4 in FIG. 3 of reference 23).

The HIV env protein has also been extensively described, and the amino acid and RNA sequences encoding HIV env from a number of HIV strains are known (22). The HIV virion is covered by a membrane or envelope derived from the outer membrane of host cells. The membrane contains a population of envelope glycoproteins (gp160) anchored in the membrane bilayer at their carboxyl terminal region. Each glycoprotein contains two segments. The N-terminal segment, called gp120 by virtue of its relative molecular weight of about 120 kD, protrudes into the aqueous environment surrounding the virion. The C-terminal segment, called gp41, spans the membrane. gp120 and gp41 are covalently linked by a peptide bond that is particularly susceptible to proteolytic cleavage.

At least two kinds of immune system cells are infected by HIV (human immunodeficiency virus), monocytes, and T-lymphocytes. Only those monocytes and T-cells which have the CD4 receptor are thought to be infected by HIV. A conserved region of the HIV viral coat protein (gp160) binds to the CD4 receptor which undergoes internalization and carries the RNA virus into the cell. Once inside the cell the virus makes a DNA copy of its RNA with its enzyme reverse transcriptase. Nucleoside analogues protect cells by serving as chain breakers in the transcription of viral RNA. They are incorporated into the growing polymer but lack the functional group necessary to bind the next nucleoside into the chain, thus the chain is interrupted and therefore nonfunctional.

Current AIDS therapy which is directed towards protecting uninfected cells, consists of oral dosing about every four hours with nucleoside analogues (such as AZT and DDC) which inhibit viral RNA replication. Although these drugs inhibit viral replication at concentrations of 50–500 uM, at higher concentrations (~1 mM) they also inhibit the DNA polymerase of healthy cells which is required for cell division. The current therapy requires very large doses of drugs (up to a gram/day). Because the drugs are taken orally and in a form that is absorbed by all cells, the entire body is exposed to them. Toxicity is a serious limitation to their use; aplasia and anemia being the most severe side effects.

Because nucleoside derivatives must be phosphorylated before they can be incorporated into DNA (and express their chain disrupting activity) they require kinases which are not present in equal amounts in all cells susceptible to viral infection. Thus the oral nucleoside analogue therapy, which is ineffective against already infected cells, is only able to protect those susceptible cells which can convert high concentrations of nucleosides into nucleotides (i.e., dividing cells). For these reasons this therapy is limited and the progression of the disease is only slowed.

Various alternative or additional approaches to the treatment of HIV infections have been studied. One approach, which at one time was thought might prove particularly beneficial, was the use of cell surface adhesions to prevent viral attachment to target cells (23–25). This approach involves the administration of isolated CD4 molecules or variants thereof to AIDS patients in an amount that will theoretically attach to plasma-borne virus particles released from infected cells. By attaching to circulating virus particles it was hoped that the CD4 or variant would serve to prevent viral attachment to target cells, and thus interfere with the infection process.

Another approach to the treatment of HIV infections which has been mentioned involves the application of immunotoxin technology to "target" cells susceptible to HIV infection with a cytotoxic reagent. Immunotoxins are conjugates between an antibody, typically a monoclonal antibody, and a toxin molecule, such as the A chain of the plant toxin, ricin. It has been shown that conjugates of toxins and cell-reactive ligands can specifically delete targeted cells both in vitro and in vivo (26). Such conjugates kill cells after endocytosis of the conjugate-antigen complex and translocation of the A chain into the cytosol where it inhibits protein synthesis (26).

Immunotoxin approaches which have been proposed for the treatment of HIV infections include the use of toxin conjugates of HIV env glycoproteins or other retroviral proteins (27,28). With regard to toxin conjugates of retroviral env proteins, it is proposed that structures such as gp120 or gp41 molecules conjugated with cytotoxic reagents will serve to target the toxin moiety to, and thus kill, those cells that are the most likely to harbor HIV, the CD4⁺ T-cells. In this manner it is hoped that the vicious cycle of infection and viral replication can be broken.

Alternatively, it has been proposed to employ immunotoxins (or immunoconjugates) formed of antibodies having specificity for either env or CD4 proteins. In the former case, anti-HIV activity is predicated on the observation that HIV infected T-cells tend to exhibit retroviral env determinants on their cell surfaces. Thus, it is proposed that such immunotoxins will specifically recognize HIV infected cells by means of their anti-env ligands. In contrast, it is envisioned that anti-CD4-toxin constructs will serve to deliver toxin to all CD4⁺ cells, and thus, like env-toxin conjugates, kill those cells targeted for the infection. While the foregoing immunotoxin approaches hold out some promise in the treatment of AIDS, their efficacy has yet to be proven in the clinic.

Thus, although numerous approaches to the treatment of HIV infections have been attempted or described, there is not as yet a treatment that has shown particular promise in addressing the life threatening aspect of this disease. Accordingly, there continues to be a dramatic need for new and improved anti-HIV treatment and therapy modalities that will improve medical science's ability to address this disease and provide a basis for stopping its spread.

SUMMARY OF THE INVENTION

The present invention addresses one or more deficiencies in the prior art by providing an approach that may prevent or delay the onset of AIDS by eliminating cells which produce viral proteins early in the course of the disease. It is proposed that the methodology disclosed herein will prevent the spread of infection and the release of viral proteins that may participate in the pathogenesis of this disease.

The invention provides, in a general sense, a CD4-related ligand having binding affinity for retroviral env determinants, wherein the binding ligand is conjugated to a toxin molecule such as a toxin A chain or functional equivalent thereof. The retroviral env binding ligand of the present invention is termed a "CD4 gp120 binding ligand". For the purposes of the present invention, a "CD4 gp120 binding ligand" is defined as CD4 or a CD4 derived or variant protein or peptide which is capable of binding to the gp120 env glycoprotein.

A variety of CD4 proteins and peptides are known that will complex with gp120 and will thus serve the purposes of the invention. For example, the "extracellular segment" of the CD4 protein, also referred to as "soluble CD4", is that portion of the molecule that interacts with extracellular substances, and it is this extracellular portion that interacts with HIV env determinants. Thus, the extracellular segment of CD4, env-binding domains and peptides derived therefrom, including peptides incorporating biologically functional equivalent amino acids which serve the same purposes of binding to env domains, and the like, are considered to be "CD4 gp120 binding ligands" for the purposes of the present invention.

The novel constructs of the present invention are employed by administering therapeutic amounts of gp120 binding ligand-toxin conjugates to an individual in need of such therapy, such as an individual infected with HIV. Surprisingly, it has been discovered by the inventors that such constructs serve to selectively kill HIV-infected cells while leaving non-HIV-infected cells relatively intact and unaffected. A further surprising aspect of the invention involves the discovery that by treating HIV-infected cells with such an immunotoxin, the cells do not release viral particles in a manner that leads to further infectivity. This aspect is important because it could not have been predicted a priori that specific targeting of a toxin to HIV-laden cells would have a beneficial effect. That is, one would have predicted that the killing of HIV-infected cells would serve simply to release HIV particles and therefore actually enhance infectivity. The inventors have discovered that this is not the case.

In certain embodiments of the invention, the CD4 gp120 binding ligand will thus comprise a soluble CD4 molecule such as a native CD4 molecule comprising all regions, except for the transmembrane domain. Particular benefit may be realized where one employs so called "soluble" CD4, which is the "extracellular" portion of the native CD4 molecule wherein the hydrophobic leader and transmembrane regions have been removed, for example, by recombinant DNA technology. For particular techniques relating to the recombinant preparation of CD4, including CD4 variants and derivatives, one may wish to refer to references 23–25, incorporated herein by reference.

However, research has shown that approximately one-third of AIDS serum completely blocks soluble CD4 from binding to gp120, about one-third of AIDS serum reduces soluble CD4-gp120 binding, and about one-third of AIDS serum does not effect CD4-gp120 binding. In the present invention, the inventors demonstrate that this blockage or reduction in CD4-gp120 binding is due to anti-gp120 antibodies which are present in most $HIV^+$ sera. A surprising and unexpected finding of the present invention was that, even though anti-gp120 antibodies block the binding of soluble CD4 to gp120, these antibodies did not block the CD4 binding site. This finding was demonstrated in the present invention by showing that CD4-peptides and CD4-peptide conjugates bind gp120 in the presence of $HIV^+$ sera which blocked the binding of soluble CD4.

Therefore, in still further embodiments, rather than using the entire CD4 molecule, or a soluble CD4 variant molecule, one may wish to employ as the gp120 binding ligand a short peptide or portion of a CD4 domain which includes a gp120 binding region. In this regard, it has been found that the first domain of CD4 includes the gp120 binding region within its structure. Thus, for the purpose of the present invention, one may wish to employ a peptide which includes within its structure at least the gp120 binding region of domain 1 of CD4. Domain 1 is typically thought to include amino acids 1 to 100 or 109 of CD4, wherein −25 is the initiating MET residue of the leader (see reference 23, for example). The application of recombinant DNA technology can be employed to prepare suitable CD4 peptides which include at least the domain 1 of CD4 and derivatives therefrom and equivalents. Although domain 1 contains the gp120 binding site, peptides comprising portions of the first two domains of CD4 as a binding ligand may provide advantages.

It will be generally desirable to prepare constructs which incorporate a gp120 binding ligand which does not impart a class II binding activity to the conjugate. Class II sites are found on class II major histocompatibility antigens (MHC) which distinguish cells on their ability to interact immunologically. Hence, cell bound-CD4 binds to cell bound-Class II molecules and allows $CD4^+$ cells to physically interact with Class $II^+$ cells. This is the basis by which $CD4^+$ interact with Class $II^+$ monocytes or B cells. Although soluble CD4 does not appear to bind to class $II^+$ cells in vitro, this could be a problem in vivo. If binding did occur in vivo Class $II^+$ cells would be killed.

Although various regions within the first or "V1" domain of CD4 have been proposed as gp120 binding sites. The exact location or locations within the V1 region has been controversial. Reports have variously placed a gp120 binding site at within amino acids 18–44 (95), 41–57 (96), or 81–92 (68) of CD4. These sites are said to be involved in either syncytia formation and/or direct binding of gp120 to CD4 (97, 98). With regard to peptide 81–92, it is indicated that the Cys at position 84 and the Glu at position 85 should be benzylated for the peptide to inhibit syncytia formation (68). It is further pointed out that the binding ligands that include 41–57, and more preferrably 41–84, are particularly preferred for use in the practice of the present invention.

The present inventors have discovered that peptides incorporating amino acids 41–57 have particular advantages when used as gp120 binding ligands in accordance with the present invention. For example, CD4 peptide (41–84)-OVA and (41–57)-OVA constructs were shown to bind gp120 in the presence of $HIV^+$ sera, which blocked the binding of soluble CD4. Of the peptide-protein conjugates tested, CD4 peptide 41–84 was most effective at binding gp120 in the presence of $HIV^+$ sera.

Therefore, in particular embodiments of the invention, the gp120 binding ligand will be defined as comprising a protein or peptide which includes within its sequence a relatively short stretch of amino acids capable of binding to gp120. One particularly useful sequence for incorporation into peptides for this purpose includes amino acids 41–57 of CD4:

-Gly-Ser-Phe-Leu-Thr-Lys-Gly-Pro-Ser-Lys-Leu-Asn-Asp-Arg-Ala-Asp-Ser-;

or its biological functional equivalent. Another particularly useful sequence for incorporation into peptides for this purpose includes amino acids 41–84 of CD4:

-Gly-Ser-Phe-Leu-Thr-Lys-Gly-Pro-Ser-Lys-Leu-Asn-Asp-Arg-Ala-Asp-Ser-Arg-Arg-Ser-Leu-Trp-Asp-Gln-Gly-Asn-Phe-Pro-Leu-Ile-Ile-Lys-Asn-Leu-Lys-Ile-Glu-Asp-Ser-Asp-Thr-Tyr-Ile-Cys-;

or its biological functional equivalent.

Amino acid sequences such as the foregoing can be employed directly as a short peptide ligand or can be incorporated into a larger peptide or protein structure which nevertheless retains the ability to bind to gp120 binding sites by virtue of the binding region contained within this peptide. For the preparation of such constructs, one may choose to employ recombinant DNA technology or, alternatively, simply prepare the peptidal construct by means of peptide synthesis technology. Peptide synthesis provides particular advantages in terms of ease of preparation and purity, and can be applied to conveniently prepare peptides of 40 to 50, or even 100, amino acids in length.

In further embodiments, multivalent peptide-protein conjugates may be generated, wherein multiple peptides are incorporated per molecule of protein. Particular advantages over free peptide or monovalent peptide-protein conjugates may be obtained by constructing multivalent peptide-protein conjugates. For example, multivalent conjugates increase the number of interactions between CD4 peptides and HIV-infected cells displaying many GP120 molecules, and can result in an increased binding affinity of the conjugate for the infected cell. In particular embodiments, multivalent conjugates will be generated which contain three to five CD4 peptides per molecule of protein. In these embodiments, multivalent constructs, such as conjugates comprised of multivalent CD4 peptides-protein-toxin, may be generated which provide significant advantages in HIV therapy.

It is proposed that it will be advantageous to, in general, prepare relatively small conjugates which carry out the respective functions of binding and toxin delivery. It is believed that the use of such a relatively short binding ligand will prove desirable, and provide potential advantages, including 1) the absence of a class II binding site; 2) decreased antigenicity of the conjugate; 3) better penetration of the conjugate into tissues; 4) a lack of carbohydrate on the peptide as compared with native CD4, which might prevent "liver-homing"; 5) a lower production cost with no need for the use of transfected cells to express the CD4 gene; and 6) the ability to bind gp120 and other viral antigens (e.g., GP41) expressed on HIV-infected cells in vivo, even when anti-gp120 antibodies are present which would block the binding of larger binding ligands, such as soluble CD4 or CD4-ricin A conjugates.

Since CD4-peptide (41–84)-OVA constructs were highly effective at binding to gp120 in the presence of HIV⁺ sera, a most preferred embodiment of the present invention would employ CD4 peptide 41–84 as binding ligand in peptide-protein constructs capable of binding gp120 in the presence of anti-gp120 antibodies.

In more particular embodiments, CD4 peptides which comprise a portion of the CD4 peptide 41–84 sequence may be employed as binding ligands in peptide-protein constructs capable of binding gp120 in the presence of anti-gp120 antibodies. For example, CD4-peptide (41–57)-protein conjugates and others, such as CD4 residues 28–58 (95), 41–55 (96), 44–52 (95), 36–62 (108), 77–85 (108), and 81–92 (68), could be constructed to provide particular benefits in HIV therapy. Exemplary benefits of using small peptides in therapeutic constructs include the ease of synthesizing small peptides and the ability to avoid interference in their activity by HIV antibodies in vivo.

In preferred aspects, one will desire to employ peptide-protein conjugates incorporating a CD4 peptide having from at least about 12 to about 50 amino acids, with peptides of about 40 amino acids in length being preferred. It is proposed that binding ligands of this length will provide particular benefits relative to much larger proteins or peptides in terms of greater biodistribution, decreased metabolic destruction, absence of a class II-binding site, decrease liver homing and thus metabolic destruction, and access to gp120 determinants on HIV virus and HIV-infected cells.

In embodiments wherein relatively short peptides are employed as binding ligands, it is proposed that certain advantages, including higher affinity, better spatial configuration and longer half-life, may be realized through incorporation of a linking spacer region between the peptide and the toxin chain. Exemplary spacer regions include virtually any serum soluble, preferrably autologous protein, particularly proteins such as BSA, HSA, OVA, poly-gly, poly-ala or the like, or even non-protein structures such as bis-imidoesters or N-hydroxysuccinimide esters.

The ligand-toxin conjugate composition of the invention will typically comprise a gp120 binding ligand conjugated to the toxin molecule or spacer region through a disulfide linkage. This is because it has been found that the disulfide linkage is important where one desires to employ ricin A chain in the conjugate in connection with anti-cellular therapy. While the mechanism is not entirely clear, it appears as though a disulfide linkage allows decoupling and subsequent internalization of the ricin A chain moiety delivered to target cells by the binding ligand, thereby freeing the A chain moiety to exert its anti-cellular effect. Of course, where one does not intend to employ such constructs for anti-cellular therapy, for example, where one seeks simply to prepare antibodies against, e.g., rCD4-dgA conjugates, or use rCD4-dgA in a binding assay for, e.g., anti-dgA or anti-CD4 antibodies, the disulfide linkage will not be crucial.

It is proposed that the configuration of cross-linking between ricin A chain and binding function is an important consideration in that this configuration appears to play an important role pharmacologically. This is likely a function of a somewhat complex set of variables, including the vulnerability of the disulfide bond to "decoupling" as well as its ability to release the toxin upon binding on the surface of target cells.

The general construction of conjugates by means that will provide a disulfide bond between the binding ligand and the toxin A chain is known in the art, as reviewed in references such as 10 and 90, incorporated herein by reference. Disulfide coupling may be achieved directly between cysteine residues of the respective proteins, e.g., by means of disulfide exchange reactions wherein the protein is reduced and derivatized with Ellman's reagent. However, direct disulfide bond formation between the binding ligand and toxin will generally not be preferred, since the cysteine in the ligand is not accessible for coupling. Reduction of the cysteine in the ligand, to provide reactive SH groups, may damage the functional integrity of the ligand. Moreover, when the toxin ligand is coupled without a "spacer", the binding site of the ligand may be sterically hindered.

Accordingly, one will generally find it preferable to employ cross-linking groups which will provide improved release characteristics and resultant therapeutic parameters. A variety of cross-linkers having disulfide groups are known in the art, as exemplified by SPDP, SATA, 2IT and SMPT (10). Generally speaking, suitable cross-linkers will include structures 1) having the ability to covalently coupled to amino groups of lysine, or the like; and 2) incorporating a disulfide or other desired releasable functionality. Useful groups of cross-linkers include the heterobifunctional cross-linkers described above.

Particular useful cross-linkers found to have desirable characteristics in terms of stability, yields and long in vivo half-lives of resulting conjugates include SATA (N-succinimidyl-S-thioacetate) and SMPT (N-succinimidyl-oxycarbonly-alpha-methyl-alpha-(2-pyridyl-dithio)toluene) containing unhindered and hindered disulfide bonds, respectively. SMPT is particularly preferred. Also, another preferred cross-linker is SPDP. A variety of additional functionalists for the purposes of cross-linking conjugates in accordance with the present invention are known in the art and can be substituted for those referred to herein.

In still further embodiments, one may desire to employ one or more additional linking peptide region composed of immunoglobulin-related or derived regions, e.g., ligated to the amino or carboxy terminal of either the binding ligand or the toxin. The inclusion of an immunoglobulin "constant" chain region, e.g., into the gp120 binding ligand portion of CD4-toxin conjugates will allow the binding protein to be "spaced" from the toxin portion such that steric hindrance is avoided, as well as providing a longer in vivo half-life. Where one employs an immunoglobulin constant region domain, one may employ suitable regions from hinge region or Fc region of the heavy chain.

The toxin molecule of the present invention will typically comprise a toxin A chain or toxic derivative thereof. Numerous A chains believed to have suitable anti-cellular properties in the practice of the invention are known in the art. Exemplary A chains which may be employed in connection with the invention include the A chain of ricin, pseudomonas exotoxin, diphtheria toxin, modeccin or abrin, or the "free A chains", known as ribosome-inactivating proteins, e.g., gelonin, saponin. Of these, the ricin A chain molecule is the most preferred due to its high intrinsic anticellular activity and the clinical experience in humans indicating only modest side effects.

In addition to the whole A chain molecule, one may desire to simply employ that portion of the A chain that is necessary for exerting anticellular effects. For example, it has been found that the ricin A chain molecule can be truncated by removal of the first 30 amino acids and nevertheless obtain a toxin molecule that exerts sufficient anticellular activity to be of use in connection herewith. Such termination is achieved by either genetic engineering or proteolytic degradation, e.g., with Nagarase (91), the product being referred to herein as "truncated" A chain.

In the more preferred embodiments of the present invention, a deglycosylated A chain such as deglycosylated ricin A chain (dgA) or variants thereof is employed. Deglycosylated A chain is A chain that has been treated so as to destroy carbohydrate moieties (e.g., mannose, fucose) which are incorporated into naturally produced A chain molecules. It has been found that the presence of mannose/fucose on the oligosaccharide side chains of the A chain promote rapid clearance by the liver and reduced therapeutic effect of the toxin or A chain by hepatic reticuloendothelial cells which have receptors that recognize these structures. The inventors have found that through the use of deglycosylated A chains, one may achieve particular advantages in terms of both increased potency and increased half life of the conjugate and reduced hepatotoxicity in the circulation, by preventing the clearance of the conjugate by the liver parenchymal cells.

While deglycosylated ricin A chain is preferred, there is no reason that other nonglycosylated toxin A chains or ribosome-inactivating protein could not be employed in connection with the invention. In any event, the preparation and use of deglycosylated A chain is known in the art as illustrated by references such as Thorpe et al. (59) and Fulton et al. (60), both incorporated herein by reference. Moreover, deglycosylated A chain is now available commercially from Inland Laboratories, Austin, Tex.

Additionally, the preparation of ricin A chain by recombinant means is now known, as exemplified by O'Hare et al. (60), incorporated herein by reference. Thus, as with the CD4 portion, it is now possible to alter the amino acid structure through the application of in vitro mutagenesis technology. Through the judicious selection of amino acid sequence alterations or modifications based on knowledge of interactive forces between amino acids, one can readily modify or alter the A chain sequence and provide a means for selecting variant proteins having improved toxicity, pharmacologic or release properties.

In still further embodiments of the invention, it is contemplated that several CD4 gp120 binding ligands may be conjugated to a single toxin A chain moiety. It is proposed that such constructs, containing up to, for example, 5 or so gp120 binding ligands per toxin moiety, will find particular therapeutic benefits. It is, for example, believed that such constructs will have a particular high binding affinity for env targets of HIV infected cells, thereby providing enhanced ability to deliver toxin to these infected cells and thereby kill them.

It has been found by the inventors that ricin B-chains alone, or coupled to antibody, can serve to greatly enhance the specific cytotoxicity of immunotoxins containing ricin. B chains are the "lectin" binding regions of the toxin complex that are responsible for the native toxin's broad ranging cell-binding capability. The inventors have discovered that not only do B chains stimulate immunotoxin action, but that one can "separate" pharmacologically this action from the cell-binding function by chemical heat modification of the B chain (88). It is thus proposed that the application of toxin B chains in combination with the A chain conjugates will provide advantages in terms of even further specific cytotoxicity against HIV infected cells.

While the B chain can be employed in an "unmodified" state while conjugated to a separate binding agent, such as an antibody having binding affinity for a CD4-toxin conjugate (87), this will generally not be preferred. A more preferred construct employs a "modified" B chain that has been altered to remove regions responsible for carbohydrate binding. Generally this will include modifications involving at least the amino acid residues Asn-255 (and perhaps Tyr-248 and/or Asp-234), such as through the application of genetic. engineering techniques to the cloned ricin B chain (89).

Thus, in accordance with certain embodiments of the invention, one will desire to employ a modified B chain either disposed in the form of an additional conjugate onto the CD4 env binding ligand-toxin conjugate, whether it be attached to the toxin or binding ligand segment, or on a separate binding ligand having specificity for the first.

In still further embodiments, the present invention concerns improved methods for the preparation of ligand-toxin conjugates. A particularly useful method involves, first, preparation of a gp120 binding ligand which has been derivatized with a selected linker, followed by incubating the derivatized binding ligand with a reduced form of the selected toxin A chain. Of course, a linker is chosen for derivatization which is capable of covalently binding with the reduced toxin moiety, and vice versa, yet capable of releasing the active toxin intracellularly.

The inventors have discovered that an improved preparation is achieved by incubating this mixture for shorter periods of time than typically recommended for the preparation of immunotoxins, which are typically prepared by incubation for 72 hours. In contrast, in connection with toxin conjugates of this invention it has been discovered that it is preferable to subject the reactants to attachment conditions of less than 72 hours. Under these conditions, it is found that the resultant conjugate mixture is surprisingly free of aggregated material relative to compositions wherein reactants are subjected to longer periods of attachment conditions. Moreover, the preferred techniques of the present invention are particularly applicable to large scale preparation, capable of providing generally less aggregated conjugates in higher yields, improved sterility, or even lower endotoxin content.

As used herein, the phrase "large scale" is intended to refer to those reaction mixtures wherein the design is to prepare quantities of greater than about 1 gram of total product, often on the order of 2 to 5 grams, or even more. This is as compared to more "small scale" preparations ranging up to about 0.1 grams.

The most preferred conditions for covalently attaching the derivatized gp120 binding ligand to toxin moiety include incubation under attachment conditions for between about 12 and about 72, with about 18 to 36 often being particularly useful, and with about 24 hours often optimal.

Of course, the preferred binding ligand, particularly for such large scale preparation, will typically be CD4, or an active subportion thereof, and the preferred linker will typically be SMPT, SATA or SPDP.

Accordingly, an important aspect of the invention is the preparation of pharmaceutical compositions which incorporate the CD4 gp120 binding ligand-toxin conjugates in therapeutically effective amounts. Of course, where pharmaceutical compositions are prepared, one will desire to employ conjugates that are essentially free of unconjugated material and, further, does not contain any undesired impurities. Therefore, one will generally find it necessary to purify conjugates prepared in accordance with the invention through the application of purification technology. Disclosed herein are techniques discovered by the present inventors for isolating and purifying conjugates to a very high degree.

In certain aspects, the present invention is thus directed to techniques for purifying immunoconjugates, including conjugates such as the gp120 ligand-toxin conjugate. Particular techniques which have been found useful in the purification of conjugates in accordance herewith include affinity chromatography techniques employing Blue-(or Red) Sepharose. Sepharose conjugated to recombinant gp120, molecular exclusion chromatography on Sephacryl or even gel permeation by HPLC. The best results in terms of rCD4-dgA conjugates have been achieved by combining Blue-Sepharose with HPLC chromatography.

Pharmaceutical compositions comprising conjugates of the present invention are typically prepared by combining the purified conjugate with a pharmaceutically acceptable diluent or excipient for parenteral administration. A variety of suitable carrier vehicles and their formulation are described, for example, in reference 63, incorporated herein by reference. Suitable carriers include sterile aqueous solutions including stabilizing agents, e.g., buffers and other protein and pH-stabilizing agents, salts and the like. Typically, sterile aqueous compositions of the desired conjugate will include a dose concentration of between about 0.5 and about 1.0 mg/ml, to allow for administration of convenient amounts.

In certain embodiments, the appropriate dose of conjugate to be administered will be somewhat dependent upon the particular patient. Those of skill in the art of immunotoxin administration will appreciate that one will desire to administer on the order of 200 to 400 mg of the conjugate is employed (for an average 70 kg human), depending upon the appearance of untoward side effects such as vascular leak syndrome (VLS), myalgia, fatigue and/or fever. Other considerations include the administration of the conjugates in 2–7 fractional doses.

It is further proposed that additional benefit will be realized by the application of chloroquine alone or together with the conjugates of the present invention. It has been found by the inventors that chloroquine alone exhibits significant anticellular activity against HIV infected cells. Furthermore, chloroquine will act in concert with the toxin conjugates of the present invention to improve their anti-HIV efficacy. In both instances, it is suggested or has been found that the amount of chloroquine to be administered to a patient in need of such therapy will be similar to that amount normally administered for other indications of chloroquine, such as in the treatment of malaria. In general, one will desire to administer from about 3 mg/kg to about 10 mg/kg doses for 10 days, and more particularly about 8 mg/kg to about 10 mg/kg for 10 days, with about 10 mg/kg being generally the preferred dosage.

Under certain circumstances, untoward reactions or toxicity may develop from the administration of therapeutic compositions which contain toxin conjugates such as those described herein. Possible side effects will range from slight fever to myalgia and perhaps even VLS. Many of these side effects will likely be attributable to a response of the immune system of the individual being treated. The inventors propose that some degree of relief from such symptoms can be realized through the application of one or more agents directed to attenuating the immune response, including both agents which address a possible T cell response as well as any attendant NK cell including, lymphokine or cytokine production.

It is therefore proposed that in certain embodiments one will desire to administer agents such as high dose steroids or cyclosporin A, in order to address any possible B cell component which may be responsible for side effects. Furthermore, to address any possible T cell response, one may desire to administer anti-lymphokine antibodies, including agents such as anti-IL2 (anti-interleukin II), ALS, or even Anti CD3, CD5 or CD7. Additionally, some benefit may be realized through administration of antibodies against lymphokine receptors such as alpha-IL2R or alpha-IL4R, or even antibodies against T-cells themselves, such as anti-CD4 (so long as the antibody is directed against epitopes not found in the toxin conjugate being employed), CAmPATH-1, or anti-CD3, 5, 7, or the like.

The rCD4-dgA (-○-), Fab'-MOPC-21-dgA (-●-) (76), and rCD4 (Δ) were plated in triplicate in 96-well microtiter plates in complete medium [RPMI, 12% fetal calf serum (FCS), and antibiotics). Cells were added at a final concentration of $4\times10^5$ cells per milliliter and plates were incubated for 16 hours at 37° C. (5% $CO_2$). Cells were pulsed for 6 hours with 1 uCi of [$^3$H]thymidine (77) and harvested on a Titretek automatic harvester. [$^3$H]thymidine incorporation was determined on an LKB Beta Counter. Results are expressed as a percentage of control (untreated cells).

FIG. 4. The killing of HIV-infected H9 cells by rCD4-dgA is blocked by an excess of rCD4, rgp120 (78), or MAbs to the gp120 binding site of rCD4 (Leu-3a), but not another epitope on CD4 (MAb 456) (79). rCD4-dgA was used at a final concentration of $4\times10^{-10}$M. Microtiter plates containing HIV-infected H9 cells were incubated. [$^3$H]thymidine was added, and the cells were harvested as described in FIG. 3. Results are expressed as the percentage of [$^3$H]thymidine incorporation in untreated cells. The bars represent the average of four experiments. The SD among experiments was 20%.

A) Cells were treated with rCD4-dgA, which has been incubated for 1 hour at 37° C. with
  1) medium;
  2) BSA, 25 ug/ml; and (3 to 5) rgp120 at 0.125, 2.5 and 25 ug/ml, respectively.

B) Cells were treated with rCD4-dgA, which had been incubated for 1 hour at 37° C. with
  1) medium;
  2) MAb 456, 25 ug/ml; and C) Cells were incubated with rCD4 or controls at 37° C. for 1 hour. rCD4-dgA was then added at a final concentration of $4\times10^{-10}$M. Cells were incubated, pulse-labeled, and harvested as described in FIG. 3. rCD4-dgA-treated cells were first cultured with
  1) medium;

2) BSA. 25 ug/ml; and (3 to 5) rCD4 at 0.125, 2.5, and 25 ug/ml, respectively.

FIG. 5. The rCD4-dgA conjugate does not kill class II⁺ Daudi cells. rCD4-dgA (●) or MAb to class II-dgA (79) (○) was titrated into 96-well microtiter plates. Daudi cells were added to a final concentration of $4 \times 10^5$ per milliliter. The plates were incubated for 16 hours at 37° C. The cells were centrifuged, resuspended in leucine-free medium, pulse-labeled with [³H]leucine (5 uCi per well), and harvested as described in FIG. 2. One representative experiment of three that were performed is shown.

Figure 6:
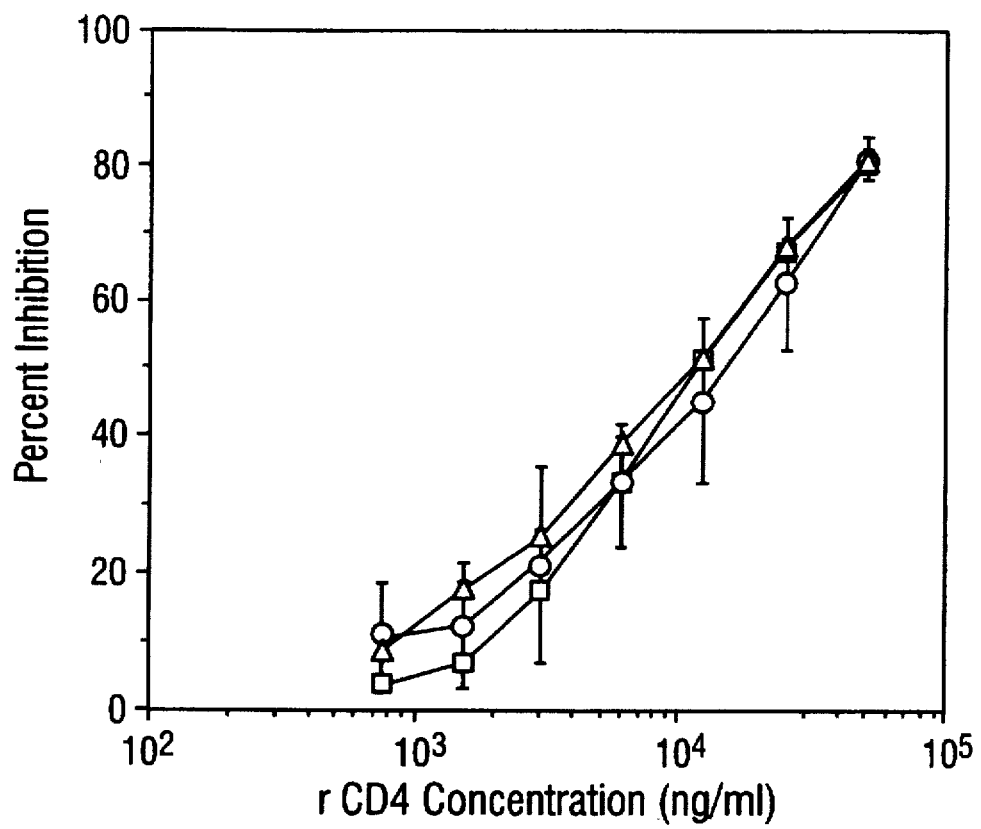

FIG. 6. rCD4/rgp120 competitive binding assay. The percent inhibition of fluorescent signal was calculated as 100% (1-[sample-background)/(total signal-background)]. The competitors were rCD4-SATA-dgA (■), rCD4-SMPT-dgA (□) and rCD4 (○). The binding of each conjugate was based on its rCD4 content. The bars indicate the S.D. for the rCD4 curve.

Figure 7:
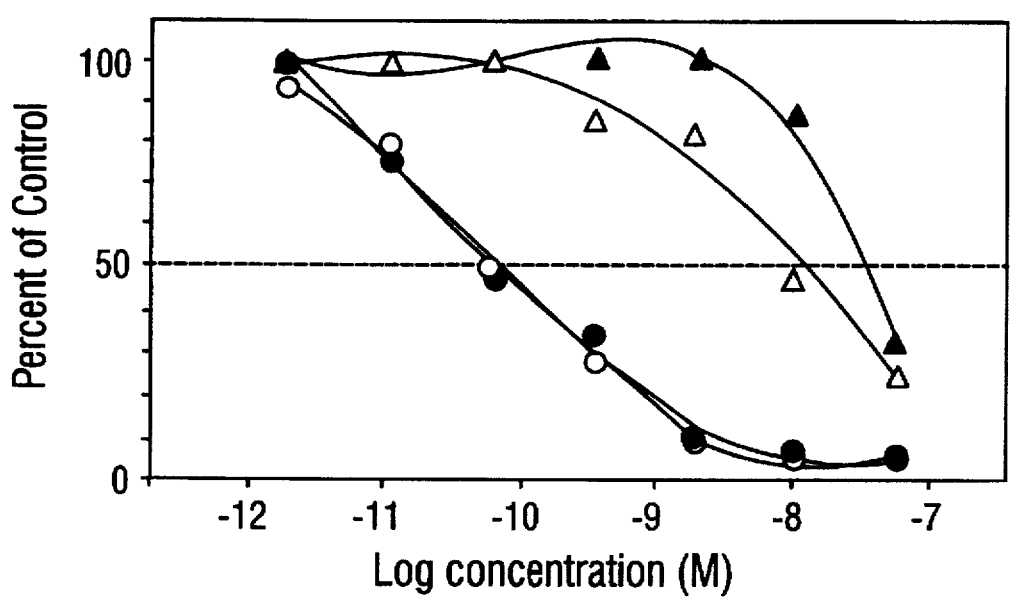

FIG. 7. The toxicity of the three rCD4-dgA conjugates and OVA-dgA (control) to HIV-infected H9 cells. (0) rCD4-SMPT-dgA; (●) rCD4-SATA-dgA; (Δ) rCD4-SMCC-dgA; (▲) OVA-SMPT-dgA. One representative experiment of 5 (SMPT) and 8 (SATA) is depicted.

Figure 8:
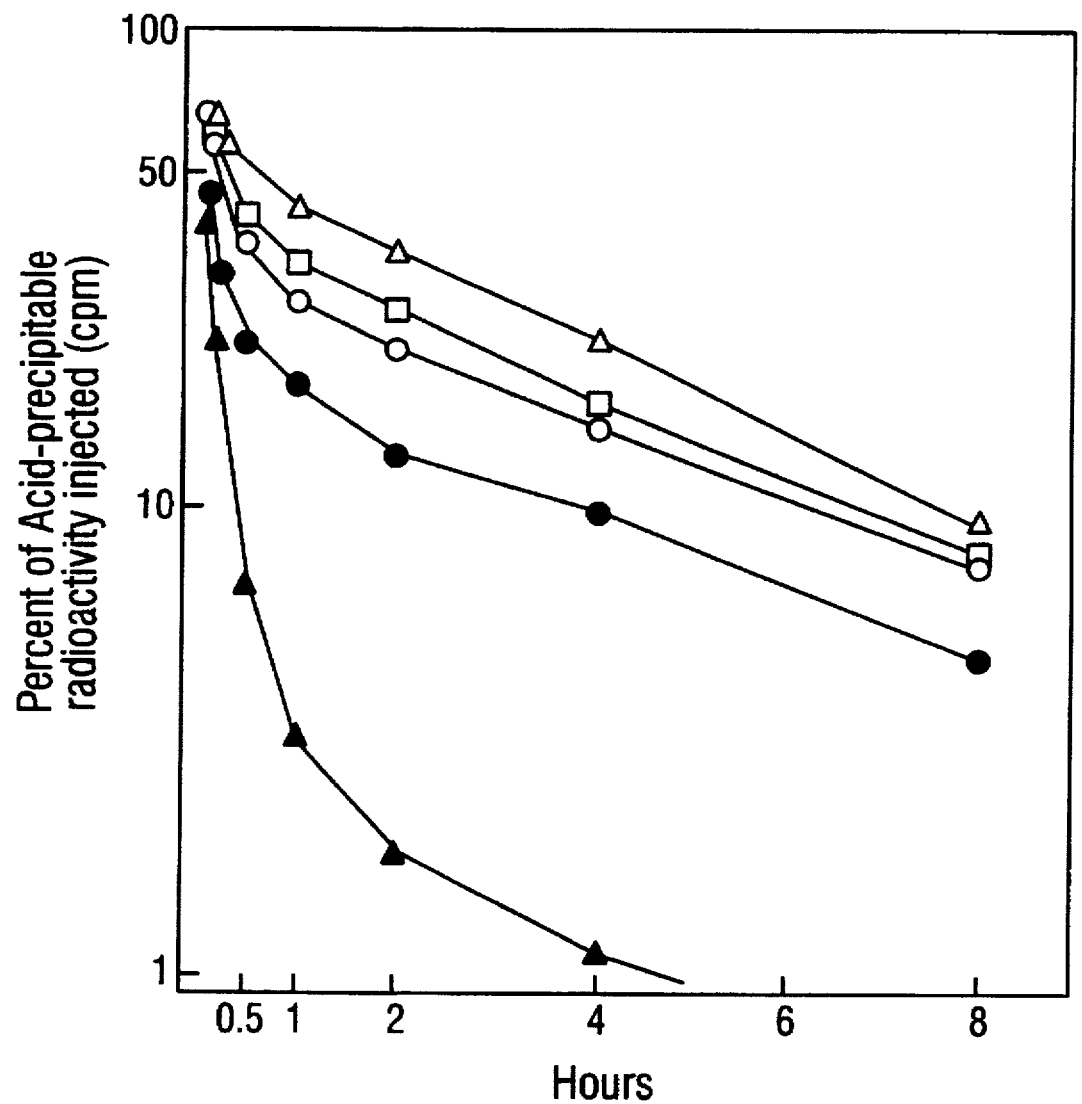

FIG. 8. The elimination curves of rCD4-dgA conjugates and their protein components in mice. The results are from one experiment of 3 performed.
-Δ-, rCD4-SMPT-dgA; -□-, rCD4-SATA-dgA; -0-, rCD4-SMCC-dgA conjugate; -●-, dgA; -▲-, rCD4.

Figure 9:
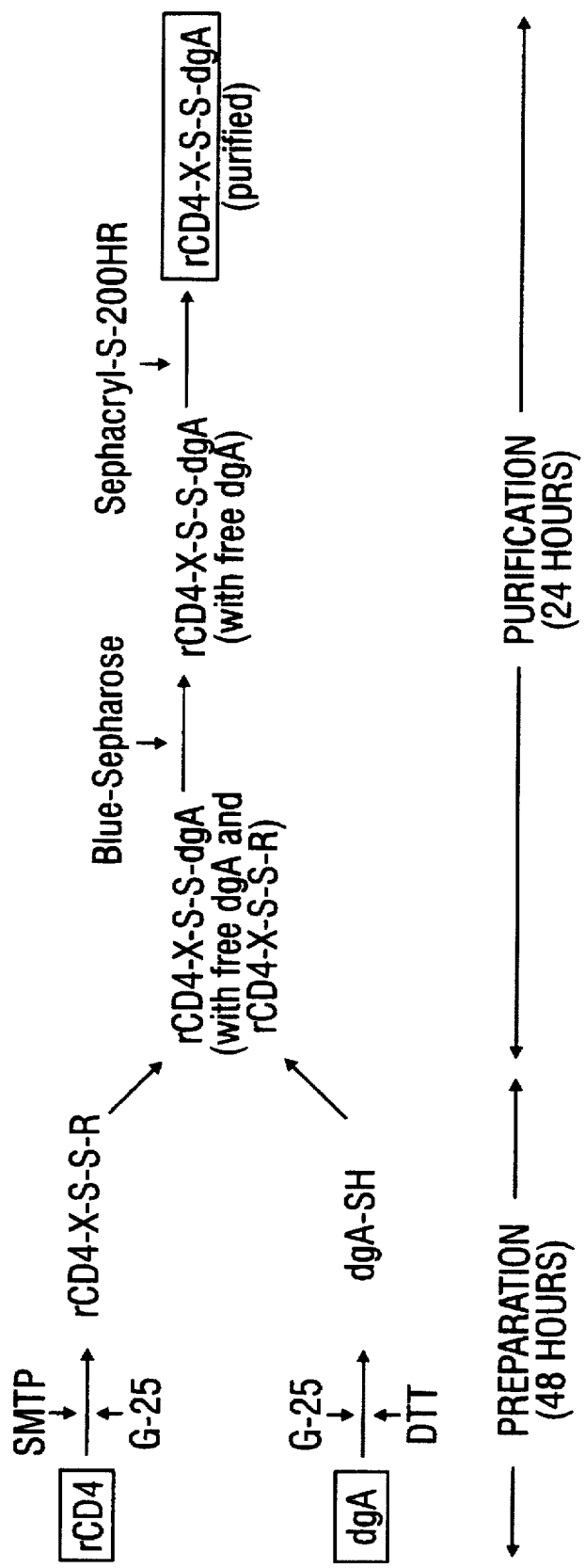

FIG. 9. The preparation of rCD4-dgA conjugates. R=pyridyl; X=oxycarbonyl-α-methyl-toluene (protecting the disulfide bond).

Figure 10:
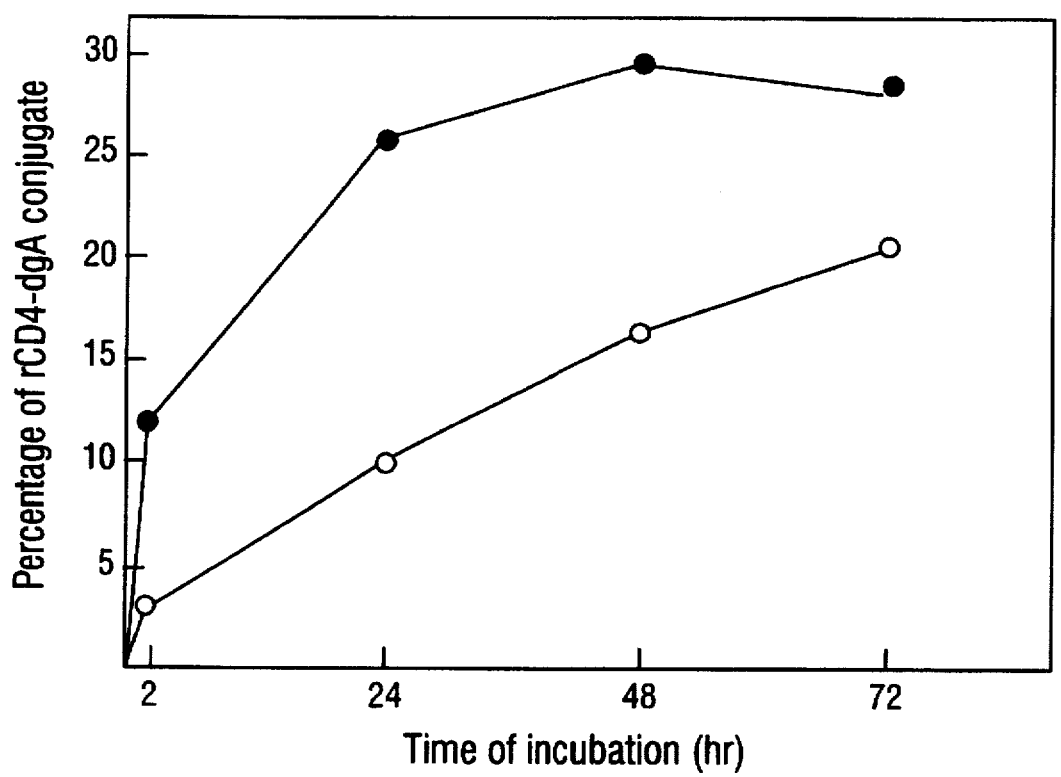

FIG. 10. Kinetics of rCD4-dgA formation by reaction of rCD4-MPT with dgA-SH. (●) rCD4-dgA (80 kDa); (0) rCD4-dgA (aggregated).

Figure 11A:
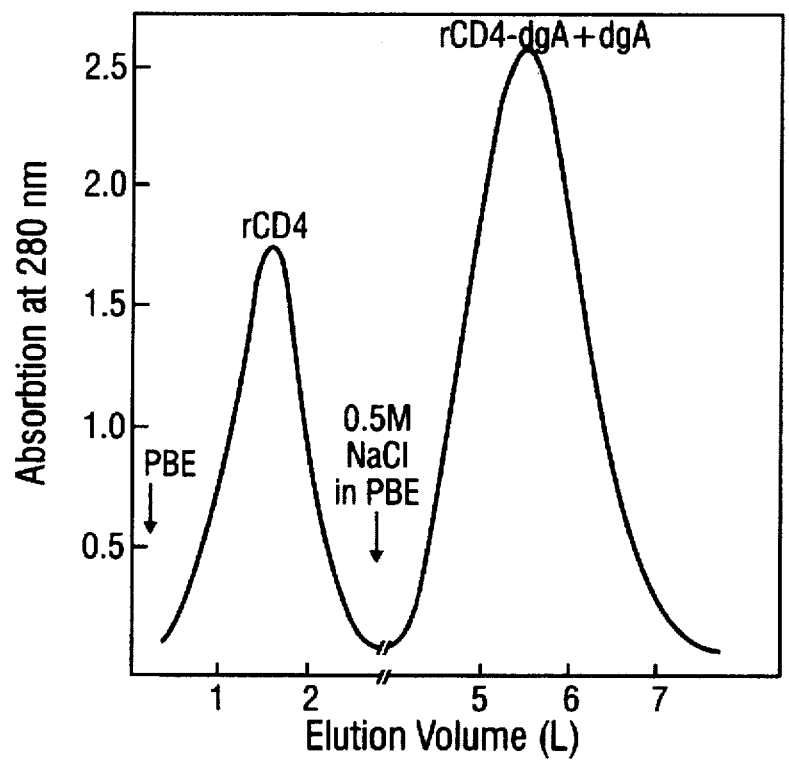
Figure 11B:
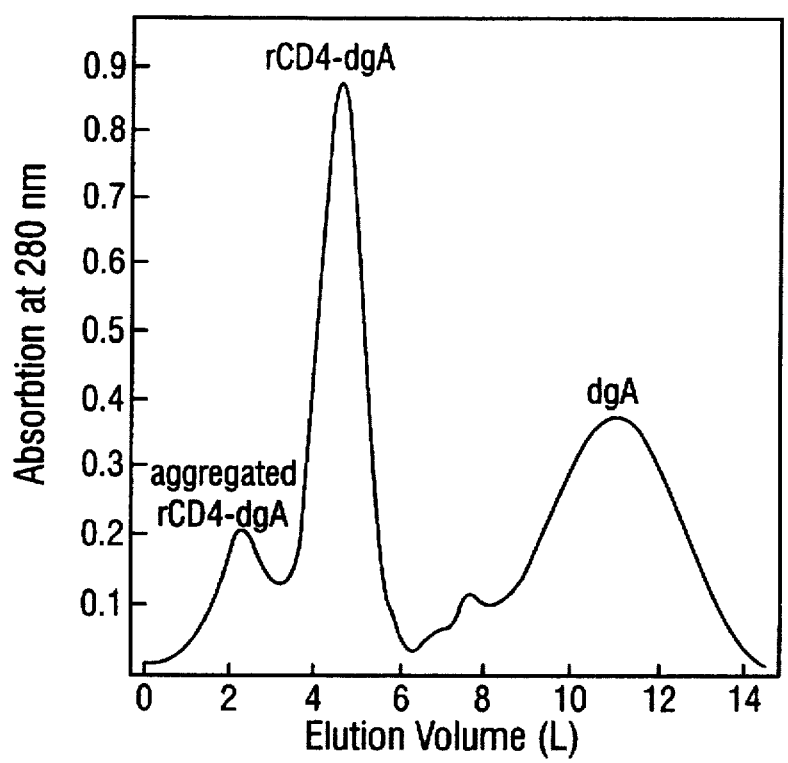

FIG. 11. Purification of rCD4-dgA.
A. Blue-Sepharose CL-4B (rCD4=35%; rCD4-dgA+dgA=65%);
B. Sephacryl S-200HR (aggregated rCD4-dgA=10%; rCD4-dgA=42%; dgA=48%).

Figure 12:
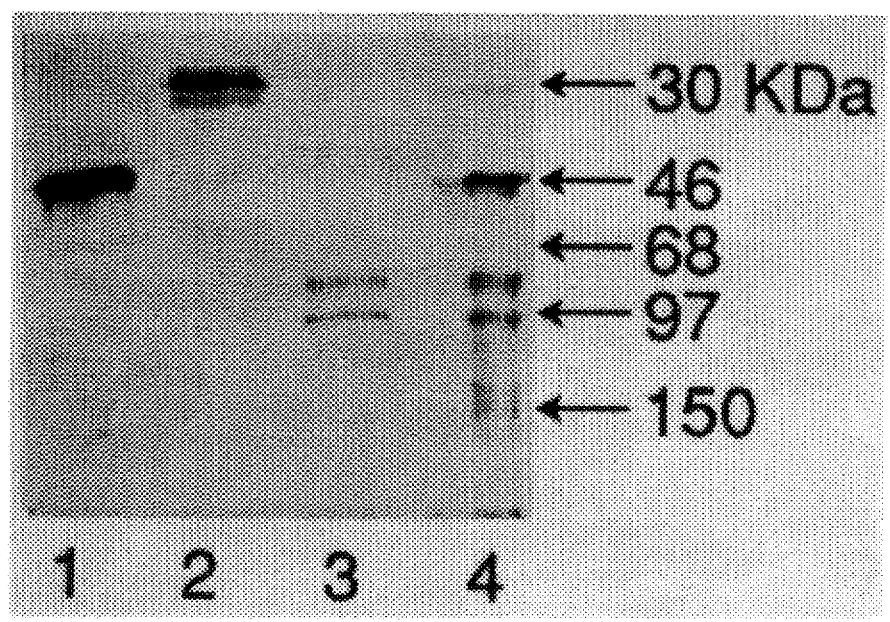

FIG. 12. SDS-PAGE of rCD4-dgA and its components. 1) rCD4; 2) dgA; 3) rCD4-dgA purified; 4) mixture of rCD4-MPT+dgA-SH containing free dgA (30 kDa), free rCD4 (45 kDa), rCD4-dgA conjugate (75 kDa and 97 kDa) and aggregated rCD4-dgA conjugate (120–150 kDa).

FIG. 13 sets forth the primary structure of the first 100 amino acids of CD4 containing the V1 domain. Amino acids 78–94 is the region identified by Jameson et al. (95), 41–55 by Antros et al. (96), and 81–92 by Lifson et al. (68). There is a disulfide bond between the cysteine residues at position 16 and 81. Amino acids 1–94 represent the V1 domain, and 94–112, the J1 segment.

Figure 14:
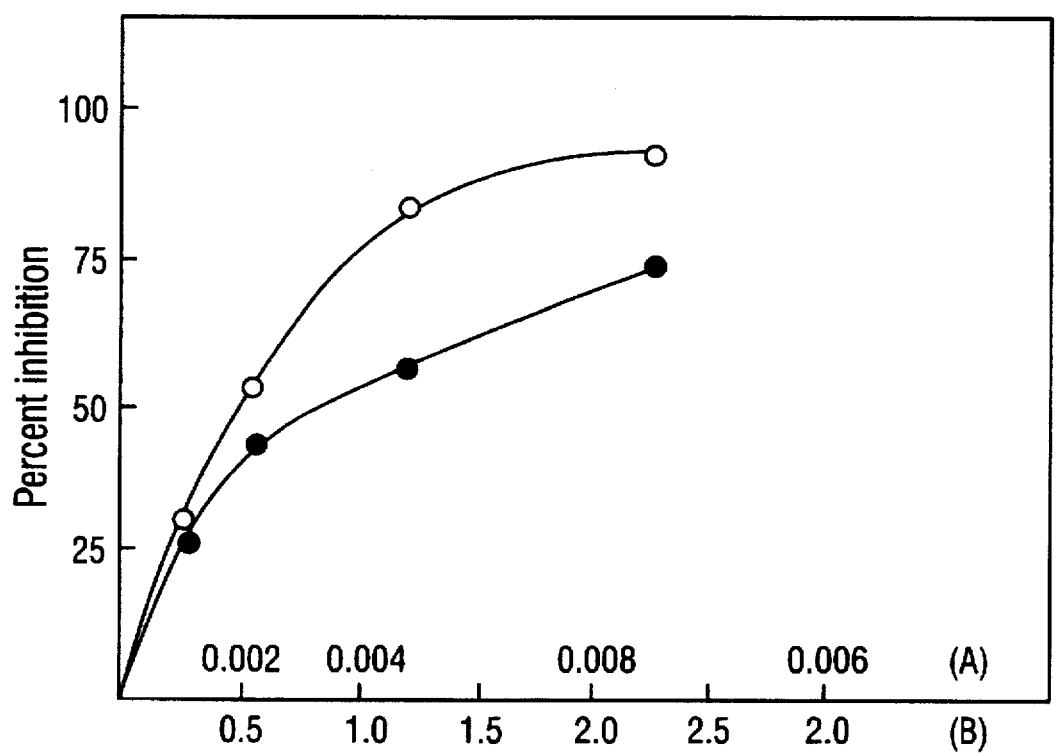

FIG. 14 graphically demonstrates the inhibition of HRP-labeled CD4 binding to gp120-coated cells by peptide 41–57—BSA conjugate. The rCD4 concentration (μM) (A) is represented by (-●-), while Peptide-S-S-BSA concentration (μM peptide) (B) is given by (-○-).

Figure 15:
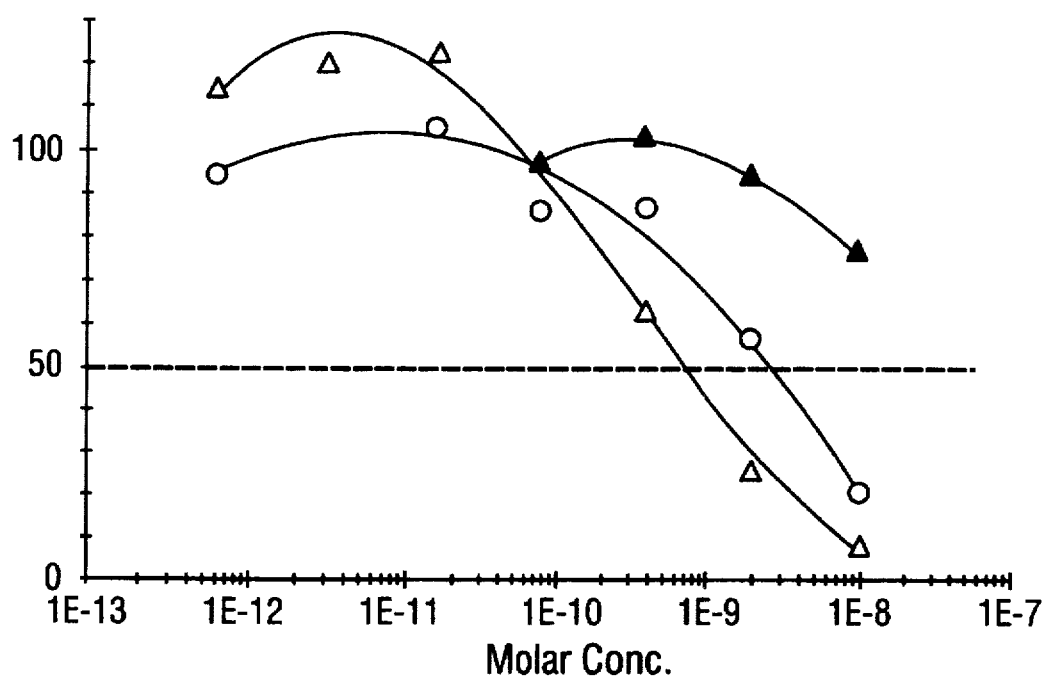

FIG. 15 shows the killing of HIV-1-infected human H9 cells by CD4-dgA and peptide (41–57)-S-S-BSA-S-S-dgA. The effect of peptide-S-S-BSA-S-S-dgA on HIV-H9 is represented by (○), of rCD4-dgA on HIV-H9 by (Δ), and peptide-S-S-BSA-S-S-dgA on H9 by (▲).

FIG. 16 shows the primary structure of a portion of the ricin A chain molecule, including the hydroxylamine splitting point (141–142), the CNBr splitting points (174, 188, and 253), a "hidden" cysteine residue that does not react with DTNB (171), and the cysteine residue involved in the binding of B chain or gp120 binding peptide (257).

Figure 17A:
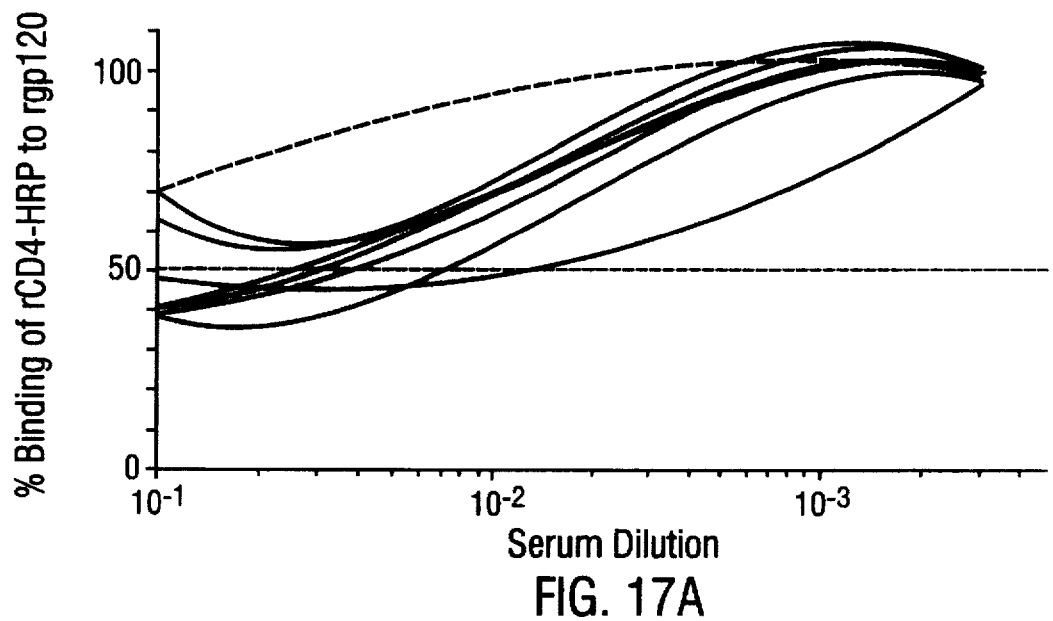
Figure 17B:
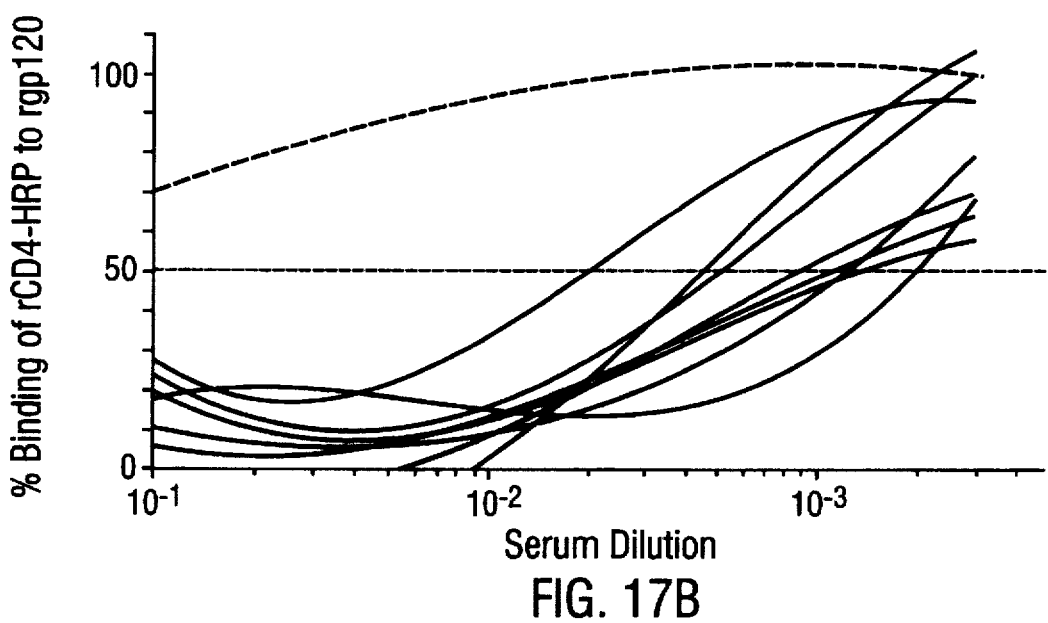

FIG. 17 shows inhibition of the binding of rCD4-HRP to rgp120 by
A. HIV⁻ sera (8 individuals) or HSA (- - -);
B. HIV⁺ sera (8 individuals) or HSA (- - -).
The following dilutions were used: $10^{-1}$, $2 \times 10^{-2}$, $10^{-2}$, $5 \times 10^{-3}$, $2.5 \times 10^{-3}$, $1.25 \times 10^{-3}$, $0.62 \times 10^{-3}$, and $0.31 \times 10^{-3}$ and the curves were computer-generated.

FIG. 18 shows absorption of sera on rgp120-Sepharose, protein A-Sepharose and rCD4-Sepharose.
A. HIV⁺ and
B. HIV⁻ sera
were passed over small chromatographic columns packed with 3 ml of the following gels: rCD4-Sepharose (●); gp120-Sepharose (Δ); protein A-Sepharose (▲); uncoupled Sepharose 4B (□). (■)=nonchromatographed serum.

Figure 19:
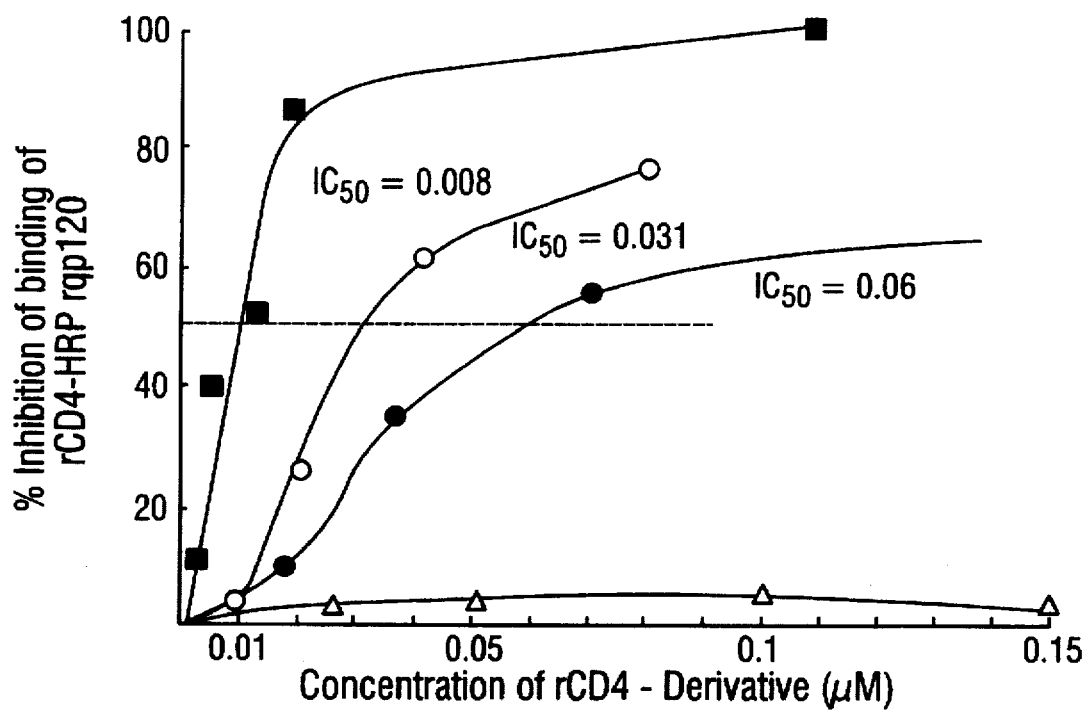

FIG. 19 shows inhibition of the binding of rCD4-HRP to gp120 by rCD4 and CD4-peptides. rCD4 (□), CD4-peptide (41–84) (○). CD4-peptide (40–57)-OVA (●). CD4-peptide (81–92)-OVA (Δ) or OVA (Δ).

Figure 20:
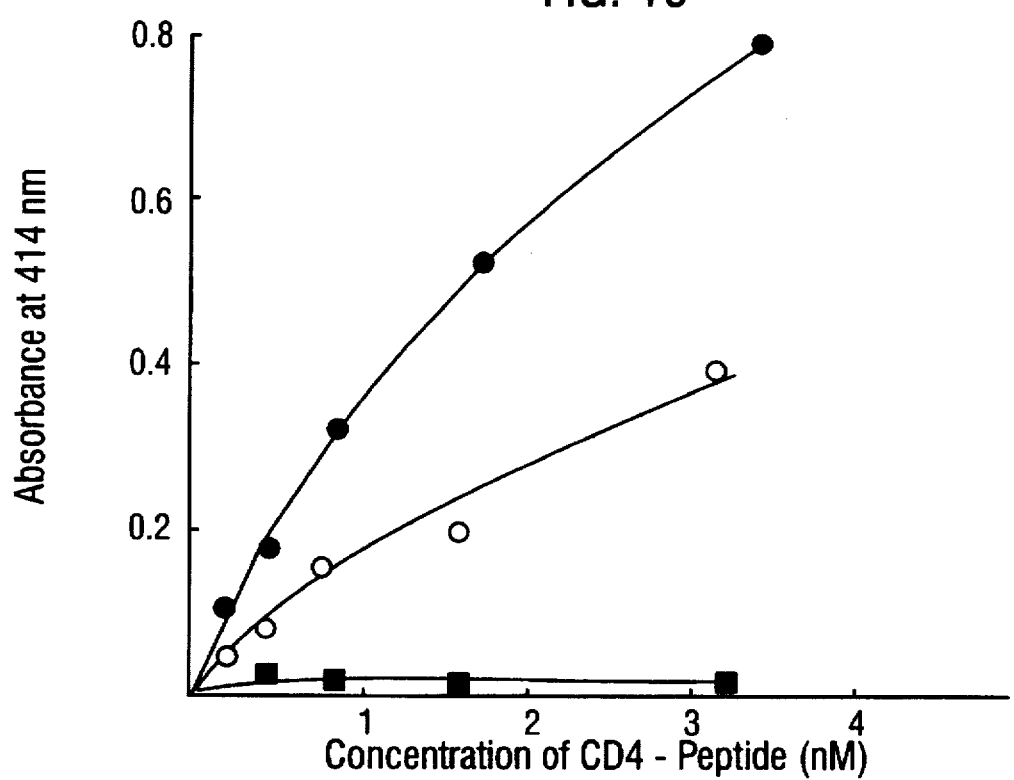

FIG. 20 shows binding of CD4-derived peptides to rgp120. CD4-peptide (41–84)-OVA (●); CD4-peptide (40–57)-OVA (○); CD4-peptide (81–92)-OVA (■). Control peptide-OVA and OVA (■).

Figure 21A:
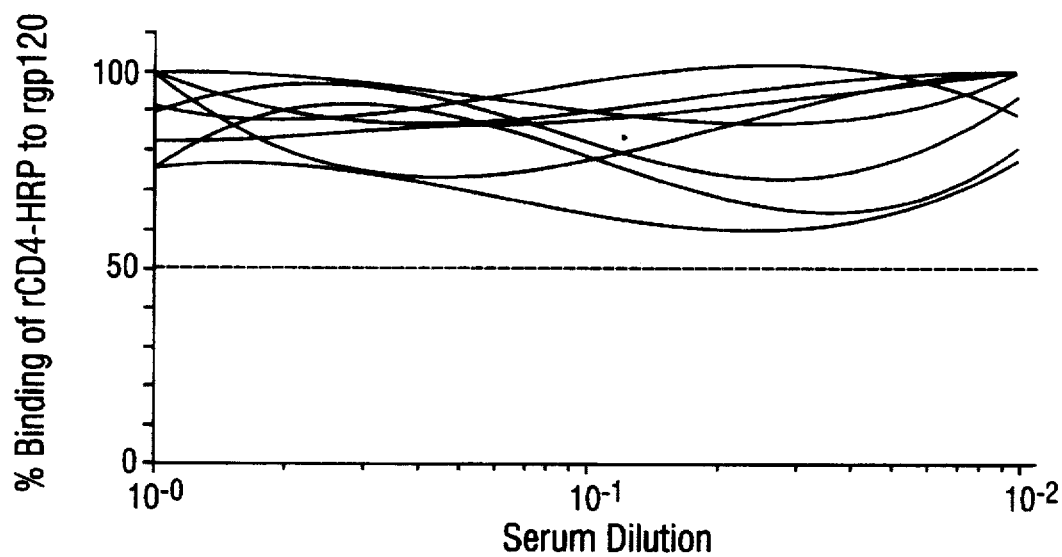
Figure 21B:
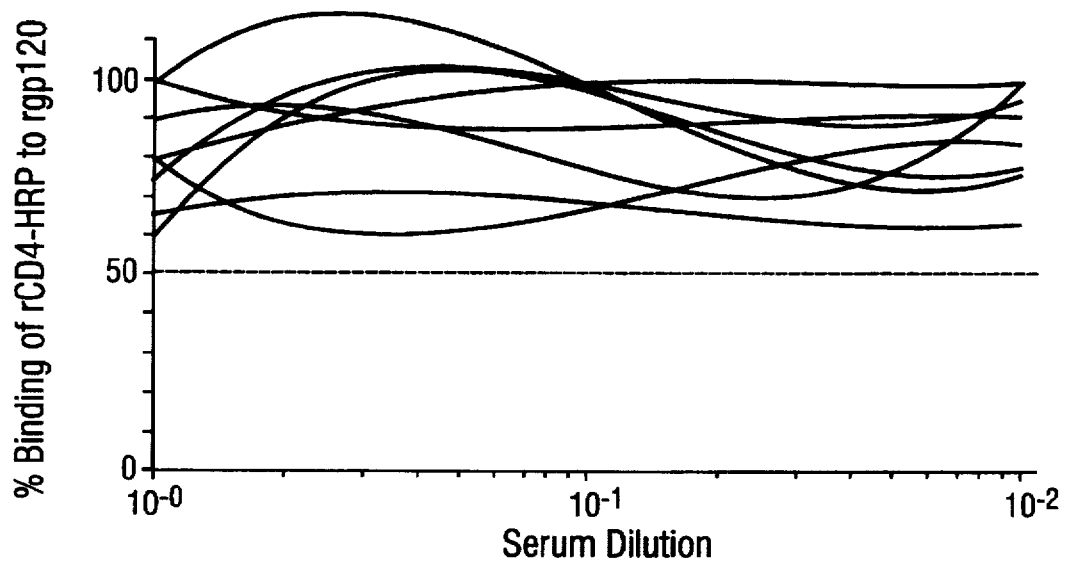

FIG. 21 shows inhibition of the binding of CD4-peptide (41–84)-OVA to rgp120 by
A. HIV⁺ sera (8 individuals) and
B. HIV⁻ sera (8 individuals).
See legend to FIG. 17 for dilutions used.

DETAILED DESCRIPTION OF THE PREFERRED EMBODIMENTS

This invention relates to the preparation and use of CD4-toxin conjugates, defined broadly as conjugates between gp120 binding ligands and a toxin A chain. Preparation of the CD4 moiety of the conjugate is generally well known in the art as set forth in references 23–25. These references describe the recombinant preparation of CD4 and CD4 variants, including "soluble" CD4 which is to be considered a preferred ligand for toxin A chain conjugation.

The preparation of toxin A chains from a variety of species and sources is generally well known in the art, as exemplified by references such as reference 63. The term "toxin A chain" is thus intended to encompass all toxin A chains, including ricin, diphtheria, modeccin, abrin, and the like, as well as biological functional equivalents of these A chains. As noted in the Summary section above, ricin A chain will generally be preferred in the practice of the invention. Furthermore, in that the cloning of ricin A chain has now been accomplished (69), this molecule can be engineered to provide toxin A chains having variant structure and "tailored" biological properties. Furthermore, the use of deglycosylated A chain is particularly preferred due to the improved pharmacodynamics of this molecule in relation to ricin A chain.

The most preferred gp120 binding ligand will generally be smaller peptides which incorporate CD4-derived gp120 binding regions into their structures. Preferably, the peptidyl regions that are employed will be ones that do not include sequences that recognize and bind to Class II binding sites that are normally recognized by CD4. This is somewhat important in that many Class II⁺ cells will not generally be HIV infected. Thus, any targeting to Class II cells will be contraindicated in that it may tend to deplete the body of uninfected cells, rather than directly addressing the HIV infection. Accordingly, one will generally desire to employ a gp120 binding ligand that is devoid of class II binding activity and will direct the toxin conjugate only to cells bearing HIV-derived env determinants.

It will therefore be generally desirable in the practice of the invention to employ peptides having a gp120 binding sequence derived from the domain 1 of CD4 (domain 1 comprises about amino acids 1 to about 100/109 of the CD4 amino acid sequence, with the pre-domain 1 leader sequence comprising amino acids -25 to -1, see reference 23). Domain 1 is, of course, encompassed within the entire CD4 protein. Thus, where desired, the entire CD4 protein can be employed in the practice of aspects of the invention. However, the use of the native CD4 protein will generally not be desired due to the size of the molecule, rendering it undesirable pharmacologically, as well as its propensity for binding to Class II targets, rendering it undesirable therapeutically.

A possible means of addressing these problems, as noted above, is through the use of "soluble" CD4 which, for unknown reasons, fails to bind to Class II targets even though a Class II binding site is apparently contained within either the first or second domain of CD4, or at their juncture. However, even soluble or extracellular CD4 is nevertheless a relatively large ligand, comprising some 368 amino acids, and thus is not ideal.

The ideal binding ligand, for the purposes of the present invention, will be a ligand bearing just enough of an amino acid sequence so as to adequately form a complex with the env determinant and thereby deliver the toxin to HIV infected cells. Thus, one possible ligand that will serve as an improvement to the aforementioned "soluble" CD4 is a peptide corresponding essentially to the first domain of CD4 (amino acids 1-100/109), or a biologically functional equivalent of such a sequence (see FIG. 13). The inventors have, e.g., found that immunoconjugates containing either the four extracellular domains of CD4 (98, 99), or its first two domains coupled to deglycosylated ricin A chain (dgA) can selectively kill HIV-infected cells with $IC_{50}$s of $10^{-10}$ to $10^{-9}$M.

However, it is proposed that still other advantages over soluble CD4 will be realized through the use of even shorter peptidal regions, such as represented by amino acids 41–57 of CD4 (measured with the initial MET as -25). The amino acid sequence of this portion of CD4 is:

persistence in circulation. In any event, it is proposed that the use of any serum soluble protein or non-protein macromolecule, particularly autologous proteins, will find utility in accordance herewith.

Further, where the 41–57 region of CD4 is employed directly, the inventors have found it beneficial to incorporate a short stretch of additional amino acids at its carboxy terminus prior to conjugation. It is believed that the use of these additional amino acids serve to prevent steric hindrance between the binding region and the spacer molecule, allowing freer rotation of the binding region. The inventors routinely employ the addition of the two amino acids -Ala-Cys to the carboxy terminus. The use of a cysteine residue as the carboxy terminus allows conjugation directly by disulfide bond formation. However, it is believed that the length and sequence character of this region is not particularly crucial, so long as it provides good accessability to its associated binding ligand.

Even more particular advantages may be obtained by employing CD4 peptidal regions comprising from about 25 to 50 amino acids in length, such as represented by amino acid residues 41–84. The amino acid sequence of this portion of CD4 is:

```
   41              45                50                  55
—Gly—Ser—Phe—Leu—Thr—Lys—Gly—Pro—Ser—Lys—Leu—Asn—Asp—Arg—Ala—Asp—Ser—

60                  65               70                75
Arg—Arg—Ser—Leu—Trp—Asp—Gln—Gly—Asn—Phe—Pro—Leu—Ile—Ile—Lys—Asn—Leu—Lys—

80
Ile—Glu—Asp—Ser—Asp—Thr—Tyr—Ile—Cys—
```

The inventors have demonstrated that the CD4 (41–84) peptide is even more effective as a gp120 binding ligand than the CD4 (41–57) peptide. Although CD4 (41–84) peptide can interact with gp120, increased affinity results when the peptide is coupled to a macromolecule, forming a gp120 binding ligand-macromolecule conjugate. As discussed for peptide CD4 (41–57) above, optimizing the combination of spacers, gp120 binding ligands [e.g., CD4 (41–57)], macromolecules, and toxins may yield conjugates with many beneficial functions, e.g., the incorporation of multiple binding ligands and toxin molecules per conjugate, higher affinity for gp120 on the virus or env determinants on HIV-infected cells, better spatial configuration, or longer conjugate half-life in circulation.

For example, CD4 (41–84) was shown to have a higher affinity for gp120 than CD4 (41–57) or CD4 (81–92) after conjugation with a carrier protein such as ovalbumin (OVA). Although the affinity of CD4 (41–84)-OVA conjugates was less than the affinity of rCD4 for gp120, CD4 (41–84)-OVA

```
41              45              50              55
Gly—Ser—Phe—Leu—Thr—Lys—Gly—Pro—Ser—Lys—Leu—Asn—Asp—Arg—Ala—Asp—Ser
```

The inventors have demonstrated that this sequence can be used directly in gp120 binding ligand-toxin conjugate, preferably in connection with a spacer region, such as BSA, HSA, N-hydroxysuccinimide esters or the like, placed between the binding ligand and the toxin. It is believed that such spacer regions may serve many possible beneficial functions, not the least of which is the ability to incorporate a relatively large number of binding ligands or even toxin molecules per conjugate. Other possible benefits include higher affinity, better spacial configuration or even longer constructs were capable of binding gp120 in the presence of HIV$^+$ sera, whereas rCD4 binding to gp120 was blocked by HIV$^+$ sera. The blockage of rCD4 binding to gp120 by HIV$^+$ sera was caused by anti-gp120 antibodies, which would likely block the attachment of CD4-toxin conjugates to either gp120 on the virus or env on HIV infected cells. Consequently, CD4-based therapies for HIV infection would be ineffective if inhibitory anti-gp120 antibodies were present. The construction of peptide-toxin conjugates that bind gp120 in the presence of anti-gp120 is believed to offer significant advantage for AIDS therapy by allowing toxin to destroy HIV infected cells expressing env which are inaccessible to rCD4-dgA conjugates. Thus, in more particular embodiments, this invention would utilize conjugates of CD4 peptide (41–84)-ricin dgA to destroy HIV infected cells, which may not be accessible to rCD4-dgA in AIDS patients with high anti-gp120 titers.

Thus, in preferred aspects, one will desire to employ as the gp120 binding ligand a peptide incorporating the foregoing amino acid sequences, or a portion thereof, and having from at least about 12 to about 50 amino acids in length, with about 40 amino acids in length being preferred. It is proposed that binding ligands of this length will provide particular benefits relative to much larger proteins or peptides in terms of greater biodistribution, decreased metabolic destruction, absence of a class II-binding site, decreased liver homing and thus metabolic destruction.

Of course, where the peptide binding ligand is 17 amino acids in length, it will have a sequence consisting essentially of the first binding region shown above (i.e., CD4 41–57). However, where larger peptides are envisioned, it is proposed that all that is required is that the peptide will incorporate the above sequence in a manner which nevertheless retains the intrinsic binding ability of this peptidyl region, e.g., CD4 peptide 41–84.

In addition to proteins or peptides which incorporate sequences or sequence regions derived from a consideration of the CD4 sequence, the present invention contemplates that such sequences can be varied and nevertheless obtain peptide sequences that will serve the function of gp120 binding. For example, it is proposed that certain amino acids may be substituted for other amino acids in a protein structure without appreciable loss of interactive binding capacity with complementary structures such as the gp120 binding regions found in CD4. It is thus hypothesized by the present inventors that various changes may be made in the sequence of gp120 binding ligands without appreciable loss of, and perhaps even improved, binding capacity.

The importance of the hydropathic index of amino acids in conferring interactive biologic function on a protein has been discussed generally by Kyte et al. (86), wherein it is found that certain amino acids may be substituted for other amino acids having a similar hydropathic index or core and still retain a similar biological activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules.

| Amino Acid | Hydropathic Index |
| --- | --- |
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

It is proposed that peptides having like binding characteristics can be prepared when the exchanged amino acids are within ±2, and more preferably, within ±1 unit of the base amino acid. Thus, for example, it is believed that isoleucine, which has a hydropathic index of ±4.5, can be substituted for valine (+4.2) or leucine (+3.8), and still obtain a protein having similar biologic activity. Alternatively, at the other end of the scale, lysine (−3.9) can be substituted for arginine (−4.5), and so on.

Accordingly, these amino acid substitutions are generally based on the relative similarity of R-group substituents, for example, in terms of size, electrophilic character, charge, and the like. In general, preferred substitutions which take various of the foregoing characteristics into consideration include the following:

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg; gln; glu |
| Met | leu; tyr |
| Ser | thr |
| Thr | ser |
| Trp | tyr |
| Tyr | trp; phe |
| Val | ile; leu |

For the purposes of the present invention, such alterations and modifications in the gp120 binding ligand, or for that matter in the toxin A chain portion of the conjugate, will be referred to as biologically functional equivalents of these structures. For the purposes herein, a "biological functional equivalent" will be considered a protein or peptide structure having a biological function that is similar in kind, but not necessarily in degree, to the parent molecule.

As noted, the preferred toxin moiety for use in connection with the invention is toxin A chain which has been treated to remove carbohydrate residues, so called deglycosylated A chain. The inventors have had the best success through the use of deglycosylated ricin A chains (dgA) which is now available commercially from Inland Laboratories, Austin, Tex.

However, as noted above, in that it will generally be desirable from a pharmacologic standpoint to employ the smallest peptide possible that nevertheless provides an appropriate biological response. One may thus desire to employ smaller A chain peptides which will provide an adequate anticellular response. To this end, it has been discovered by other that ricin A chain may be "truncated" by the removal of 30 N-terminal amino acids by Nagarase (Sigma), and still retain an adequate toxin activity (91). It is proposed that where desired, this truncated A chain may be employed in conjugates in accordance with the invention.

Alternatively, as with the gp120 binding ligand portion of the construct, one will find that the application of recombinant DNA technology to the toxin A chain moiety will provide additional significant benefits in accordance the invention. In that the cloning of ricin A chain has now been enabled through the publication of O'Hara et al. (69), it is now possible to identify and prepare smaller or otherwise variant peptides which nevertheless exhibit an appropriate toxin activity. Moreover, the fact that ricin A chain has now been cloned allows the application of site-directed mutagenesis, through which one can readily prepare and screen for A chain derived peptides, for example based on the "biological functional equivalency" discussed above, and obtain additional useful moieties for use in connection with the present invention.

The cross linking of the toxin A chain region of the conjugate with the binding ligand region is an important aspect of the invention. As discussed in the Summary section, where one desires a conjugate having biological activity, it is believed that a cross linker which presents a disulfide function is required. The reason for this in unclear, but is likely due to a need for the toxin moiety to be readily releasable from the binding ligand once the ligand has "delivered" the toxin to the targeted cells. Each type of cross linker, as well as how the cross linking is performed, will tend to vary the pharmacodynamics of the resultant conjugate. Ultimately, one desires to have a conjugate that will remain intact under conditions found everywhere in the body except the intended site of action, at which point it is desirable that the conjugate have good "release" characteristics. Therefore, the particular cross linking scheme, including in particular the particular cross linking reagent used and the structures that are cross linked, will be of some significance.

Cross-linking reagents are molecular bridges designed to tie together functional groups of two different proteins (e.g., toxins the binding ligand). To link two different proteins in a step-wise manner, heterobifunctional cross-linkers can be used which eliminate the unwanted homopolymer formation. An exemplary heterobifunctional cross-linker contains two reactive groups: one reacting with primary amine group (e.g., N-hydroxy succinamide) and the other reacting with a thiol group (e.g., pyridyl disulfide, maleinides, halogens, etc.). Through the primary amine reactive group the cross-linker may react with the lysine residue(s) of one protein (e.g., rCD4) and through the thiol reactive group, the cross-linker, already tied up to the first protein, reacts with the cysteine residue (free sulfhydryl group) of the other protein (e.g., dgA). The spacer arm between these two reactive groups of any cross-linkers may have various length and chemical composition. A longer spacer arm allows a better flexibility of the conjugate components while some peculiar components in the bridge (e.g., benzene group) may lend extra stability to the reactive group or an increased resistance of the chemical link to the action of various aspects (e.g., disulfide bond resistant to reducing agents).

The most preferred cross linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to its delivery to the site of action by the binding ligand. The SMPT ligand, as with many other known ligands, lends the ability to cross link functional groups such as the SH of cysteine or primary amines (e.g., the epsilon amino group of lysine). Another possible type of cross-linker includes the heterobifunctional photoreactive phenylatides containing a cleavable disulfide bond such as sulfosuccinimidyl-Z-(p-azido salicylamido) ethyl-1,3'-dithiopropionate. The N-hydroxy-succinimidyl rests with primary amino groups (as amide) and the phenylazide (upon photolysis) reacts non-selectively with any amino acid residue.

Although the "hindered" cross linkers will generally be preferred in the practice of the invention, non-hindered linkers can be employed and advantages in accordance herewith nevertheless realized. Other useful cross linkers, not considered to contain a protected disulfide, include SATA, SPDP and 2-iminothiolane (10). The use of such cross linkers is well understood in the art.

Of course, where one does not desire to employ the conjugate for its biological activity, the use of a cross linker which includes a disulfide function is not crucial. Exemplary cross linkers include the SMCC cross linker described hereinbelow. Numerous other possible non-disulfide bond containing cross-linkers are known and can be employed in accordance herewith. Such uses are envisioned, for example, where one may desire to make an antibody against the conjugate, and wants to ensure that the conjugate "immunogen" remains intact following vaccination of the animal used to make the antibody. Such anti-CD4-toxin conjugate antibodies will be useful in a variety of settings, including, for example, where one desires to screen for the presence of and/or measure the levels of conjugate in a selected sample, such as in a clinical sample from a patient being treated with the conjugate. Numerous methods are known for preparing antibodies, and it is believed that all such methods will prove suitable for the preparation of anti-conjugate antibodies in accordance herewith. Thus, the inventors contemplate that conjugates made in accordance herewith will find utility in embodiments other than therapeutic embodiments.

Once conjugated, it will be important to purify the conjugate so as to remove contaminants such as unconjugated A chain or binding ligand. It is important to remove unconjugated A chain because of the possibility of increased toxicity. Moreover, it is important to remove unconjugated binding ligand to avoid the possibility of competition for the binding site between conjugated and unconjugated species. In any event, a number of purification techniques are disclosed in the Examples below which have been found to provide conjugates to a sufficient degree of purity to render them clinically useful. In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates (71). The use of Blue-Sepharose combines the properties of ion exchange with A chain binding to provide good separation of conjugated from unconjugated binding.

The Blue-Sepharose allows the elimination of the free (non conjugated) binding ligand (e.g., rCD4) from the conjugate preparation. To eliminate the free (unconjugated) toxin (e.g., dgA) a molecular exclusion chromatography step is preferred using either conventional gel filtration procedure or high performance liquid chromatography.

After a sufficiently purified conjugate has been prepared, one will desire to prepare it into a pharmaceutical composition that may be administered parenterally. This is done by using for the last purification step a medium with a suitable pharmaceutical composition.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 1 to about 2 mg/ml with respect to the conjugate. Such formulations will typically include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility, non-immunogenicity and non-pyrogenicity. Such techniques are generally well known in the art as exemplified by reference 70. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biologics standards.

A preferred parenteral formulation of the rCD4-dgA conjugate is 1 to 2 mg conjugate/ml in 0.145M sodium chloride aqueous solution at pH 6–7. The preparations may be stored frozen at –10° C. to –70° C. for at least 1 year.

The examples which follow are included to demonstrate not only preferred embodiments such as processes, reagents, etc. for the practice of the invention, but also to demonstrate surprising or otherwise unexpected advantages of one or more aspects of the invention. It should be appreciated that the studies which follow were performed using techniques, assays, reagents, etc., which have been found by the inventors to work well in the practice of the respective embodiments. However, these studies are intended to be exemplary only, and numerous modification and changes will be apparent to those of skill in the art in light of these examples and the present disclosure.

EXAMPLE I

Preparation of Conjugates of Recombinant CD4 and Deglycosylated Ricin A Chain (rCD4-dgA)

Conjugates of human recombinant CD4 (rCD4) and deglycosylated ricin A chain (dgA) were prepared using three different cross-linkers [SATA, N-succinimidyl-S-thioacetate; SMCC,N-succinimidyl-(4-carboxy-cyclohexyl-methyl)-maleimide; and SMPT, N-succinimidyl-oxycarbonyl-alpha-methyl-alpha-(2-pyridyldithio (toluene)]. Conjugates prepared with two of the cross-linkers (i.e., SMPT and SATA) contained disulfide bonds (hindered vs unhindered, respectively) between the rCD4 and dgA. The third, SMCC, contained a thioether bond.

1. Recombinant CD4 (rCD4).

Recombinant CD4 (rCD4) containing amino acids 1 to 368 of the native protein was prepared as described by Smith et al. (61; see also 23–25). The absorption coefficient (A 1%, 1 cm/280 nm) and molecular mass used for rCD4 were 15 and 45 kDa, respectively. For use in certain biological studies discussed below, rCD4 was radiolabeled with Na[$^{125}$I] (Amersham, UK) using the IODO-GEN reagent (Pierce, Rockville, Ill.). The specific activity was approximately 1 uCi/ug. For other studies discussed below, rCD4 was also biotinylated with a 50-fold molar excess of the N-hydroxysuccinimide ester of biotin (Sigma, St. Louis, Mo.) (62).

2. Deglycosylated Ricin A Chain (dgA).

Deglycosylated ricin A chain (dgA) was purchased from Inland Laboratories (Austin, Tex.), and was prepared and characterized as described by Fulton et al. (63). The absorption coefficient and molecular mass of dgA are 7.7 and 32 kDa, respectively. Some dgA preparations were reduced with 5 mM dithiothreitol (DTT) (Sigma, St. Louis, Mo.) (final concentration) for 30 min. at room temperature in the dark. The DTT was removed by gel filtration on Sephadex G-25M equilibrated with 0.1M phosphate buffer containing 3 mM $NA_2$ EDTA, pH 7.5 (PBE). The reduced dgA was further treated with Ellman's reagent [5,5'-dithiobis(2-nitrobenzoic acid) (DTNB)] (Pierce, Rockville, Ill.) dissolved in dimethylformamide (DMF) (Pierce, Rockville, Ill.), at a final concentration of 2 mM for 30 min. at room temperature. The Ellmanized dgA was separated from the reaction mixture by gel filtration on Sephadex G-25M in PBE. The Ellmanized dgA was labeled with Na[$^{125}$I] using the IODO-GEN reagent as described by Fulton et at. (64) and the specific activity was approximately 1 uCi/ug.

dgA consists of two isomers, $dgA_1$ and $dgA_2$ (63). The separation of these isomers was accomplished using a Blue-Sepharose CL-4B column (Pharmacia, Piscataway, N.J.) (20×0.8 cm) equilibrated with 0.05 M PBE at pH 7.5. The bound $dgA_1+dgA_2$ proteins were eluted with a continuous NaCl gradient (up to 0.5M). Both $dgA_1$ and $dgA_2$ were eluted in two distinct chromatographic peaks; the last peak contained pure $dgA_1$.

3. Preparation of rCD4-dgA with the N-succinimidyl-S-thioacetate (SATA) Cross-liner.

1 ml of rCD4 dissolved in PBE, pH 7.5, at 4 mg/ml was mixed with 10 ul SATA (Calbiochem, La Jolla, Calif.) (65), dissolved in DMF at 4.7 mg/ml (molar ratio SATA/rCD4= 2.3) and the mixture was incubated at room temperature for 30 minutes. The derivatized rCD4 was separated from small molecules by gel filtration on Sephadex G-25M equilibrated with PBE. The thioacetylated rCD4 was deacetylated by treatment with 50 mM hydroxylamine (Sigma, St. Louis, Mo.) (final concentration) at pH 7.5 and immediately mixed with the Ellmanized dgA solution at pH 7.5 in a molar ratio of dgA/rCD4 of 2. The protein concentration of both dgA and thiolated rCD4 solutions ranged between 2–3 mg/ml. After an incubation of 2 hours at room temperature, the mixture was purified. In some experiments, one of the two proteins was labeled with Na[$^{125}$I].

4. Preparation of rCD4-dgA with the N-succinimidyl-oxycarbonyl-alpha-methyl-alpha-(2-pyridyldithio)toluene (SMPT) Cross-linker.

1 ml of rCD4 dissolved in PBE pH 7.5 at 4 mg/ml was mixed with 10 ul of SMPT (66) dissolved in DMF at 10 mg/ml (molar ratio SMPT/rCD4=2.9) and the mixture was incubated at room temperature for 30 min. The derivatized rCD4 was separated from small molecules by gel filtration on Sephadex G-25M, equilibrated with PBE and immediately mixed with freshly reduced dgA (non-Ellmanized) at pH 7.5 in a molar ratio of dgA/rCD4 of 2. The protein concentration of both reactants ranged between 1–2 mg/ml. After sterilization by passage through a 0.22 mu filter, the mixture was incubated at room temperature for 48 hours for purification. In some experiments, one of the two proteins was labeled with Na[$^{125}$I].

5. Preparation of rCD4-dgA with the N-succinimidyl-(4-carboxy-cyclohexyl-methyl)-maleimide) (SMCC) Cross-linker.

1 ml of rCD4 dissolved in PBE, pH 7.0 at 2 mg/ml was mixed with 10 ul of SMCC (Pierce, Rockville, Ill.) (67)

dissolved in DMF at 10 mg/ml (molar ratio SMCC/rCD4= 6.8) and the mixture was incubated at room temperature for 60 min. The derivatized rCD4 was separated from small molecules by gel filtration on Sephadex G-25M equilibrated with PBE, pH 6.0 and immediately mixed with freshly reduced dgA (non-Ellmanized) at pH 6.0 in a molar ratio of dgA/rCD4 of 2. The protein concentration of both reactants was 2 mg/ml. After one hour of incubation at room temperature and 16 hours at 4° C., the mixture was purified.

6. Preparation and Purification of Conjugates of Chicken Ovalbumin (OVA) and dgA.

Control conjugates comprising OVA (Sigma, St. Louis, Mo.) (molecular mass 43 kDa) and dgA were prepared with SATA or SMPT using procedures identical to those described for rCD4. The OVA-dgA mixtures were purified by chromatography on Blue-Sepharose-CL-4B and Con A-Sepharose-4B (Pharmacia, Piscataway, N.J.). The Con A-Sepharose-4B column (5×0.8 cm) was equilibrated with 0.02M Tris-HCl buffer with 1 mM $CaCl_2$, $MgCl_2$ and $MnCl_2$, pH 7.0 and the OVA-dgA conjugate was eluted with 0.25M alpha-methyl-D-mannoside in Tris-HCl buffer. These conjugates were used as controls in various assays, including the in vitro cytotoxicity assay.

7. Molar Ratios of rCD4/dgA.

The molar ratios of dgA chain to rCD4 were calculated from the specific radioactivities of $^{125}$I-dgA or of $^{125}$I-rCD4, respectively, and the following absorption coefficients: 7.7 for dgA, 15 for rCD4 and 12.0 for rCD4-dgA.

EXAMPLE II

Purification of rCD4-dgA Conjugates

For the purification of the crude conjugates, three methods were applied: a) Blue-Sepharose/Sephacryl S-200HR; b) Blue Sepharose/Sepharose-rgp120; and c) gel permeation by HPLC on TSK 3000 columns.

These individual procedures were conducted as follows:

1. Chromatography on Blue-Sepharose CL-4B Columns.

A column of 20×0.8 cm containing 10 ml of gel with a binding capacity of 20 mg of dgA was used to purify the rCD4-dgA. The column was equilibrated with 0.05M PBE and eluted with a continuous NaCl gradient (up to 0.5M) using a Pharmacia gradient maker filled with 50 ml of 0.05M PBE and 0.5M NaCl, respectively.

2. Affinity Chromatography on Sepharose-rgp120.

The recombinant form of the viral envelope glycoprotein gp120 (rgp120) (Genentech, Inc., South San Francisco, Calif.) was coupled to activated CH-Sepharose-4B (Pharmacia, Piscataway, N.J.) according to the manufacturer's protocol, at a final concentration of 0.8 mg rgp120 /ml packed gel. The Sepharose-rgp120 bound 0.125 mg rCD4/ mg rgp120. The rCD4 and rCD4-dgA conjugates bound to a Sepharose-rgp120 column (4×1.8 cm) were eluted with 0.1M glycine buffer containing 0.15M NaCl at pH 3.0.

3. Gel Permeation High Performance Liquid Chromatography (HPLC).

Samples were applied either to an analytical 7.5×600 mm TSK 3000SW column (Sepherogel, LKB, Bromma, Sweden) or to a preparative 21.5×600 mm TSK G3000SWG column (Ultropac, LKB, Bromma, Sweden) and separation was performed in PBE, pH 7.5, at a flow rate of 1 ml/min (Spherogel) and 3 ml/min (Ultropac). The retention times for the peaks were compared to those of standard protein of known molecular weight (Pharmacia, Piscataway, N.J.).

4. Gel Filtration on Sephacryl S-200HR.

Gel filtration was performed on a 80×1.8 cm column equilibrated with PBE. The column was calibrated with mouse F(ab')2 (100 kDA), rCD4 (45 kDa) and dgA (32 kDa).

5. Molecular Mass and Composition of the rCD4-dgA Conjugates.

Figure 1A:
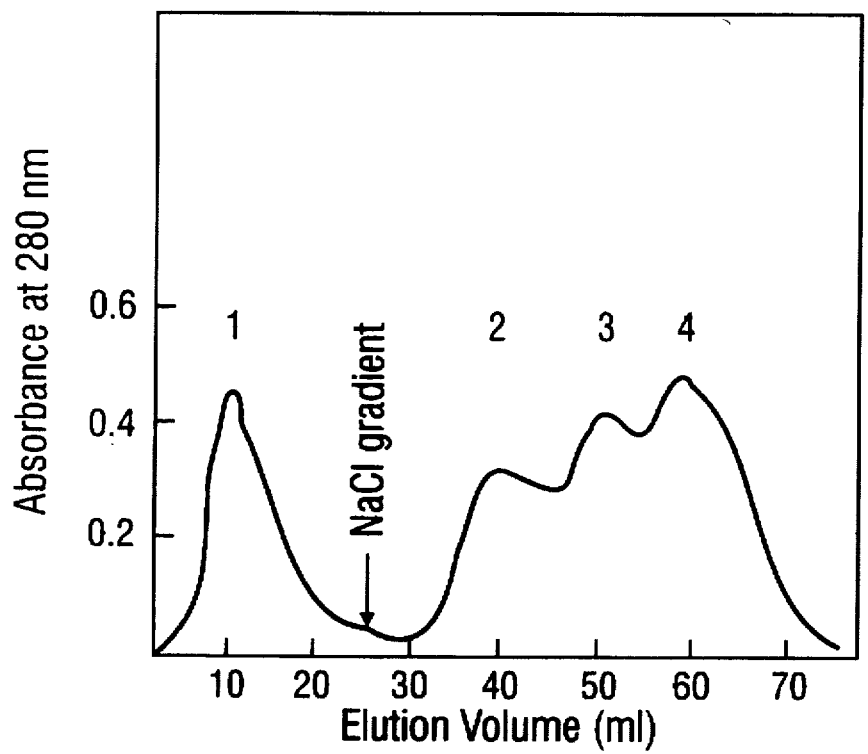
FIG. 1. Purification of rCD4-dgA conjugates.
a) Blue Sepharose CL-4B (SMPT-derived conjugate)
  1) rCD4; 2) dgA$_2$; 3) rCD4-dgA; 4) dgA$_1$
b) Sephacryl S-200HR (SATA-derived conjugate)
  1) aggregated rCD4-dgA; 2) rCD4-dgA (molecular mass 80 kDa); 3) dgA
c) Sepharose-rgp120 (SMPT-derived conjugate)
  1) non-bound (dgA); 2) bound and eluted at pH 3.0 (rCD4-dgA).
d) TSK 3000SW (SMPT-derived conjugate)
  1) aggregated rCD4-dgA; 2) rCD4-dgA (molecular mass 82 Kda); 3) rCD4; 4) dgA.
Figure 1B:
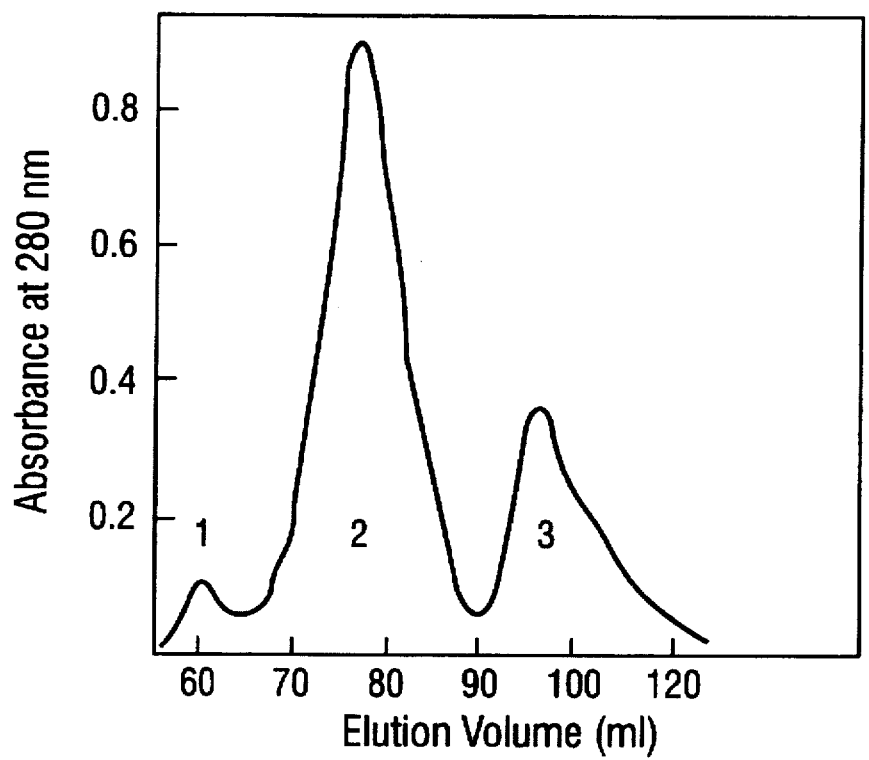
Figure 1C:
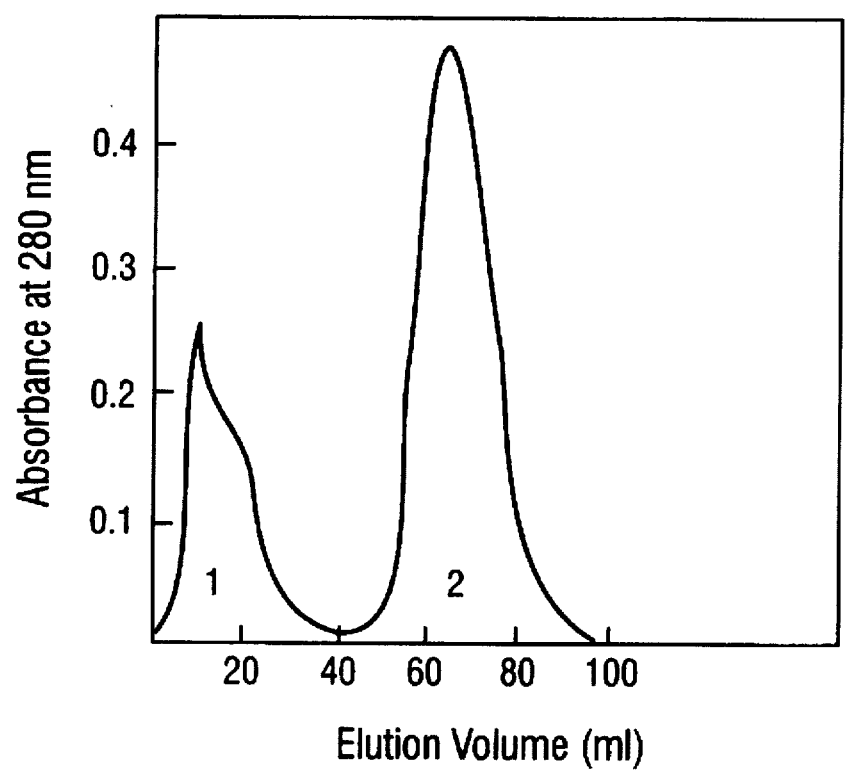
Figure 1D:
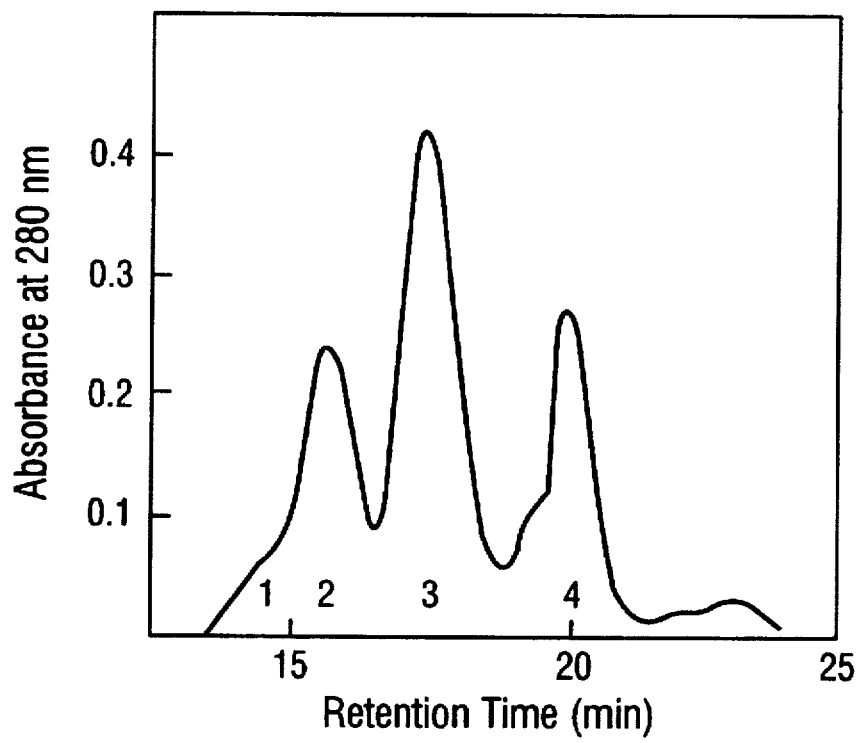
Figure 2:
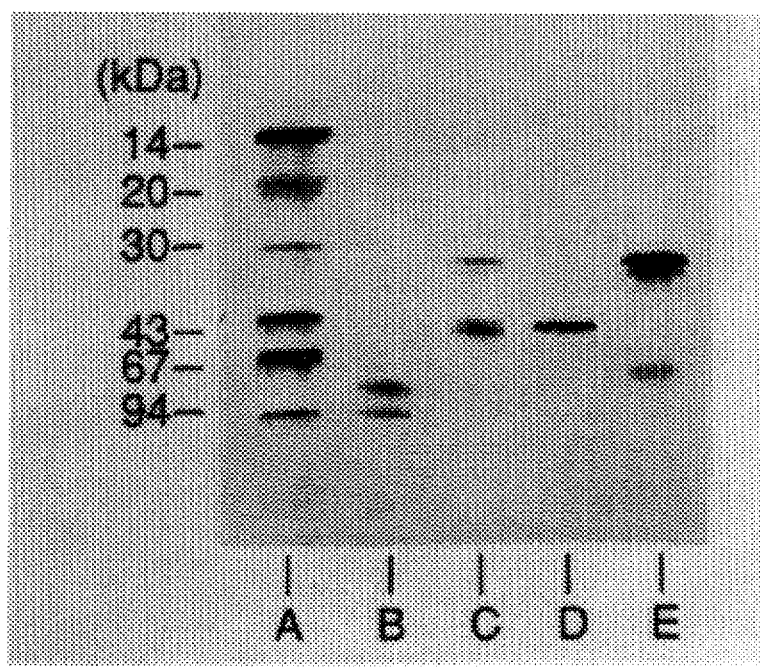
FIG. 2. SDS-PAGE of rCD4-dgA and its protein component. a) Molecular weight standard; b) rCD4-dgA prepared with SMPT (or SATA) from dgA or dgA$_1$; c) rCD4-dgA reduced with 5% 2-mercaptoethanol; d) rCD4-derivatized with SMPT (or SATA; e) dgA.

Irrespective of the cross-linker used to construct the conjugates, the final purified preparations had a rCD4/dgA ratio of approximately 1.0 (see Table 1 below) and molecular mass of 80–82 kDa as determined by gel filtration of Sephacryl S-200HR and HPLC. By SDS-PAGE analysis under nonreducing conditions, however, two electrophoretic bands of 75 kDa and 92 kDa were observed (FIG. 2). The presence of rCD4 and dgA in each of the two electrophoretic bands was confirmed by electrophoresing rCD4-SMPT-dgA labeled either in the rCD4 or the dgA moiety with [$^{125}$I] and preparing autoradiographs of the gels. Both electrophoretic species (75 kDa and 92 kDa) were labeled irrespective of which moiety was labeled. Both electrophoretic bands contained biologically active rCD4 since both bands specifically bound to Sepharose-rgp120 and eluted at pH 3.0 (FIG. 1c).

Figure 3A:
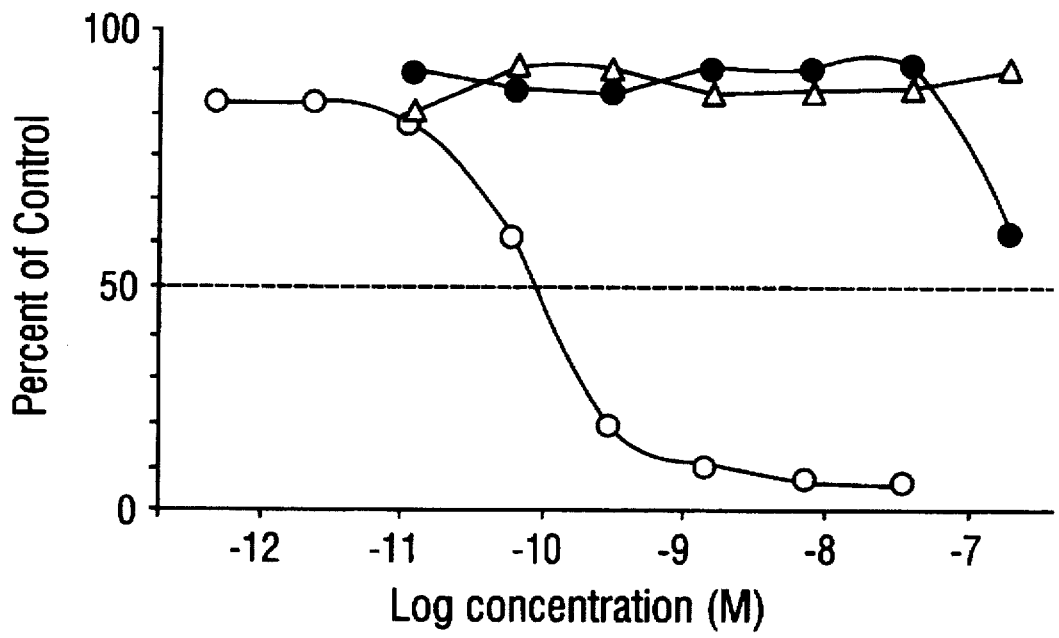
FIG. 3. The rCD4-dgA conjugate is toxic to HIV-infected H9 cells;
A) The human T cell line H9 chronically infected with HIV-1 (one representative experiment of four);
B) Uninfected H9 cells (one representative experiment of four).

One explanation for the existence of two forms of the rCD4-dgA is that one species contained one molecule of dgA/molecule of rCD4 (75 kDa) and the other two molecules of dgA/molecule of rCD4 (105 kDa). However, this explanation is considered unlikely based on the lack of concordance between the measured (92 kDa) and calculated (105 kDa) molecular mass of the slower electrophoretic band and, more importantly, because the ratio of dgA to rCD4 in both bands was 0.98±0.02. Another possible explanation for the existence of the protein doublet was that one species contained rCD4-dgA$_1$ (slow band) and the other rCD4-dgA$_2$ (fast band). However, this explanation was shown not to be the case by the finding that rCD4-SMPT-dgA prepared with purified dgA$_1$ also contained the same electrophoretic doublet (FIG. 3, land B). The most likely explanation is that there are two different sites on rCD4 which can be conjugated to dgA, leading to the formation of two types of conjugates which have different molecular shapes and Stokes radii and run at different rates on SDS-polyacrylamide gels. Under reducing conditions, rCD4-dgA prepared with either SMPT or SATA, yielded two bands corresponding to rCD4 and dgA. The SMCC-derived conjugate was not reduced and maintained its unmodified electrophoretic doublet.

6. Sodium Dodecyl Sulfate Polyacrylamide Gel Electrophoresis (SDS-PAGE).

rCD4, and rCD4-dgA conjugates were analyzed under both reducing and nonreducing conditions by SDS-PAGE using the Pharmacia Phast system with 8–25% gel gradient. The gels were stained with either 0.1% Phast gel blue R or with 0.4% silver nitrate according to the manufacturer's directions. The proportion of radioactivity present in the electrophoretic bands was determined by scanning densitometry of the autoradiograph following SDS-PAGE using a Bio-Rad (Model 620) videodensitometer (64). The following proteins were used as standards for the estimation of molecular weight (Pharmacia, Piscataway, N.J.): alpha-lactalbumin (24.4) kDa), soybean trypsin inhibitor (20.1 kDa, carbonic anhydrase (30 kDa), OVA (43 kDa), bovine serum albumin (67 kDa) and phosphorylase b (94 kDa).

7. Determination of Sulfhydryl Groups.

The number of SH groups introduced into rCD4 as well as the number of free SH groups in the rCD4-dgA conjugates were determined with DTNB (79).

8. Results.

By gradient chromatography on Blue Sepharose (which binds dgA), the majority of the rCD4 was removed from the rCD4-dgA conjugate (rCD4 does not bind to Blue Sepharose) (FIG. 1). Irrespective of the cross-linker used for its preparation, the rCD4-dgA always eluted in the third peak and was flanked by $dgA_1$ and $dgA_2$ (FIG. 1a). Most of the heavy molecular weight rCD4-dgA conjugates (molecular mass about 100 kDa) were tightly bound to the Blue-Sepharose and therefore could only be eluted by a mixture of 0.05M NaOH and 0.5M NaCl. Residual dgA remaining in the rCD4-dgA preparations after Blue-Sepharose chromatography could be removed either by gel filtration on Sephacryl S-200HR (FIG. 1b) or by affinity chromatography on Sepharose-rgp120 (FIG. 1c).

As shown by the chromatographic profiles (FIG. 1b), gel filtration resulted in more extensive purification since some high molecular weight material could be further separated from the conjugate which has an apparent molecular mass of 80 kDa. A partial purification (80% purity) can be achieved by a single step purification procedure using HPLC with Spherogel TSK 3000SW column (FIG. 1d) or Ultropac TSK G3000SWG column. If the HPLC separation was applied after the Blue-Sepharose chromatography, the rCD4-dgA conjugates have better purity than by using Sephacryl S-200HR since the TSK 3000SW columns facilitate the separation of rCD4-dgA from the rCD4. The yields and purity of the rCD4-dgA conjugates are presented in Table 1.

TABLE I

COMPARISON BETWEEN SATA-, SMPT- AND SMCC-DERIVED rCD4-dgA CONJUGATES

| PARAMETER | SATA | SMPT | SMCC |
|---|---|---|---|
| Yield (%)[a] | 19.5 | 17.5 | 20.8 |
| Purity (%)[b] | 90.0 | 90.0 | 80.0 |
| Molecular composition | | | |
| (dgA/rCD4 ratio) | 1.0 | 1.25±0.15 | ND |
| Affinity for gp120 ($\times 10^{-9}$M)[c] | 4.4 ±0.5 | 4.9 ±0.2 | ND |
| Stability in vitro (%)[d] | 53.0 ±7.0 | 36.0 ±6.0 | ND |
| Stability in vivo (%)[e] | 18.6 | 4.4 | 1.0 |
| Half-Life (min)[f] | | | |
| alpha-phase | 45.0 ±10.0[g] | 60.0 ±11.0[g] | 40.0[h] |
| beta-phase | 177.0 ±24.0 | 209.0 +21.0[g] | 225.0[h] |
| $LD_{50}$ (ug/g mouse)[i] | 100.0 | 116.0 ±25.9 | ND |
| Inhibition of protein synthesis ($IC_{50}$) ($\times 10^{-11}$M)[j] | 1.6 | 1.2 | >1000 |
| Cytotoxicity of HIV-infected H9 cells ($IC_{50}$) ($\times 10^{-10}$M) | 1.7 ±1.0[k] | 2.0 ±1.0[l] | >5000 |

[a]The amount of rCD4 in the conjugates (60% of the total protein) is expressed as percentage of the initial amount of rCD4 used for preparation. Mean of 4 experiments.
[b]After Blue-Sepharose CL-4B and Sephacryl S-200HR. Calculated by densitometry of silver stained SDS-Page (nonreduced).
[c]The affinity of rCD4 for gp120 was 4.1 + 0.5 × $10^{-9}$M (mean of 3 experiments).
[d]Cytoxic activity after 16 hours incubation at 37° C., The $IC_{50}$ of freshly thawed conjugate, used in the same assay was taken as 100%. Mean of 3 experiments.
[e]Percentage of free dgA chain released at 4 hours after injection of the radiolabeled conjugate.
[f]The alpha-phase is the first 30 minutes and the beta-phase is the next 8 hours. For dgA, alpha = 20 min.; beta = 228 min. For rCD4, alpha = 10 min.; beta = 105 min.
[g]Mean of 3 experiments.
[h]Mean of 2 experiments.
[i]The $LD_{50}$ of dgA was 30 ug/g mouse.
[j]Mean of 3 experiments.
[k]Mean of 5 experiments.
[l]Mean of 8 experiments.

9. Comments

Conjugates utilizing three different linkers were constructed and compared for their yield, purity, biochemical structure, in vitro activity and in vivo behavior. Two of the conjugates were constructed with a disulfide bond between the rCD4 and dgA using the SATA or SMPT cross-linkers; the third was constructed with a thioether bond, utilizing SMCC. The three cross-linkers derivatize the E-amino groups on the rCD4 and utilize the natural SH of the cysteine of the dgA. For all three conjugates, the active group(s) were introduced by N-hydroxysuccinimide to establish an amide bond between the primary amino group(s) of rCD4 and the active pyridyl disulfide group.

Biochemical analysis of the conjugates was performed and the results indicate that they were similar in size and content of rCD4 and dgA. Hence:

a) The three conjugates contained one molecule of rCD4 covalently linked to one molecule of dgA. The conjugates had apparent molecular masses of 80–82 Kda as determined by gel filtration and HPLC, but when analyzed by SDS-PAGE, consisted of two forms of 75 and 92 kDa. The 75 and 92 kDa species each contained a single rCD4 and a single dgA. The possibility that the doublet represented two rCD4-dgA conjugates with different amounts or types of dgA ($dgA_1$ and $dgA_2$) was excluded by appropriate experiments. This heteroclitic structure might be generated if the derivatized rCD4 contains two different populations of molecules. However, no heterogeneity of the rCD4 preparations was demonstrated by any technique including isoelectric focusing suggesting that there are no significant differences in the distribution of the electric charges on the rCD4 molecules.

b) As determined by reduction and analysis of the two disulfide-linked conjugates in a cell-free rabbit reticulocyte lysate assay, the dgA chains in the conjugates prepared with SATA and SMPT were as active as the dgA used to prepare them.

c) Utilizing several different methods of purification, the final yield of each conjugate was approximately 20% and all three conjugates retained their rgp120-binding activity. The purification of rCD4-dgA conjugates involved chromatography on Blue-Sepharose, a chromatographic material previously used for the purification of ricin A chain-containing immunotoxins (71). This basic technique was modified in part by using longer columns and applying a salt gradient with the aim of exploiting the ion exchange property of Blue-Sepharose at pH 7.5. The combined properties of ion exchange and dgA-binding allowed the separation of rCD4-dgA conjugates in reasonable yield and with an acceptable degree of purity.

A subsequent gel filtration on Sephacryl S-200HR or affinity chromatography on Sepharose-rgp120, yielded rCD4-dgA preparations that were approximately 90% pure with traces of free dgA and rCD4 and some heavy molecular mass material. The greatest purity of the rCD4-SMPT-dgA conjugate (>95%) was achieved by combining Blue-Sepharose chromatography with HPLC on TSK G3000SWG.

EXAMPLE III

Treatment of HIV-Infected Cells By rCD4-Ricin A Chain

Thiolated rCD4 [derivatized with N-succinimidyl-S-acetyl thioacetate (SATA) (72) was coupled to dgA derivatized with Ellman's reagent (74) in a manner similar to that described above in Example I. The conjugate was purified by gel filtration on Sephacryl S-200 (HR) to remove free dgA and on a column of Sepharose anti-ricin A chain to remove free rCD4.

The activities of the dgA and rCD4 components of the conjugate were evaluated. After reduction with dithiothreitol, the dgA released from the conjugate was comparable to native or Ellmanized dgA in its ability to inhibit protein synthesis in a cell-free rabbit reticulocyte assay (74). [$IC_{50}$ (12)=$4\times10^{-11}$M versus $2\times10^{-11}$M]. The rCD4-dgA had gp120 binding activity comparable to that of thiolated rCD4 and 25 to 50% that of native rCD4 in a solution or solid-phase binding assay (75).

Figure 3B:
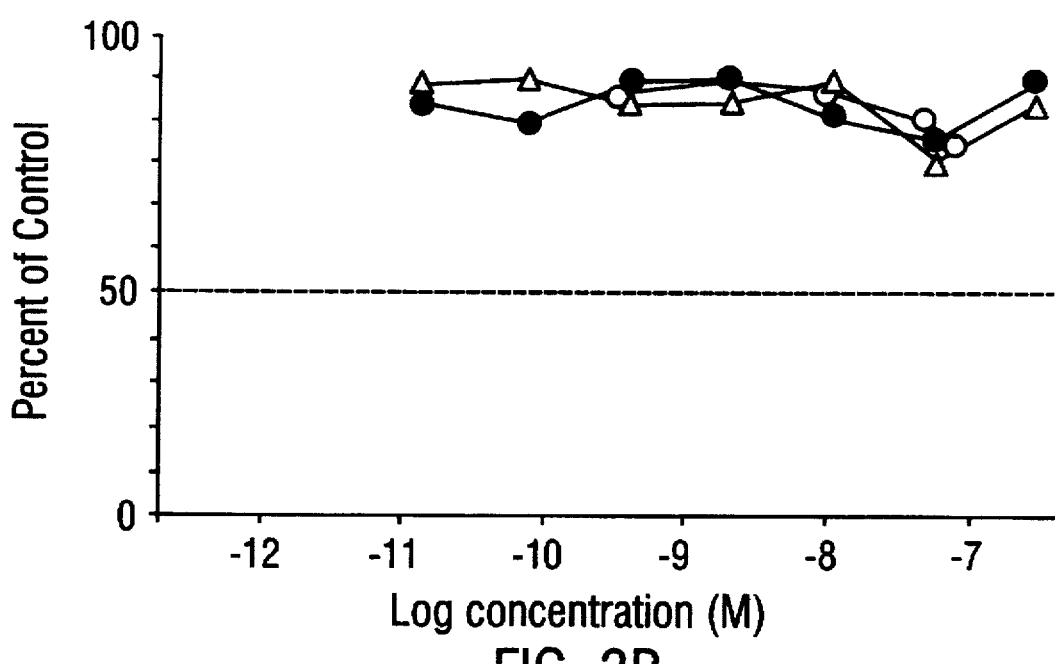

Treatment of HIV-infected cells from the human T cell line H9 with rCD4-dgA inhibited DNA synthesis by >90% with an $IC_{50}$ of $1.5\pm0.53\times10^{-10}$M (mean±SD of four experiments) (FIG. 3). In contrast, free rCD4 or an irrelevant antibody-ricin A chain conjugate of the same size [Fab'-MOPC-21 ($IgG_1$-dgA were only 1/1000 as effective ($IC_{50}$>$10^{-7}$M). Neither rCD4-dgA, rCD4, nor Fab'-MOPC-21-dgA killed uninfected H9 cells at a concentration of >$5\times10^{-8}$M (FIG. 3B). Hence, the toxicity of rCD4-dgA was specific.

The cytotoxic effect of the rCD4-dgA could be effectively blocked in a concentration-dependent manner by soluble rgp120 (FIG. 4A), by monoclonal antibodies (MAbs) to the gp120 binding site of CD4 [Leu-3a (14)] (FIG. 4B), or by soluble rCD4 (FIG. 4C). In contrast, bovine serum albumin (BSA) (FIG. 4, A and C) or MAbs to another CD4 epitope not involved in gp120 binding (79) did not inhibit the cytotoxicity of rCD4-dgA (FIG. 4). Thus, the toxicity of rCD4-dgA to HIV-infected H9 cells occurred by specific binding of the rCD4 component of the conjugate to gp120.

It was next determined whether rCD4-dgA could kill cells expressing major histocompatability epitopes (Mean±SD of three experiments) (FIG. 5). The inability of rCD4-dgA to kill Daudi cells at concentrations >$5\times10^{-8}$M may be due to a lower binding affinity of rCD4-dgA to class II molecules or to the inability of class II antigens to be internalized after binding rCD4-dgA.

EXAMPLE IV

Pharmacology and Biological Properties of rCD4-dgA Conjugates

1. Cytotoxicity of CD4-dgA Conjugates for HIV-infected and Uninfected Cells

An assay measuring the cytotoxicity of rCD4-dgA to HIV-infected human H9 cells was performed generally as follows:

Serial dilutions of conjugates were plated in triplicate in 96 well microtiter plates in complete medium (RPMI, 12% FCS and antibiotics). Cells were then added to a final concentration of $4\times10^5$ cells/ml and the plates were incubated for 36 hours at 37° C. (5% $CO_2$). Cells were then pulsed for 6-8 hours with 1 uCi of [$^3$H]thymidine and harvested on a titertek automatic harvester. [$^3$H]thymidine incorporation was determined on an LKB Beta counter. Results are expressed as a percentage of control (untreated cells). Three separate experiments were performed each using infected and uninfected human H9 cells.

In agreement with the studies set forth in Example IV using the SATA-linked conjugate, both the rCD4-SMPT-dgA and rCD4-SATA-dgA were equally toxic to HIV-infected H9 cells in vitro (FIG. 7 and Table 1). The rCD4-SMCC-dgA was no more toxic than the control conjugate, OVA-dgA (Table I) containing suggestions that conjugates of antibodies and A chain may only be toxic when a disulfide bond is present between the two components (81). Importantly, none of the conjugates was toxic to uninfected H9 cells.

The results of the cytotoxicity studies indicate that rCD4-dgA prepared with either SMPT or SATA killed HIV-infected H9 cells with identical potency ($IC_{50}$=1.7–2.0$\times10^{-10}$M). The rCD4-SMCC-dgA was no more toxic than an irrelevant conjugate (OVA-dgA) ($5\times10^{-8}$M) despite the fact that it displayed gp120-binding activity. The two active conjugates were 1000-fold more toxic to HIV-infected cells than to uninfected cells and the control conjugates, OVA-dgA, was not toxic to either infected or uninfected cells.

2. Binding of rCD4 and derivatives to rgp120

The binding of rCD4, SATA or SMPT conjugates to rgp120 was determined through the application of an automated liquid phase competitive binding assay. The assay utilized a Pandex Screen instrument (Pandex Laboratories, Inc.) for the evaluation of solution phase binding of rgp120 to rCD4, and was performed using 0.03 ml per well of rCD4 or conjugates of rCD4 titered in a separate 96-well plate from 50 to 2 ug/ml in PBS pH 7.5, 1% BSA, 0.02% azide (PBSA). 0.03 ml of rCD4-biotin at a concentration of 9 ug/ml in PBSA was added followed by 0.03 ml of rgp120 at a concentration of 15 ug/ml in PBSA. The reaction mixture was incubated for 3 hours at room temperature with mixing. Free and bound rgp120 were immunoprecipitated from the reaction mixture with anti-rgp120 monoclonal antibodies (MoAbs) absorbed to polystyrene beads. For the immunoprecipitation, 0.02 ml of these anti-rgp120 MoAb-coated beads were first added to a Pandex plate by the instrument. 0.03 ml of the reaction mixture was then transferred to the particles in the Pandex plate. Following a 15 minute incubation, 0.02 ml of a streptavidin-phycoerytrin conjugate was added at a 1/50 dilution in PBSA. The plate was incubated in the dark for 15 minutes then washed with PBS, 0.05% Tween 20 and the fluorescence intensity was determined.

The inhibition curves of rCD4 and the SATA and SMPT conjugates are illustrated in FIG. 6. Although these curves are displaced slightly from one another, differences between curves are not statistically significant. These data also were used to calculate binding affinities (Kd) of rCD4 and the conjugates by Scatchard analysis using the software provided with the instrument (80). These results indicate that there is a small loss in affinity due to conjugation with SMPT, although this difference was within experimental error (See Table I).

3. Binding of rCD4 to Daudi Cells.

The binding of rCD4 to Daudi cells was evaluated by a direct binding assay using radiolabeled rCD4 or by an indirect assay with biotinylated rCD4 and fluorescein-avidin. Cells ($10^6$/0.1 ml) were treated with various amounts of $^{125}$I-rCD4 (1–500 ng/0.1 ml) or biotinylated rCD4 (0.1–25 ug/0.1 ml) for 3 hrs or 30 min., respectively, at 4° C. After washing twice with cold phosphate-buffered saline (PBS) containing 10% fetal calf serum (FCS) and 0.1% sodium azide, the radioactivity of the cell pellet was measured (when radiolabeled rCD4 was used) or the cell suspension was treated with fluorescein-avidin (Pierce, Rockville, N.J.) (1–5 ug/0.1 ml) for 15 min. in ice. The cells were washed and analyzed on a fluorescence-activated cell sorter FACS (Becton-Dickinson, Oxnard, Calif.).

No significant binding of $^{125}$I-labeled or biotinylated rCD4 to MHC class II$^+$ human Daudi cells was observed (K>$10^4$ $M^{-1}$). This indicates that neither rCD4 nor rCD4-dgA can bind to the cell surface MHC class II antigens (82). As determined by binding analyses, the rCD4 molecule and the conjugates prepared with it, did not bind to class II$^+$ Daudi cells. Since class II molecules re the putative natural ligand for CD4, this demonstrates that while cell-bound CD4 can bind to cell-bound class II antigens (82), soluble rCD4 does not bind to cell-bound class II molecules. This finding is consistent with the studies shown in Example III in that rCD4-SATA-dgA does not kill Daudi cells even though an anti-class II-dgA conjugate was toxic in the same assay.

4. Stability of the rCD4-dgA Conjugates.

The stability of the SATA- and SMPT-derived rCD4-dgA conjugates was tested by incubating the conjugates in fresh human plasma for 16 hours at 37° C. prior to performing toxicity tests on HIV-infected human H cells.

As shown in Table I above, the cytotoxicity of both conjugates was reduced approximately 50% by incubation in human plasma at 37° C. for 16 hours. The difference between the remaining cytotoxicity of SATA- and SMPT-derived conjugates is not statistically significant.

The dissociation of the rCD4-dgA conjugates in vivo was further studied by measuring the release of free dgA at 4 hours after injection of the radiolabeled conjugate into normal mice. It should be noted that the mouse cells do not bind rCD4-dgA and, hence, represent a good model for conjugate stability in a model where the conjugate is not specifically taken up by cells in vivo. Hence, following injection of rCD4-dgA, serum samples were collected and immunoprecipitated with rabbit anti-ricin A chain. Precipitates were analyzed by SDS-PAGE and autoradiography (see Methods). The results show that the rCD4-SMPT-dgA broke down in vivo four times more slowly than the rCD4-SATA-dgA (Table 1) and that the rCD4-SMCC-dgA was the most stable (less than 1% released dgA).

When tested in a cytotoxicity assay on HIV-infected H9 cells, the plasma of mice collected 3 hours (one half-life period) after injecting radiolabeled SATA-or SMPT-linked conjugates showed $IC_{50}$'s identical to those of freshly thawed conjugates ($2 \times 10^{-10}$M).

The stability studies were performed as follows: Radiolabeled conjugates (approximately $10^7$ cpm/animal) were injected into mice and after 4 hours the animals were exsanguinated and the heparinized blood was collected. The free and conjugated dgA in plasma were precipitated with an immuno-complexes prepared with rabbit anti-ricin A chain and goat anti-rabbit Ig (83). The precipitate was boiled in 1% SDS and electrophoresed on 12% SDS-PAGE. Autoradiograms of the dried gels were scanned by using a Bio-Rad video-densitometer. The areas under the dgA and rCD4-dgA peaks were divided by the total area under both peaks to determine the percentage of radioactivity that corresponds to the released dgA. This value was used as a means of evaluating the in vivo splitting of the rCD4-dgA conjugates.

The functional activity of rCD4-dgA conjugates recovered from blood was determined by performing a cytotoxicity assay on HIV-infected H9 cells. Mice were injected with radiolabeled SATA- or SMPT-linked conjugates with known specific radioactivity (approximately $5 \times 10^4$ cpm/ug). After 3 hours, the animals were exsanguinated and the heparinized plasma containing a known amount of conjugate was compared in the in vitro cytotoxic assay to freshly thawed conjugates.

To determine stability in human plasma, conjugates were incubated at 50 ug/ml with undiluted fresh human plasma or PBS for 16 hours at 37° C. and then used in the cytotoxicity assay in parallel with freshly thawed conjugates.

The in vitro stability tests indicated that both the SATA- and SMPT-derived rCD4-dgA conjugates have similar chemical stability and that both lose approximately 50% of their cytotoxic potency after 16 hours at 37° C. However, in vivo (in mouse blood), the SMPT-linked conjugate was more stable than the SATA-linked conjugate releasing four times less free dgA. This result is in agreement with a report by Thorpe, et al. (85) who showed that an immunotoxin prepared with SMPT broke down in vivo six times more slowly than the corresponding immunotoxin prepared with 2-iminothiolane, a cross-linker which produces an unhindered disulfide bond as does SATA. SMPT generates a disulfide bond which is sterically hindered by the adjacent benzene ring and methyl groups which protect the disulfide bond from the attack of thiolate anions such as glutathione which can be present in tissues and blood.

As determined by injecting the SATA- and SMPT-linked conjugates into mice and utilizing their sera 3 hours later to kill HIV-infected H9 cells in vitro, there was no loss in activity of the remaining conjugate. This result indicates that both rCD4-dgA conjugates should maintain their cytotoxic activity for a period of time long enough to allow their reaction with circulating infecting cells.

5. In Vivo Elimination of rCD4-dgA Conjugates.

The procedure of Fulton et al. was used (64). Briefly, the conjugates were labeled with $Na[^{125}I]$ by the IODO-GEN technique and were injected into the retro-orbital sinus of mice (approximately $4 \times 10^6$ cpm/5 ug/animal). The $[^{125}I]$ levels were determined in heparinized samples (75 ul) of blood at 5 min., 10 min., 30 min., 1 hour, 2 hours, 4 hours, and 8 hours. The total radioactivity remaining in the blood was determined by counting aliquots in a gamma counter and assuming a total blood volume of 7% of body weight (64). Acid-precipitable radioactivity was determined by precipitation of plasma aliquots with 10% trichloroacetic acid. The percentage of the injected radioactivity remaining in the circulation was calculated as the percentage of acid-precipitable radioactivity injected. The half-lives ($T_{1/12}$) for both the alpha- (30 min.) and beta-phase (8 hours) of clearance were determined graphically by extrapolation to zero of the percentage of acid precipitable radioactivity vs time curves (84).

Plasma levels of radiolabeled rCD4-dgA injected into mice showed two major phases for elimination, namely, a rapid initial alpha phase which approached completion within 30 min. and a slower beta phase. Approximately 90% of all three conjugates were cleared in 8 hours (FIG. 8). There was no statistically significant differences between the $T_{1/2}$beta of the three conjugates. However, the SMPT-derived rCD4-dgA has a slightly longer half-life than the SATA-derived conjugate (Table I). This difference was not as great as would have been predicted from earlier studies using SMPT conjugates prepared with IgG and dgA (85). It should be noted that the half-life of rCD4 increases markedly in both phases (from 2–5-fold) after conjugation with dgA.

The organ distribution of radioiodinated proteins was determined following perfusion of anesthetized mice with PBS as previously described (64). Organs were removed, weighed and counted in a gamma counter. A sample of the organs was minced with scissors, extracted with 0.5% Nonidet P-40 and the clarified extract was precipitated with 10% trichloroacetic acid. The percentages of acid precipitable radioactivity were determined and the values were used to calculate the protein-bound radioactivity in various tissues. The capacity of the organ to accumulate the radiolabeled proteins was calculated by dividing the percent of the injected radioactive dose retained in the organ by net weight (g) of the organ.

The tissue distribution of the labeled conjugates as determined by acid precipitability of extracts of various organs 1 hour after infection of radiolabeled conjugates or their protein components is presented in Table II. From the results summarized in this Table, the following conclusions could be drawn: a) the rCD4-SMPT-dgA and the rCD4-SMCC-dgA conjugates preferentially accumulated in the spleen at levels that were 3-fold higher than those of the rCD4-SATA-dgA; b) the rCD4-SMCC-dgA concentrated in liver reaching levels approximately 3 times higher than the SATA-linked conjugates; c) the rCD4-SATA-dgA conjugate showed lower accumulation in these organs (liver and spleen) than the other two conjugates but accumulated in the kidneys.

(85), the rCD4-dgA conjugates are 6-fold less toxic on a protein basis and 10-fold less toxic on a dgA basis.

7. Lesion Distribution of rCD4-dgA Conjugates.

Treatment groups consisted of four 25–32 g $CAF_1$ male mice which were inoculated intraperitoneally with a one ml solution containing 5%, 10% and 20% of the $LD_{50}$ of either SMPT-linked rCD4-dgA, SATA-linked rCD4-dgA, 20% of the $LD_{50}$ of dgA, or saline. Mice were sacrificed after 7 days by intraperitoneal injection of pentobarbital. Tissues were examined grossly and fixed in 10% buffered formalin. Liver, spleen, kidneys, lung, heart, brain appendicular and diaphragmatic muscle were embedded in paraffin, sectioned at 5 microns and stained with hematoxylin and eosin. Lesions

TABLE II

RETENTION OF ACID PRECIPITABLE RADIOACTIVITY
IN VARIOUS ORGANS OF MICE INJECTED WITH
rCD-dgA CONJUGATES AND THEIR COMPONENTS, rCD4 and dgA*

Percent of injected acid-precipitable radioactivity retained per gram of organ (wet weight) 1 hour after injection of:

| Organ | rCD4-SATA-dgA | rCD4-SMPT-dgA | rCD4-SMCC-dgA | rCD4 | dgA |
|---|---|---|---|---|---|
| Kidneys | 8.9 | 6.4 | 7.9 | 10.5 | 8.4. |
| Liver | 3.7 | 5.4 | 10.8 | 1.6 | 1.8 |
| Spleen | 2.8 | 8.9 | 7.8 | 1.1 | 1.7 |

*Mean of two separate experiments.

In the mouse in vivo studies, the SMCC-linked conjugate served as a control, i.e., a conjugate lacking a disulfide bond which might be susceptible to thiolmediated reduction. The in vivo clearance studies demonstrated that rCD4 was readily cleared with a $T_{1/2}$alpha of 10 minutes. Only 7% remained in the serum at 30 minutes. dgA also had a short $T_{1/2}$alpha of 20 minutes. At 30 minutes, 26% remained in the serum. In contrast, the rCD4-dgA conjugates had significantly longer $T_{1/2}$alphas (40–60 minutes). At 30 minutes, more than 40% remaining in serum. Thus, the coupling of rCD4 to dgA gives the rCD4 a significantly longer serum half-life. For all three conjugates, the percentage of protein remaining in the circulation after 8 hours was slightly under 10%. At this time, virtually all the rCD4 was cleared. The difference between the 8 hour bets-phase half-life of the SATA-linked (177 minutes) and SMPT-linked (209 minutes) conjugates is not statistically significant.

6. Toxicity of rCD4-dgA Conjugates.

The capacity of various rCD4-dgA conjugates to inhibit protein synthesis was tested in a cell-free assay. The $IC_{50}$ was $10^{-11}M$ for dgA, rCD4-SATA-dgA and rCD4-SMPT-dgA and $>10^{-8}M$ for SMCC-derived conjugate (Table I). The SMCC conjugate was not toxic in the assay because free dgA could not be released by reduction.

The $LD_{50}$ of the rCD4-SATA-dgA and rCD4-SMPT-dgA in mice were similar (Table I). In these studies, increasing amounts of rCD4-dgA conjugates were injected i.p. into 3 groups of 4 C3H/HEJ mice weighing 15 g and the $LD_{50}$ was calculated based on deaths occurring within 10 days. For SMPT-linked rCD4-dgA conjugates, the assay was repeated twice using 3 groups on four BALB/c mice weighing 20 g. An average value for both $C_3H/HEJ$ and BALB/c mice was calculated.

The $LD_{50}$ of the non-toxic conjugate rCD4-SMCC-dgA was not determined. The $LD_{50}$s of the two active conjugates, rCD4-SATA-dgA and rCD4-SMPT-dgA were 100 ug and 116 ug/g mouse, respectively. This shows that in comparison with the $LD_{50}$ of IgG-dgA conjugates (15–20 ug/g mouse)

were scored subjectively as absent, minimal, mild or marked and assigned grades of 0, 1, 3 or 3, and averaged for each group.

There were no gross lesions in the organs or any of the mice injected with 5%, 10% or 20% of the $LD_{50}$ dose. Microscopically, the liver, kidney, spleen, and brain from all animals were free of lesions.

Lesions were seen in the skeletal muscle of the proximal rear leg, diaphragm and heart. The lesions varied in degree rather than in morphology (Table III). They consisted of myofibers which were fragmented, hyalinized and often infiltrated and surrounded with macrophages and small numbers of neutrophils. The inflammatory cells infiltrate into the endomysium surrounding adjacent normal fibers. The inflammatory response was accompanied by proliferation of sarcoplasmic nuclei and regenerating strap cells were documented admixed with the degenerating fibers in both the appendicular and diaphragmatic musculature. The lesions in the appendicular muscle were multifocal frequently marked, and often concentrated within scattered muscle bundles leaving other muscles unaffected. The lesions in appendicular skeletal muscle were consistently more prominent than those in the diaphragm or heart.

TABLE III

MEAN SCORES FOR MYOPATHY IN MICE
INJECTED WITH rCD-BATA-dgA AND dgA

| Inoculum (%) of $LD_{50}$ | Heart | Diaphragm | Appendicular Skeletal Muscle |
|---|---|---|---|
| rCD4-SMPT-dgA* | | | |
| 5 | 0.00* | 0.00. | 0.00 |
| 10 | 0.00 | 0.25 | 1.25 |
| 20 | 0.00 | 0.00 | 1.75 |
| rCD4-SATA-dgA* | | | |

TABLE III-continued

MEAN SCORES FOR MYOPATHY IN MICE
INJECTED WITH rCD-BATA-dgA AND dgA

| Inoculum (%) of $LD_{50}$ | Heart | Diaphragm | Appendicular Skeletal Muscle |
|---|---|---|---|
| 5 | 0.25 | 0.75 | 2.25 |
| 10 | 0.33 | 0.25 | 2.25 |
| 20 | 0.25 | 0.25 | 1.25 |
| dgA[b] | | | |
| 20 | 0.33[b] | 0.33 | 2.60 |
| Control | 0.00 | 0.00 | 0.00 |

[a]Mean lesion score for 4 animals.
[b]Mean lesion score for 3 animals.

Myocardial lesions were widely scattered and were found in only four animals, one from each group treated with rCD4-SATA-dgA and with dgA. Myocardial lesions were minimal, usually focal and restricted to one or two myofibers. The degenerated myofibers were hyalinized, stippled with basophilic granules, infiltrated with macrophages and neurophils and in some sections, obliterated by infiltrates of macrophages. In none of the animals was there any evidence of heart failure.

Evidence of regeneration in sections of muscle from diaphragm and from the appendicular skeleton indicates that the myopathy is reversible. Myocardium does not regenerate after such damage, but the lesions in the myocardium were minimal, widely scattered and did not result in cardiac failure in any of the mice.

The use of SATA as opposed to SMPT to prepare the conjugates exacerbates the myopathy documented in the appendicular skeleton and diaphragm. In addition, the SATA-linked conjugate produced lesions in the heart. No cardiac lesions were detected in animals injected with rCD4-SMPT-dgA.

The results suggest that rCD4-dgA conjugate prepared with SMPT is not toxic to cardiac myofibers and less toxic to skeletal myofibers than the rCD4-dgA prepared with SATA. No animal presented signs of cardiac failure either clinically or at necropsy.

Taken together, the results suggest that rCD4-dgA prepared with SMPT would be the conjugate of choice for further development as a therapeutic reagent for treating patients with AIDS.

EXAMPLE V

Preparation of CD4 Peptidal Conjugates

Short peptidal conjugate constructs comprising a peptide incorporating the amino acids 41–57 of CD4, coupled to BSA-dgA, are capable of selectively killing HIV-infected cells. The peptide BSA conjugate also inhibits the interaction between CD4 and gp120. The peptide, prior to conjugation with BSA-dgA, has a molecular weight of about 2.3 kDa, and included the addition of an Ala-Cys to its carboxyl terminus to confer more flexibility (Ala) and disulfide-bonding ability (Cys) to the peptide. For these exemplary studies, the Ala at position 55 was labeled with [$^3$H] to a specific activity of $3.8 \times 10^4$ cpm/mg. Although, even at high concentrations, the peptide alone was unable to inhibit the binding of CD4 to gp120, when it was coupled to BSA though a disulfide bond, this conjugate was able to inhibit the binding of horse radish peroxidase (HRP)-labeled CD4 to gp120 albeit at a concentration 100 times higher than the 4 domain rCD4 molecule (FIG. 14).

The coupling of peptide 41–57 to BSA was accomplished by thiolating the BSA with a molar excess of a mixture of N-succinimidyl-S-thioacetate (SATA) and N-succinimidyl-3-(2-pyridyldithio)propionate (SPDP). The thiolated BSA was then reacted with the peptide and the conjugate was deacetylated with hydroxylamine and reacted with reduced, Ellmanized dgA. Alternatively, the BSA molecule was thiolated with SATA and conjugated to the peptide by carbodiimide treatment. The conjugates were deacetylated with hydroxylamine and coupled to reduced and Ellmanized dgA to yield the conjugates.

The reaction is as follows:

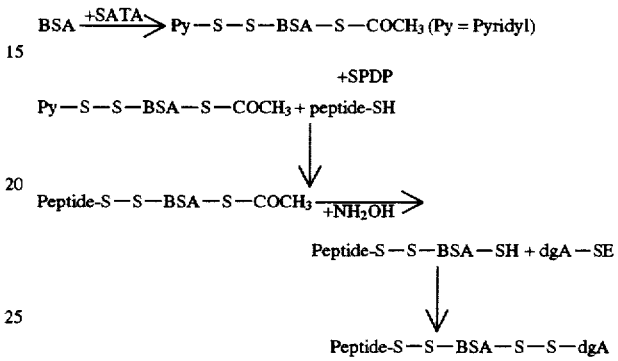

The peptide/BSA molar ratio was approximately 8 as determined by measuring the radioactivity and the protein concentration of the peptide-S-S-BSA conjugate. The peptide was also coupled directly to the dgA molecule following thiolation of dgA with SPDP, reduction with DTT, and reaction with Ellman's reagent (DTNB). Since the dgA molecule contains only two lysine residues (as well as one αNH$_2$ and one reactive cysteine residue), not more than 4 thiol groups are available on the treated dgA for coupling to the SH-containing peptide.

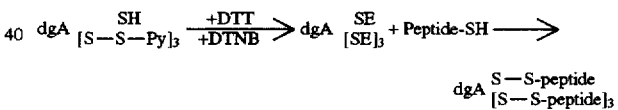

The peptide-S-S-BSA-dgA and peptide-BSA-S-S-dgA were partially purified from the reaction mixture by HPLC on TSK-3000. The conjugate contained contaminating peptide-S-S-BSA which cannot be completely separated by this procedure. The peptide-dgA conjugates were purified by gel filtration on Sephadex G-25 and were free of unreacted peptide but contained trace quantities of free dgA.

The $M_r$ of the peptide-S-S-BSA-S-S-dgA (as determined by HPLC and SDS-PAGE), was approximately 120 kDa, a value corresponding to 8 molecules of peptide bound to one molecule of BSA and one molecule of dgA.

The ability of the dgA in the conjugate to inhibit protein synthesis was determined by a cell-free rabbit reticulocyte assay following reduction of the conjugate. The IC$_{50}$ was similar to that of the uncoupled dgA ($10^{-11}$M). To determine the cytotoxicity of the peptide-conjugates as compared to CD4-dgA, infected vs uninfected H9 cells were cultured with immunoconjugates for 72 hours and then labeled with [$^3$H]-leucine for 6 hours. The results are presented in FIG. 1b and show that the peptide-S-S-BSA-S-S-dgA was able to kill the infected target cells with an IC$_{50}$ that was about 2- to 8-fold higher than that of rCD4-dgA. The conjugates containing peptide-S-S-dgA did not inhibit the binding of CD4 to gp120, but their ability to kill HIV-infected cells has not yet been determined.

Other Possibilities for Preparing Effective CD4-Peptide-dgA Conjugates

A. Enlarging the Size of the Peptide.

The peptide containing residues 41–57 of CD4 was able to inhibit the binding of CD4 to gp120 only when bound to BSA in a molar ratio of 6–8 peptides/BSA molecule. This suggests that the affinity of the peptide-construct for gp120 is lower than that of the intact 2 or 4 domain rCD4 molecule. The lower affinity may be responsible for the 2- to 8-fold less effective killing of HIV-infected cells. These results suggest that peptide 41–57 could be too short to interact with the gp120 molecule optimally. Thus, it is proposed that still further advantages will be realized through the use of a longer peptide which also contains, e.g., residues 57–84.

It should be noted that this peptide will not contain any disulfide loop and therefore may not display the spatial configuration of the natural V1 domain of CD4. Moreoever, since the gp120-binding site of the intact CD4 molecule is lost following reduction of disulfide bonds in denaturing buffer (100), this disulfide loop may be necessary for high affinity binding. It is proposed that, two approaches may be taken to generate a peptide with improved affinity for gp120. In the first, a peptide containing residues 41–84 will be coupled to thiolated or non-thiolated dgA, or to thiolated human serum albumin (HSA) as described for BSA. In the second case, a peptide containing amino acid residues 16–84 (between the two cysteines) will be obtained sythetically or by a recombinant DNA methodology. To increase the affinity of binding, it is proposed to introduce 5–10 glycine residues onto the last C-terminal amino acid residue before adding the cysteine, which is important for coupling to HSA or dgA. This polyglycine arm might expose the gp120-binding site of the peptide in a more effective way and, hence, increase the affinity of binding.

B. Prolonging the Serum Half-Life of the Peptide-Coniugate.

If an active conjugate containing only the peptide and dgA is obtained, it will probably have a short-serum half-life. To prolong the half-life of the conjugate, it is proposed that the gp120-binding peptide be chemically coupled to another molecule to confer a longer serum half-life. One possible molecule is pepstatin (a pentapeptide containing iso-valeryl-L-valyl-L-valyl-4-amino-3-hydroxy-6-methylheptanoyl-alanyl-4-amino-3-hydroxy-6-methyl-heptanoic acid). Pepstatin is a powerful inhibitor of cathepsin D and the renin-angiotensin reaction. Administration of pepstatin concomitantly with IL-2 reduced the degradation of this protein and prolonged its serum half-life (101). Therefore, it might be possible to couple pepstatin to the N-terminal end of the peptide and, hence, confer a longer serum half-life to the conjugate. Alternatively, pepstatin could be administered concomitantly with the peptide-conjugate.

C. Different Carrier Proteins. In initial studies, BSA was used as the carrier of the peptide in order to couple it to dgA. To use these conjugates in humans, it will be preferred to use a human protein to avoid an immune response. This could be done in several ways:

1) HSA could be substituted for BSA. The half-life of HSA in humans is 7 days. Furthermore, the Mr of the conjugate could be decreased by using a tryptic fragment of HSA (with 30% of the Mr) with the same half-life (102). This would generate a conjugate of 55–60 kDa.

2) Other experiments conducted in the inventors' laboratory have shown that a human monoclonal anti-gp41 bound to dgA is an effective immunotoxin (IT) for HIV-infected cells (103). To this end, the CD4 peptide will be coupled to the purified human anti-gp41 monoclonal antibody or its Fab' fragment, and this construct then coupled to dgA. The generation of a molecule which can bind to both gp41 and gp120 should allow the conjugate to more effectively bind to all HIV-infected cells, even those expressing low densities of either gp41 or the gp120. This should also improve the potency of the immunoconjugate. For the preparation of this conjugate, the Fab' fragment or intact molecule will be thiolated with SATA and coupled to dgA through cysteine residues followed by conjugation with Ellmanized peptide through deacetylated thiol groups introduced by SATA. This conjugate should have a longer half-life in the circulation with the intact gp41 molecule as carrier.

D. Increasing the Transmembrane Transfer of the Conjugate.

The lower cytotoxic activity of the conjugates containing peptides as compared to CD4-dgA may be a result of less efficient translocation of the peptide conjugate across a membrane of the HIV-infected cell. To increase transmembrane transfer of the water soluble conjugate, the carrier portion (e.g., HSA or Ig) can be made more hydrophobic by introducing an anchor such as stearic acid (104). It has recently been shown that the introduction of two fatty acid groups into the ricin A chain increased its toxicity so that it was comparable to that of native ricin (104). By introducing fatty acids into the HSA or an Ig molecule, it might be possible to increase the toxicity of the conjugate, but yet not reduce its specificity.

E. Changing the dgA Segment of the Conjugate.

In order to render the dgA less immunogenic and introduce only the active site into the conjugate, dgA will be treated with a variety of chemicals and enzymes to prepare the shortest possible segment which retains N-glycosidase activity. Such treatments will include (see FIG. 17):

1) Hydroxylamine.

The dgA molecule contains only one asparaginyl-glycyl peptide bond (positions 141–142) which is susceptible to cleavage by hydroxylamine. By splitting the dgA with hydroxylamine, two fragments can be obtained. One contains the first 141 amino acid residues in the N-terminal portion and the other the 142–265 amino acid residues in the C-terminal portion. Both fragments will be tested for their ability to inhibit protein synthesis in a cell-free rabbit reticulocyte assay.

2) Cyanogen bromide.

The fragment of dgA (1–141) should not be susceptible to cleavage by cyanogen bromide since it does not contain a methionine residue. The fragment from 142–265 has three methionines and should be split into four fragments of different sizes containing 32, 13, 63 and 12 amino acids, respectively. All four peptides can be isolated and tested for activity in the rabbit reticulocyte assay. If the toxic activity is associated with one or more of the four fragments, these fragments will be used for conjugation to the gp120-binding peptide.

3) Papain.

If the dgA molecule is bound to Blue Sepharose and treated at room temperature with papain, one fragment of dgA with an approximate Mr of 7 kDa remains attached to the Blue Sepharose and can be eluted with NaCl. The peptide does not contain cysteine and is rich in arginine, suggesting that it might contain the N-terminal portion of the A chain (residues 1–60). In preliminary experiments, the toxic activity of this fragment was 20% that of the initial dgA. These results suggest that fragment 1–141 (obtained with hydroxylamine) may contain the toxic site. It should bind to Blue Sepharose and its size could be further diminished by papain cleavage.

F. Decreasing the Immunocrenicity of dgA by Chemical Alteration.

Experiments designed to diminish the immunogenicity of dgA by chemical modification of the molecule with agents that decrease immunogenicity will be performed. Such an agent is PEG. Alternatively, the electrical charges of some of the amino acid residues can be changed by cationization of the molecule (e.g., succinylation).

EXAMPLE VI

Large Scale Preparation of Ricin A Chain-CD4 Conjugate

A. INTRODUCTION

As demonstrated in the examples above, disulfide-bonded conjugates of recombinant human CD4 antigen (rCD4) and the deglycosylated form or ricin A chain (dgA) effectively kill a human T cell line (H9) infected with the Human Immunodeficiency Virus (HTLV$_{IIIb}$ or HIV-1). A major factor affecting the efficacy of such conjugates in vitro, as well as their stability and toxicity in vivo, is found to be the chemical nature of the cross-linker used to introduce a disulfide bond(s) between the rCD4 and dgA molecules (92). Moreover, results have indicated that a rCD4-dgA conjugate prepared with N-succinimidyl-oxycarbonyl-α-methyl-(2-pyridyldithio)toluene (SMPT) is superior since it is active and has a hindered disulfide bond between rCD4 and dgA which confers stability in vivo. Therefore, rCD4-dgA prepared with SMPT is the cross-linker of choice for use as a therapeutic drug to treat HIV-infected individuals. In this example, a standardized procedure for the large scale preparation of rCD4-SMPT-dgA and a description of the physicochemical and biological properties of the rCD4-dgA is presented.

B. MATERIALS AND METHODS 1. rCD4

The recombinant protein containing amino acids 1 to 368 was prepared as described (75), dissolved in phosphate-buffered saline (PBS) with 0.05% Tween 20 at concentrations of 5 mg/ml. The absorption coefficient (at 10 mg./ml) and molecular mass used for rCD4 were 15 and 45 kDa, respectively.

2. dgA

The dgA chain of ricin was obtained from Inland Laboratories (Austin, Tex.), and was prepared and characterized as previously described (Fulton et al., 1986). The protein was dissolved in PBS with 50% glycerol at approximately 4 mg/ml and stored at −20° C. The absorption coefficient (at 10 mg/ml) and the molecular mass for dgA were 7.7 and 30 kDa, respectively.

3. Preparation of rCDr-dgA

All procedures were performed according to the guidelines of Good Laboratory practice (GLP) (93) with sterile, endotoxin-free distilled water (obtained by reverse-osmosis), buffers and equipment using a fully automated biocompatible liquid chromatography system as described (94). The four steps of the preparation and purification procedures in the present example were accomplished in 48 hours and 24 hours, respectively (FIG. 9).

4. Derivatization of rCD4

200 to 400 ml of a solution containing rCD4 (5 mg/ml) was mixed with 4 to 8 ml of SMPT (6.5 mg/ml dimethylformamide) while stirring for 1 hour at room temperature. The mixture was cooled on ice and applied to a Sephadex G-25 Bioprocess column (Pharmacia, Uppsala, Sweden) (25×30 cm) (flow rate 5 L/hr) equilibrated with nitrogen-flushed 0.05M phosphate buffer with 0.003M Na$_2$ EDTA, pH 7.5 (PBE) at 4° C. The protein fraction was collected automatically into a spiral cartridge Amicon CH2 concentrator (YM-30) and concentrated to 2 mg/ml. The rCD4-MPT solution, free of any MPT, was maintained on ice no longer than 1 hour before reacting it with reduced dgA. The average number of MPT groups per molecule of rCD4 was determined by measuring the absorption at 343 nm of an aliquot treated with dithiothreitol (DTT) (10 mM, final concentration) for 15 minutes at room temperature and using the equation: MPT groups/one molecule of CD4= $A_{343} \times 67.5/A_{280} \times 8.1 - A_{343} \times 5.1$.

5. Reduction of dgA 250 to 500 ml of dgA solution (approximately 4 mg/ml) was treated with 25 to 50 ml of DTT (7.7 mg/ml) with stirring. The mixture was incubated for 1 hour at room temperature in the dark. The mixture was cooled in ice and applied to a Sephadex G-25 Bioprocess column (Pharmacia, Uppsala, Sweden) (25×30 cm) (flow rate 5 L/hr) equilibrated with nitrogen-flushed PBE at 4° C. The protein fraction was collected automatically into a Amicon CH2 concentrator (YM-10) and concentrated to 2 mg/ml. The freshly reduced dgA was immediately mixed with rCD4-MPT solution in a weight ratio of 1:1 (dgA/rCD4 molar ratio=1.5) and the mixture was sterilized by filtration through a 0.22 mμ disposable filter. The conjugation reaction lasted 48 hours at room temperature under nitrogen.

6. Purification of rCD4-dgA

The crude conjugate (between 1–2 L containing 2–4 g of protein) was cooled in ice and applied to the Blue-Sepharose CL-4B Bioprocess column (Pharmacia, Uppsala, Sweden) (11.6×30 cm) (Flow rate 2 L/hr) equilibrated with PBE at 4° C. The fraction washed out with this buffer was discharged (contains nonreacted rCD4) and the column was further eluted with 0.5M NaCl in PBE. The eluted protein (rCD4-dgA+dgA) was concentrated to approximately 700 ml and loaded, after cooling on ice, to Sephacryl S-200HR Bioprocess column (Pharmacia, Uppsala, Sweden) (25×60 cm) (flow rate 4 L/hr) equilibrated with 0.145M NaCl at 4° C. The first peak contained aggregated rCD4-dgA (150 kDa), the second peak rCD4-dgA (80 kDa), and the third peak dgA (30 kDa).

The rCD4-dgA conjugate was concentrated to 1–2 mg/ml and was sterilized by filtration through a 0.22 mμ disposable filter. Samples were aliquoted into endotoxin-free vials (Wheaton serum bottle, Southland Cryogenics, Carrollton, Tex.) at 10 and 20 mg per vial and sealed in a laminar flow hood. The vials were immediately snap-frozen at −70° C. and were stored at this temperature for 1 year without any change in activity.

7. Analysis of the rCD4-dgA Conjugate

The cell-free rabbit reticulocyte assay HIV-infected H9 cell assay (95) binding and killing of Daudi cells (92, 94), SDS-PAGE (94), Limulus amoeba lysate (LAL) assay, LD$_{50}$ determination in mice, clearance from the blood, and tissue reactivity in mice were carried out as described.

Relative binding values for rCD4-dgA conjugates (vs non-conjugated rCD4) were determined by an ELISA assay. Wells of a microtiter plate were coated overnight at 4° C. with 2 μg/well recombinant gp120 (Genentech, Inc., San Francisco, Calif.) in 0.1M bicarbonate buffer, pH 9.6, and then blocked with 100 μl of 0.5% bovine serum albumin in PBS containing 0.05% Tween 20, for 3 hours at room temperature. Various concentrations of rCD4-dgA or rCD4 (3–100 ng/ml) were added in 100 μl and the plate was incubated for 2 hours at room temperature. The binding of the rCD4 derivatives to gp120-coated wells was determined with horse radish peroxidase-labeled anti-CD4 (Genentech, Inc., San Francisco, Calif.) and a tetramethylbenzidine/ hydrogen peroxide substrate. The absorbance was recorded with an ELISA plate reader (Biorad, South Richmond, Calif.) using the 450 nm filter.

Linear regression curves were generated by plotting the absorbance vs the rCD4 concentration (in ng/ml) for each sample. By dividing the value of the slope of the linear curve of the sample (rCD4-dgA) to that of the standard (rCD4), the relative binding values for rCD4-dgA conjugate was calculated. The kinetics of the rCD4-MPT conjugation with dgA-SH was followed by suing high performance liquid chromatography (HPLC) on a 0.75×60 cm TSK 3000SW column (Sperhogel, LKB, Bromma, Sweden). After mixing rCD4-MPT with dgA-SH, 0.2 m. aliquots were withdrawn at various intervals of time and analyzed by HPLC at a flow rate of 1 ml/minute in PBE. The increasing percentage of rCD4-dgA conjugates was plotted against time (in hours) and the curve was used to determine the incubation time yielding the highest amount of rCD4-dgA conjugate.

To prepare small amounts of a highly purified rCD4-dgA conjugate, an aliquot of the rCD4-dgA preparation obtained after purification on Blue-Sepharose and Sephacryl S-200HR chromatography (2 ml) was further submitted to HPLC on a preparative TSK G3000SW column (Ultropac, LKB, Bromma, Sweden) (2.1×60 cm) able to process 30 mg protein at a flow rate of 3 ml/min. The highly purified rCD4-dgA conjugate was maintained sterilely at 4° C.

C. RESULTS

1. The Procedure

The large scale preparation of rCD4-dgA conjugates is generally similar to the procedure already described for the preparation of the small amounts of rCD4-dgA with SMPT as a cross-linker (92). The critical step of the coupling procedure is the time of incubation between the rCD4-MPT and the reduced dgA-SH as shown in FIG. 10. It can be seen that the coupling reaction is completed after 48 hours. If the incubation time is extended t 72 hours [as recommended for the preparation of immunotoxins (ITs) (66), the percentage of aggregated rCD4-dgA increases, thus reducing the yield and purity of the 80 kDa rCD4-dgA. The average number of MPT groups introduced into the rCD4 molecule ranged from 1.0 to 1.5 (mean 2.1±0.3), suggesting that at least one-third of the rCD4 molecules are derivatized with a single disulfide group after treatment with SMPT. These rCD4 molecules are able to react with freshly reduced dgA-SH which has only one of its two cysteine residues available for interaction with rCD4-MPT.

This reaction leads to the formation of a rCD4-S-S-dgA conjugate as indicated in FIG. 9. When rCD4 derivatized with two MPT groups reacts with dgA, conjugates with a higher molecular weight (Mr) are formed [e.g., (rCD4) (dgA$_2$)]. By treating rCD4 with a moderate excess of SMPT (3.5 moles SMPT/mol rCD4) some rCD4 molecules are not derivatized and therefore are unable to react with reduced dgA. In fact, by chromatography of rCD4-dgA on reduced thiopropyl-Sepharose (Serva, St. Louis, Mo.), about 25% of the SMPT-treated rCD4 did not bind to the column indicating that this rCD4 fraction did not contain any MPT disulfide groups. For this reason, it can be recovered after Blue-Sepharose chromatography and further used for another conjugation.

After derivatization with SMPT and gel filtration on Sephadex G-25 in PBE, the rCD4-MPT is soluble in PBE without Tween 20; therefore, this detergent is not needed in the conjugation and purification procedures. The pH and the ionic strength of PBE used for the conjugation also allows the interaction of dgA (free or bound to rCD4) with Blue-Sepharose; therefore, no dialysis step is necessary before purification of the conjugate.

2. The Design and Operation of the Chromatographic System

The preparation of rCD4-MPT and dgA-SH, as well as the purification of the rCD4-dgA conjugate (FIG. 9), involved the use of four Pharmacia Bioprocess columns integrated in an automatic circuit controlled by a process controller as described for the large scale preparation of immunotoxins (94). The chromatographic system is compatible with the recommended cleaning-in-place and sanitation procedures using various concentrations of NaOH (0.1–0.25M). To prevent particles from entering the columns, the chromatographic fractions were filtered through a 0.45 mg filter after each chromatographic step. The buffers were pumped with a Watson-Marlow 501U pump through a Versaflow capsule filter (0.45 mμ) (Gelman, Ann Arbor, Mich.) into a sterile, endotoxin-free cylindrical polypeptide tank (114 L) (Fisher Scientific, Pittsburgh, Pa.), maintained with the chromatographic system at 4° C. in cold boxes. From these reservoirs, the cold, nitrogen-flushed buffers were pumped by another identical pump into the chromatographic system. The protein fractions of interest were directly collected into CH2 concentrators also maintained in the cold boxes (94).

3. Chromatographic Resolution

The separation of proteins from excess DTT or MPT (SMPT) was achieved with very good efficiency when the Sephadex G-25 columns were not loaded with a volume larger than 500 ml (3% of the bed volume of the columns). This is important since traces of MPT (SMPT) in rCD4 and DTT in dgA may result in low yields.

The use of Blue-Sepharose results in elimination of almost all unreactive rCF4 while the final chromatographic step on Sephacryl S-200HR results in a clean separation of rCD4-dgA from dgA, but in an incomplete separation from rCD4-dgA molecules with a Mr higher than 80 kDa (FIG. 11). Therefore, as shown in FIG. 12, the final preparation of rCD4-dgA is 90% pure and contains both high Mr. conjugate (s), some free rCD4 and traces of dgA. It should be noted that each of the two electrophoretic bands with 75 kDa and 97 kDa contain one molecule or rCD4 coupled to one molecule of dgA chain (92). The purity of the rCD4-dgA conjugate can be improved by an additional purification of HPLC on a preparative column which eliminates almost all high Mr conjugate(s) and free dgA. Unfortunately, the available size of the HPLC column does not allow the purification of more than 100 mg/5 hours; therefore, this method cannot be used for large scale procedures.

4. Yields

The theoretical yield of the conjugation of rCD4-MPT (containing one MPT group) with dgA-SH is approximately 50% if we take into account the fact that approximately 25% of the rCD4 does not have disulfide groups introduced into the molecule and that the same percentage of rCD4 probably contains more than one MPT group per molecule. When the percentage of the rCD4-S-S-dgA formation was followed by HPLC (FIG. 10), it represents a maximum of 30%. After two chromatographic steps (Blue-Sepharose and Sephacryl S-200HR), both followed by concentration procedures, a significant amount of the rCD4-dgA conjugate was lost due to either the adsorption of the protein to the filters or to the deal volume of the spiral cartridge concentrator. Therefore, the final yield never represented more than 20% of the rCD4 introduced into the reaction and somewhat less of the initial dgA. The free dgA (nonreacted with rCD4) isolated through the last chromatographic step, represents approximately 25% of the initial dgA and can be further used for another conjugation.

5. The Properties of the rCD4-dgA Conjugate

The routine checking of the rCD4-dgA preparations obtained by the large scale procedures include the assays presented in Table IV. rCD4-dgA, obtained by GLP-scale-up procedures, was sterile and contained very little endotoxin (100 times less than the limit set by the FDA). The other properties were comparable with those of the rCD4-dgA prepared by the small scale procedures already reported (92).

TABLE IV

ANALYSIS OF rCD4-dgA CONJUGATES

| Assay | Result Large Scale | Small Scale[a] |
|---|---|---|
| Yield (% of the initial rCD4) | 19.8 | 17.5 |
| Sterility | Negative | Positive |
| LAL assay (EU/ml) | 0.1 | 28.0 |
| HPLC (% of 80 kDa peak) | 90.0 | 90.0 |
| gp120 binding (% of initial rCD4) | 80.7 | 83.6[b] |
| Reticulocyte assay (IC$_{50}$) (×10$^{-11}$M) | 2.1 | 1.2 |
| HIV-infected cell assay (IC$_{50}$) (×10$^{-10}$M) | 1.0 | 2.0 |
| Interaction with Class II antigens[d] | Negative | Negative |
| Blood Half-life in mice (min.) | 221.0 | 209.0 |
| Dissociation in vivo (% of dgA released in 4 hours) | 4.0 | 4.4[e] |
| LD$_{50}$ in mice (μg/g) | 91.0[f] | 116.0 |
| Tissue reactivity in mice | Myositis | Not done |

[a]From Ghetie, et al. (92)
[b]Value obtained with a different assay (92).
[c]The same value was obtained with the rCD4-dgA further purified on HPLC.
[d]Tested by the binding and killing of Daudi cells (92).
[e]Five times more dgA was released from a conjugate prepared with another crosslinker (92)
[f]For dgA, the LD$_{50}$ was 30 μg/g mouse.

D. DISCUSSION

As demonstrated by the foregoing example, the preparation of the rCD4-dgA conjugate with the SMPT cross-linker can be scaled up to obtain gram amounts of conjugate without impairing the yield, purity or biological activity of the preparation, as compared to the procedures utilized for its preparation in small amounts (mg) for experimental purposes. The chromatographic system used for the preparation and purification of rCD4-dgA was in certain ways comparable to that used for the preparation of Fab' -dgA (94), but using fewer chromatographic steps and a simplified procedure. Importantly, apparently due to this fact, the contamination with endotoxin was 10 times lower. The impurities contained in the rCD4-dgA preparation (approximately 10%) did not diminish its cytotoxic activity since no significant increase in its activity (IC$_{50}$) was recorded after removing these impurities by a supplementary preparative HPLC.

The LD$_{50}$ of the conjugate in mice (91 μg/g mouse) would be equivalent to 600 mg/m$^2$ in humans, e.g., approximately 1 g of rCD4-dgA per 70 Kg patient. This relatively low toxicity of rCD4-dgA to mice (91 μg/g) coupled with its potent cytotoxicity (IC$_{50}$=10$^{-10}$M) to HIV-infected H9 human cells and its lack of interaction with Class II antigens suggest that rCD4-dgA will be a safe and specific drug for the treatment of patients with AIDS. Moreover, the good stability of rCD4-dgA in vivo as well as its longer half-life in the circulation of mice, further indicates that the conjugate will be clinically useful.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE VI

CD4 Peptide Conjugates—rgp120 Binding in the Presence of HIV$^+$ Sera

Sera from HIV$^+$ individuals inhibit the interaction between rCD4 and rgp120, thereby interfering with the ability of soluble rCD4 to block infection with HIV or of rCD4-toxin conjugates to kill HIV-infected cells. In this example, it is demonstrated that the inhibitory activity of such sera is caused primarily by anti-gp120 antibodies that do not recognize the CD4-interaction site on gp120. The presence of antibody that can block the binding of CD4 to gp120 would seriously undermine CD4-based therapies for patients with AIDS (5,10,11). To circumvent this blocking by HIV$^+$ sera, small CD4 peptide segments were generated which are capable of binding to rgp120 even in the presence of HIV$^+$ sera.

In order to test the binding of these CD4 peptides to rgp120, CD4 peptides corresponding to residues 41–57, 41–84, and 81–92 were synthesized and bound to ovalbumin (OVA), generating peptide-OVA constructs with 3–5 peptides per molecule of OVA. The binding of these peptide-OVA constructs to gp120 was then compared to rCD4 in the presence of HIV$^+$ or HIV$^-$ sera. The peptide having residues 41–84 [i.e., CD4-peptide (41–84)-OVA] was found to exhibit the highest affinity for gp120, though less than the affinity of rCD4, and was capable of binding gp120 in the presence of HIV$^+$ sera, whereas rCD4 was not capable of such binding. Therefore, constructs utilizing CD4 peptide 41–84 conjugated to toxins, such as dgA, are believed to offer significant promise for blocking HIV infection and preventing the spread of HIV infection in individuals having high titers of anti-gp120 antibodies.

A. MATERIALS AND METHODS

1. Preparation of Peptide-Ovalbumin Conjugates

CD4 derived peptides were synthesized on an Applied Biosystems Inc. (Foster City, Calif.) Model 430A solid phase peptide synthesizer. These peptides contained: 1) amino acid residues 40 to 57 (Gln-Gly-Ser-Phe-Leu-Thr-Lys-Gly-Pro-Ser-Lys-Leu-Asn-Asp-Arg-$^3$H-Ala-Asp-Ser) to which Ala (penultimate) and Cys (C-terminal) were added; 2) amino acid residues 81 to 92 (Thr-Tyr-Ile-Cys-Glu-Val-Glu-Asp-Gly-Lys-Glu-Glu) with $^3$H-Ala at the N-terminal end; and, 3) amino acid residues 41 to 84 (Gly-Ser-Phe-Leu-Thr-Lys-Gly-Pro-Ser-Lys-Leu-Asn-Asp-Arg-Ala-Asp-Ser-Arg-Arg-Ser-Leu-Trp-Asp-Gln-Gly-Asn-Phe-Pro-Leu-Ile-Ile-Lys-Asn-Leu-Lys-Ile-Glu-Asp-Ser-Asp-Thr-Tyr-Ile-Cys) with $^3$H-Ala in position 55. The peptides were purified by reverse phase HPLC and characterized by fast atom bombardment mass spectrometry. A peptide not found in the CD4 molecule and containing 21 amino acid residues (Tyr-Asp-Arg-Pro-Glu-Gly-Ile-Glu-Glu-Glu-Gly-Glu-Arg-Asp-Arg-Asp-Arg-Ser-Gly-Cys) (Immuno-Dynamics Inc., La Jolla, Calif.) was used as control.

Ovalbumin (OVA) (Sigma, St. Louis, Mo.) (1 ml) dissolved in 0.05M phosphate buffer with 0.003M NA$_2$EDTA (PBE) at 5 mg/ml was mixed with 10 μl N-Succinimidyl 3-(2-pyridyldithio) propionate (SPDP) (Pharmacia, Piscataway, N.J.) dissolved in dimethylformamide (Pierce, Rockford, Ill.) at 80 mg/ml (molar ratio SPDP/OVA=24) and the mixture was incubated at 25° C. for 1 hr. The thiolated OVA was separated from the small molecules by gel filtration on Sephadex G-25M equilibrated with PBE and after concentration to 5 mg/ml, immediately mixed with an equal volume of peptide dissolved in PBE at 2 to 5 mg/ml (molar ratio peptide/OVA=5 to 20).

After incubating samples for 2 hr at 25° C., they were passed over a Sephadex G-10 or G-50 column equilibrated with PBE. The first peak containing peptide-OVA, was pooled and concentrated. The number of peptides coupled to OVA was determined by using an absorption coefficient of 0.73 for OVA and the specific radioactivity of the peptides $(2-4\times10^4$ cpm/mg). Values of between 8 to 11 peptide molecules per molecule OVA were determined for both CD4 (40–57)-peptide and CD4 (81–92) peptide-OVA conjugates while for CD4 (41–84), there were 3 to 5 peptide molecules per molecule of OVA. No free -SH groups were detected on peptide-OVA by titration with Ellman's reagent (73).

2. Preparation of Protein-Horseradish Peroxidase (HRP) Conjugates

The rCD4-HRP and IgG-anti-OVA-HRP conjugates were prepared by derivatizing the HRP with succinimidyl-4-(N-maleimidomethyl)-cyclohexane-1-carboxylate (Pierce, Rockford, Ill.) (67) and the rCD4 (Genentech, San Francisco, Calif.) and anti-OVA with N-succinimidyl-S-acetylthioacetate (Calbiochem, La Jolla, Calif.) and hydroxylamine.

3. Absorption of Human Sera on Immobilized Proteins

Protein A, rgp120 or rCD4 were coupled to CNBr-activated Sepharose 4B (Pharmacia, Piscataway, N.J.). The gels were loaded with 1 ml of human serum, washed with PBE containing 0.5% bovine serum albumin and 0.05% Tween 20 until the absorption at 280 nm of the effluent was zero; total collected volume was 10 ml. 1/10 dilutions of these sera were used for inhibition experiments. HIV sera were obtained from seronegative individuals. HIV$^+$ sera were obtained from Walter Reed Stage 6 (AIDS) patients.

4. The Binding of rCD4-HRP to rgp120 and Inhibition by Sera

Wells of a microtiter plate were coated overnight at 4° C. with 100 µl of rpg120 (Genetech, San Francisco, Calif.) (1 µg/ml) in 0.1M bicarbonate buffer pH 9.6 and then blocked for 2 hr at 25° C. with 200 µl of 0.5% bovine serum albumin (BSA) in phosphate buffered saline (PBS) containing 0.5% Tween. Dilutions of HIV$^+$ or HIV$^-$ sera were added (100 µl) and the plate was incubated for 2 hr at 25° C. After washing, 100 µl of rCD4-HRP (5 µl/ml) was added to the wells for 2 hr at room temperature and the binding of rCD4-HRP was detected by 1,1'-azino-di(3-ethyl-benzylthiazoline-6-sulfonic acid) and hydrogen peroxide (Bio-Rad, Richmond, Calif.) using and ELISA-reader equipped with a 405 nm filter. Linear regression curves were generated by plotting the absorbance vs the dilutions of sera for each sample. The inhibition of binding of rCD4-HRP to rgp120 was expressed as the dilution of sera giving 50% inhibition of binding. A variant of this binding assay was also performed in which plates coated with rpg120 were blocked with 5% fetal calf serum (FCS) and the incubation with dilutions of human serum was performed at 37° C. for 30 min followed by the addition of rCD4-HRP directly to the dilutions of human serum without washing followed by further incubation at 37° C. for 30 minutes.

5. The Binding of Peptide-OVA to rgp120 and Inhibition by Sera

Wells coated with rgp120 and blocked as described above were treated with various concentrations of peptide-OVA or OVA (control) in 100 µl and the plate was incubated for 2 hr at 25° C. The plates were washed and then incubated with rabbit IgG anti-OVA coupled to HRP (5 µl/ml) for 2 hr at 25° C. The binding of the labeled antibody was detected as described above. Linear regression curves were generated by plotting the absorption vs the concentration of peptide-OVA.

The inhibition of binding the peptide-OVA to rgp120 was determined in the presence of dilutions of HIV$^+$ and HIV$^-$ sera. Sera were incubated for 2 hr at room temperature in rgp120 coated wells or 30 min at 37° C. before adding the CD4 peptide-OVA with or without washing.

6. The Specificity of rCD4 and Peptide-OVA Binding to rgp120

The specificity of the binding of rCD4-HRP to rgp120 was determined by incubating rgp120-coated wells for 2 hr at 25° C. with various concentrations of rCD4, CD4 peptide (40–57)-OVA, CD4 peptide (81–92)-OVA, CD4 peptide (41–84)-OVA, control peptide-OVA and OVA. The IC$_{50}$s for rCD4, CD4 peptide (40–57)-OVA and CD4 peptide (41–84)-OVA were determined graphically. The relative affinity of the CD4-peptides-OVA for rgp120 vs rCD4 was calculated by dividing the IC$_{50}$ of the rCD4.

The specificity of the binding of CD4 peptides-OVA to rgp120 was demonstrated by incubating the rgp120-coated plates with different concentrations of rCD4 or OVA for 2 hr at 25° C. before adding the CD4 peptides-OVA at concentrations giving an absorption at 414 nm of 0.6 to 0.8.

B. RESULTS AND DISCUSSION

1. Anti-gp120 antibodies Block and Binding of rCD4 to rgp120

The ability of 8 HIV$^+$ and 8 HIV$^-$ human sera to inhibit the binding of rCD4 to rgp120-coated wells of microtiter plates was determined and the results are presented in FIG. 17. The HIV$^+$ sera inhibited binding; the average dilution of HIV$^+$ sera giving 50% inhibition of binding was 1/820±1/336.

HIV$^-$ sera showed some inhibitory activity (50% inhibition at 1:64±1/56). Both values are in agreement with earlier reports (110–114).

Figure 18A:
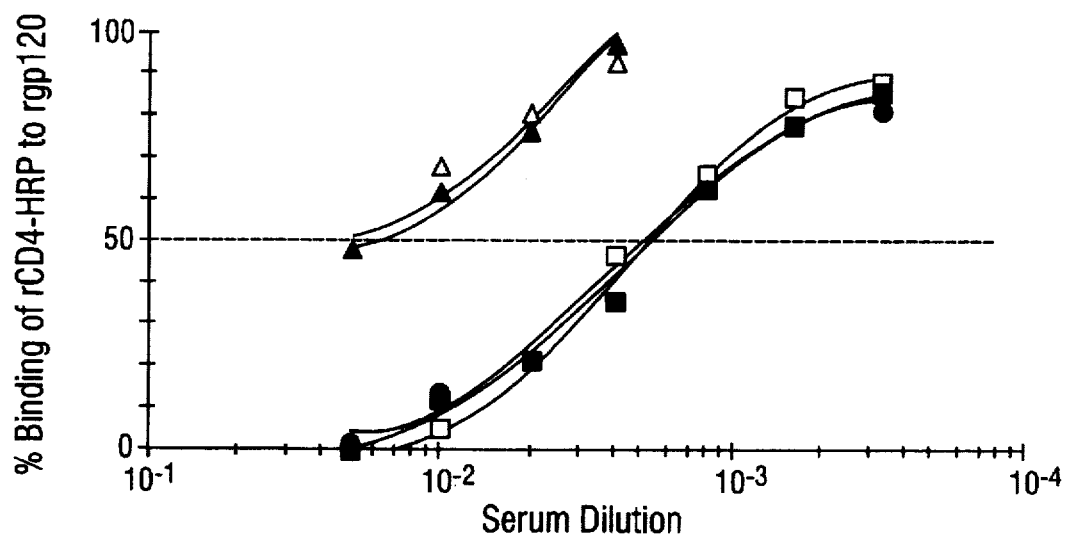
Figure 18B:
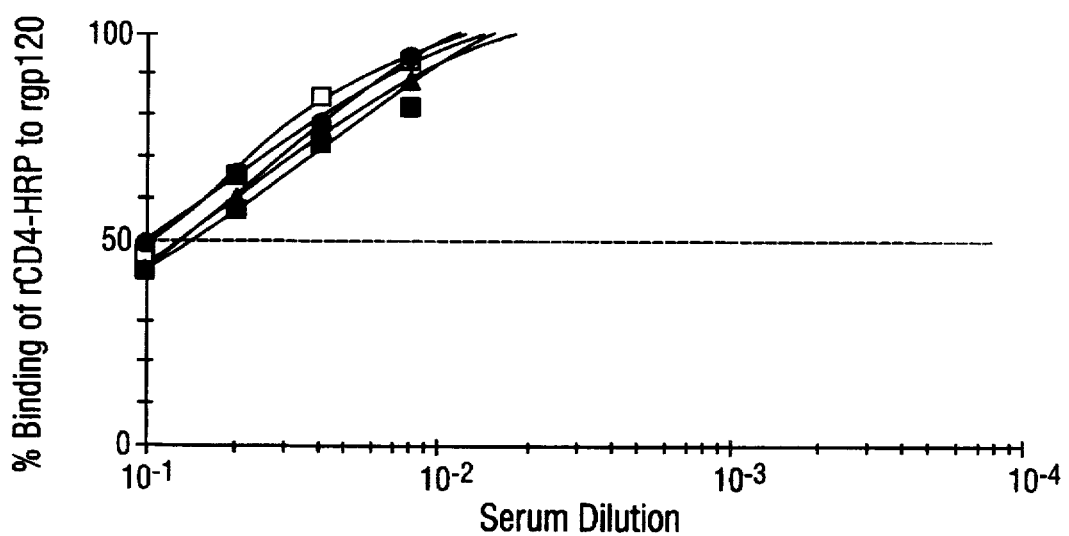

As shown in FIG. 18A, the inhibitory activity of an HIV$^+$ serum was markedly reduced after absorption with rgp120-Sepharose or protein A-Sepharose, but not rCD4-Sepharose, indicating that the inhibitory factor is an immunoglobulin with anti-gp120 activity. Residual inhibitory activity was probably related to incomplete removal of anti-gp120, since only one absorption with rgp120-sepharose was performed. Similar results were obtained with three other HIV$^+$ sera tested. The sera from HIV$^-$ individuals were absorbed with the same panel of immobilized proteins, and no reduction of inhibitory activity was observed (one representative serum is shown in FIG. 18B). These results indicate that the inhibitory factor in sera from HIV$^-$ individuals does not bind to a protein A and is probably not an immunoglobulin. A mannose-binding protein present in normal human sera and reported to inhibit HIV infection of H9 cells (105, 106) is not the blocking factor since it did not bind to mannose-agarose and blocking was not inhibited with mannan. Since human serum albumin (HSA) at a concentration similar to that in the human sera-treated plates gave less inhibition than HIV$^-$ sera (FIGS. 17A and B), the blocking factor is not albumin.

2. The Anti-gp120 Antibody in HIV$^+$ Sera is Not Directed Against the CD4-Binding Site on gp120

To determine whether the anti-gp120 antibodies in HIV$^+$ sera were directed against the CD4-binding site on gp120, three CD4 peptides that have been reported to bind to gp120 were tested. These peptides contain amino acids 40-57 (96), 81-92 (68) and 41-84 (107) of the CD4 molecule. Peptides containing CD4 residues 40-57 and 81-92 did not inhibit the binding of rCD4 to gp120 even at concentrations of 50 µM. However, when these peptides were conjugated to OVA (at a ratio or 3-11 peptide molecules per molecule of OVA), CD4-peptides 40-57 and 41-84 inhibited binding of CD4 to gp120, whereas CD4-peptide (81-92) or an irrelevant peptide (control) conjugated to OVA was not inhibitory (FIG. 19).

The free CD4-peptide (41-84) (not coupled to OVA) was able to interact with rgp120 as demonstrated by its ability to inhibit the binding of rCD4-HRP to rgp120. The $IC_{50}$ of the CD4-peptide (41-84) was 0.6 µM (vs 0.008 µM for rCD4) indicating that its binding affinity is 75 times lower than that of rCD4. When this peptide was coupled to OVA, the peptide-OVA conjugate was able to inhibit the binding of rCD4-HRP to rgp120 with an $IC_{50}$ of 0.031 µM which is four fold lower than that observed for rCD4 (0.008 µM). If the inhibition was calculated relative to the concentration of the peptide and not the peptide-OVA, the affinity between OVA-bound peptide (41-84) and gp120 was approximately 10 times lower than that between rCD4 and rgp120. (Note: in this calculation, peptide was bound to OVA at a molar ratio of 3 to 1.) The ability of the CD4-peptide conjugates to inhibit the binding of rgp120 to rCD4 was not blocked by OVA, further indicating that the interaction between CD4-peptide conjugates and rgp120 is specific.

The binding of CD4-peptide-OVA conjugates to rgp120 was also determined by a direct ELISA assay. As shown in FIG. 20, CD4-peptide (40-57)-OVA and (41-84)-OVA were able to bind to gp120; CD4-peptide (81-92)-OVA, control peptide-OVA or OVA alone did not bind gp120. The amount of CD4-peptide (41-84)-OVA bound was approximately three times lower than that of CD4-peptide (40-57)-OVA. This result is in agreement with the inhibition data presented in FIG. 19 which indicate that the CD4-peptide (41-84)-OVA is twice as active as the CD4-peptide (40-57)-OVA ($IC_{50}$=0.031 µM vs $IC_{50}$=0.06 µM, respectively). If the gp120 coated wells of the microtiter plate were pretreated with intact rCD4, the binding of the CD4-peptide (40-57)-OVA to gp120 was completely inhibited, indicating that binding is specific. These results suggest that the CD4-peptide (40-57) is involved in the gp120-interaction site on CD4 and is consistent with other reports that the gp120 -binding region of CD4 is located between residues 40-57 (96).

In the present invention, the lack of binding of CD4-peptide (81-92)-OVA to rgp120 does not prove that this portion of CD4 is unable to react with the rgp120 molecule since the cysteine residue of this peptide has been reported to be involved in binding (17). In other words, since the cysteine residue was used to form the disulfide bond between the peptide and OVA in the present example, the protein conjugation of CD4-peptide (81-92) through another amino acid residue may cause this peptide to bind rgp120.

3. CD4 Peptide-OVA Conjugates Interact With rgp120 in the Presence of HIV⁺ Sera

Since the CD4-peptide (41-84)-OVA conjugate had the highest affinity for rgp120, we used it to determine whether HIV⁺ sera could interfere with the binding of this peptide to rgp120. The results indicate that neither the HIV⁺ nor the HIV⁻ sera inhibited the binding of CD4-peptide-OVA to rgp120 (FIG. 21). The most likely explanation is that the vast majority of anti-gp120 antibodies in HIV⁺ sera do not react with the CD4-binding site on gp120, but instead react with adjacent regions of gp120 which are not directly involved in CD4-binding. If the gp120-binding site on CD4 is located in a crevice between loops 2 and 3 (107), then the inhibitory effect of an antibody attached to a region adjacent to the CD4 binding site on gp120 may be steric. When using the CD4-peptide (41-84)-OVA conjugate, one or more of the gp120 -binding peptides that protrude from the surface of the carrier protein may gain access to the CD4-binding site on gp120, despite the presence of anti-gp120 antibodies that react with adjacent epitopes on gp120.

In summary, these results suggest that this CD4-peptide (41-84), containing portions of both loops 2 and 3 in the V1 domain of CD4 (107-109), coupled to OVA generates a peptide-carrier which binds to rgp120 with good avidity, albeit lower than that between rCD4 and rgp120. Furthermore, in contrast to rCD4, CD4-peptide (41-84)-OVA binds to rgp120 in the presence of HIV⁺ sera. If such CD4-peptide constructs also bind avidly to HIV-infected cells, they may circumvent the inhibitory activity of anti-gp120 antibodies in HIV⁺ sera. If this is the case, these peptide-constructs may inhibit HIV infection even in the individuals with high titers of anti-gp120 antibodies.

REFERENCES

The references listed below are incorporated herein by reference to the extent that they supplement, explain, provide a background for or teach methodology, techniques and/or compositions employed herein.

1. Barre-Sinoussi et al. (1983), *Science*, 220:868.
2. Popovic et al. (1984), *Science*, 224:497.
3. Gallo et al. (1984), *Science*, 224:500.
4. Schupgbach et al. (1984), *Science*, 224:503.
5. Sarngadharan et al. (1984), *Science*, 224:506.
6. Fauci et al. (1985), *Annals. Intern. Medicine*, 102:800.
7. Curran et al. (1988), *Science*, 239:610; Fauci, ibid., p. 617.
8. Linnan (1987), *Anna. Rev. Immunol.*, 5:562; Sattenau et al. (1988), *Cell*, 52:631.
9. Lane et al. (1983), *N. Engl. J. Med.*, 309:453.
10. Murray et al. (1984), *N. Engl. J. Med.*, 310:883.
11. Bowen et al. (1985), *Annals Intern. Med.*, 103:704.
12. Fauci (1984), *Clin. Res.*, 32:491.
13. Rook et al. (1983), *J. Clin. Invest.*, 72:398.
14. Lane et al. (1985), *N. Engl. J. Med.*, 313:79.
15. Ammann et al. (1983), *Clin. Immunol. Immunopathol.*, 27:315.
16. Stahl et al. (1982), *Am. J. Med.*, 73:171.
17. Vilmer et al. (1984), *Lancet*, 1:753.
18. Koenig et al. (1986), *Science*, 233:1089.
19. Levy et al. (1985), *Virology*, 147:441.
20. Siegel et al. (1985), *J. Clin. Invest.*, 75:1957.
21. Cunningham-Rundles et al. (1983), *J. Clin. Immunol.*, 3:156.
22. Modrow et al. (1987), *J. Virology*, 61(2):570.
23. EPO Publication Number 0,314,317 A1.
24. Capon et al., U.S. patent application Ser. No. 104,329, filed Oct. 2, 1987.
25. Capon et al., U.S. patent application Ser. No. 250,785, filed Sep. 28, 1989.
26. Vitetta et al. (1987), *Science*, 238:1098; Blakey et al. (1986), Adv. Allergy; Pastan et al. (1986), 47:641.
27. U.S. patent application Ser. No. 155,336, filed Feb. 12, 1988.
28. U.S. patent application Ser. No 323,486, filed Mar. 14, 1989.
29. Lane et al. (1985), *Ann. Rev. Immunol.*, 3:477.

30. Maddon et al. (1985). Cell, 42:93.
31. Reinherz et al. (1980). Cell, 19:821.
32. Swain (1981). Proc. Natl. Acad. Sci., 78:7101
33. Engleman et al. (1981). J. Immunol., 127:2124
34. Spitz (1982). J. Immunol., 129:1563
35. Biddison et al. (1982). J. Exp. Med., 156:1065
36. Wilde et al. (1983). J. Immunol., 131:2178.
37. Thomas et al. (1981). J. Exp. Med., 154:459.
38. Meuer et al. (1982). Proc. Natl. Acad. Sci. USA, 79:4395.
39. Krensky et al. (1982). Proc. Natl. Acad. Sci. USA, 79:2365.
40. Klatzman et al. (1984). Science, 225:59.
41. Dalgleish et al. (1984). Nature [London], 312:767.
42. McDougal et al. (1985). J. Immunol., 135:3151.
43. McDougal et al. (1986). Science, 231:382.
44. Maddon et al. (1986). Cell, 47:333.
45. Snider et al. (1983). Ann. Neurol., 14:403.
46. Shaw et al. (1985). Science, 227:177.
47. Epstein (1985). AIDS Res., 1:447.
48. Koenig (1986). Science, 233:1089.
49. Ho et al. (1985). N. Engl. J. Med., 313:1498.
50. Levy et al. (1985). Lancet, 11:586.
51. Maddon. (1986). Cell, 47:444.
52. Funke et al. (1986). J. Exp. Med., 165:1230.
53. Tourvielle et al. (1986). Science, 234:610.
54. Lifson et al. (1986). Science, 232:1123.
55. Sodroski et al. (1986). Nature, 322:470.
56. Lifson et al. (1986). Nature, 323:725.
57. Mitsuya et al. (1987). Nature, 325:773.
58. Madden (1985). Cell, 42:93.
59. Thorpe et al. (1985). Eur. J. Biochem., 147:197-206.
60. Fulton et al. (1988). Cancer Res., 48:2618-2625.
61. Smith et al. (1987). Science, 238:1704-1707.
62. Wojchowski et al. (1986). J. Immunol. Methods, 90:173-177.
63. Fulton et al. (1986). J. Biol. Chem., 261:5314-5319.
64. Fulton et al. (1988). Can. Res., 48:2618-2625.
65. Duncan et al. (1983). Anal. Biochem., 132:68-73.
66. Thorpe et al. (1987). Can. Res., 47:5924-5931.
67. Ishikawa et al. (1983). J. Immunol., 4:209-327.
68. Lifson et al. (1988). Science, 241:712-716.
69. O'Hare et al. (1987). FEBS Lett., 216:731.
70. Remington's Pharmaceutical Sciences, 16th edition. (1980). Mack Publishing Company, edited by Oslo et al.,
71. Knowles et al. (1987). Anal. Biochem., 120:440-443.
72. Duncan et al. (1983). Anal. Biochem., 132:68.
73. Ellman et al. (1959). Arch. Biochem. Biophys, 82:70; Fulton et al. (1986). Immunol., 136:3103.
74. Press et al. (1986). Immunol. Lett., 14:37.
75. Smith et al. (1987). Science, 238:1704.
76. IC$_{50}$ is the concentration of a conjugate that reduces DNA or protein synthesis by 50%.
77. The usual way to evaluate the toxicity of a conjugate is to pulse-label cells with [$^{3}H$] leucine or [$^{35}S$]methionine. This requires centrifuging the microtiter plates and resuspending the cells in deficient medium before they are labeled. For safety reasons, this could not be done with HIV-infected cells. Therefore, [$^{3}H$]thymidine was used for labeling.
78. Lasky et al. (1986). Science, 233:209.
79. Ellman (1959). Arch. Biochem. Biophys., 82:70-77.
80. Phillips et al. (1987). Immunol. Lett., 17:159-120.
81. Blakey et al. (1988). Progress in Allergy (Monoclonal Antibody Therapy). (H. Waldmann, Ed.) pp. 50-90, Karger, Basel, Switzerland.
82. Doyle et al. (1987). Nature, 330:256-259.
83. Tolleshang et al. (1982). Cell, 30:715-724.
84. Beeken et al. (1962). J. Clin. Invest., 40:1312-1332.
85. Thorpe et al. (1988). Can. Res., 48:6396-6403.
86. Kyte et al. (1982). J. Mol. Biol., 157:105-132.
87. Uhr et al., U.S. Pat. No. 4,664,911, issued May 13, 1987.
88. Vitetta. E. (1988). J. Immunol., 136:1880-1887.
89. Chang et al. (1987). Proc. Natl. Acad. Sci. USA, 84:5640-5644.
90. Wawrzynczak et al. (1987), in Immunoconjugates: Antibody Conjugates in Radioimagery and Therapy of Cancer, ed. C. W. Vogel, Oxford U. Press, pp. 28-55.
91. Funmatsu et al. (1970). Jap. J. Med. Sci. Biol., 23:264-267.
92. Ghetie et al., (1990). Bioconjugate Chem., 1:24.
93. Simmons. P. L. (1987) in: International Center for Technology Transfer, Tampa, Fla., p. 161.
94. Ghetie. V. et al. (1988). J. Immunol. Methods 112, 267.
95. Jameson, et al. (1988). Science, 240:1335-1339.
96. Arthos, et al. (1989). Cell, 57:469-481.
97. Kalyanaraman, et al. (1990). J. AIDS, 6:119.
98. Till. et al. (1988). Science, 242:1166-1168.
99. Ghetie. et al. (1990). Bioconjugate Chem., 1:24.
100. Ibegbu, et al.(1989). J. Immunol., 142:2250-2256.
101. Ohnishi, et al.(1990). Can. Res., 50: 1107-1112.
102. Habeeb. A. F. (1980). Immunochemistry of Proteins, pp. 223. New York: Plenum Press.
103. Till, et al. (1989). Proc. Natl. Acad. Sci. (USA), 86:1987-1991.
104. Alakhov, et al. (1990). Biotech. appl. biochem., 12:94.
105. Kawasaki. N., et al. (1983). J. Biochem., 94:937-943.
106. Ezekowitz. R. A. B., et al. (1989). J. Exp. Med., 169:185-196
107. Brodsky, M. H., et al. (1990). J. Immunol., 144:3078-3086.
108. Wang, J., et al. (1990). Nature (London), 348:411-418.
109. Ryu, S-E., et al. (1990). Nature (London), 348:419-425.
110. Skinner. M. A., et al. (1988). J. Virol, 62:4195-4200.
111. Schnittman. S. M., et al. (1988). J. Immunol., 141:4181-4186.
112. Moore, J. P. (1990). AIDS, 4:297-305.
113. Moore, J. P., et al. (1990). AIDS, 4:307-315.
114. Callahan, L. N., et al. (1990) in: FASEB Meeting, New Orleans, Abstract #2015.

What is claimed is:

1. A composition of matter comprising a spacer and at least one gp120-binding peptide of from 17 to 50 amino acids conjugated to said spacer, wherein said peptide comprises amino acids 41-57 of CD4, wherein said composition reduces HIV binding to human cells in the presence of antibodies from an individual infected with HIV.

2. The composition of claim 1, wherein the gp120-binding peptide structure includes amino acids 41-84 of CD4.

3. The composition of claim 1, wherein the spacer comprises a serum soluble protein.

4. The composition of claim 3, wherein the protein spacer comprises OVA, BSA, HSA, poly-gly, or poly-ala.

5. The composition of claim 1, wherein the spacer comprises an N-hydroxysuccinimide ester.

6. The composition of claim 1, wherein the gp120-binding peptide includes from two to ten additional amino acids positioned at its carboxy terminus.

7. The composition of claim 1, wherein the gp120-binding peptide includes a carboxy terminal cysteine residue.

8. The composition of claim 3 or 5, wherein the gp120-binding peptide is conjugated to the spacer through a linker which includes a disulphide bond.

9. A pharmaceutical composition comprising a composition in accordance with claim 1, in combination with a pharmaceutically acceptable diluent.

10. A method for reducing the binding of HIV to human cells in the presence of antibodies of an individual infected with HIV, the method comprising:
   (a) preparing a composition of matter comprising a spacer and at least one gp120-binding peptide of from 17 to 50 amino acids conjugated to said spacer, wherein said peptide comprises amino acids 41–57 of CD4; and
   (b) contacting the human cells with said composition of matter in an amount effective to reduce the binding of HIV to said cells in the presence of such antibodies.

11. The method of claim 10, wherein the spacer comprises a serum soluble protein.

12. The method of claim 11, wherein the protein spacer comprises OVA, BSA, HSA, poly-gly, or poly-ala.

13. The method of claim 10, wherein the spacer comprises an N-hydroxysuccinimide ester.

14. The method of claim 10 or 11, wherein the gp120-binding peptide is not conjugated to a toxin molecule.

15. The method of claim 10, wherein step (b) comprises administering the gp120-binding peptide to an HIV infected individual.

16. The method of claim 10, wherein the gp120-binding peptide is one having the ability to reduce binding of HIV to human cells in the presence of antibodies to the CD4 protein.

17. The method of claim 10, wherein the gp120-binding peptide structure includes amino acids 41–84 of CD4.

* * * * *

UNITED STATES PATENT AND TRADEMARK OFFICE
CERTIFICATE OF CORRECTION

PATENT NO. : 5,767,072

DATED : June 16, 1998

INVENTOR(S) : ELLEN S. VITETTA and JONATHAN W. UHR

It is certified that error appears in the above-identified patent and that said Letters Patent is hereby corrected as shown below:

On page 2, title page, under OTHER PUBLICATIONS, immediately following the entry which begins "Studies are Exploring Potential of Soluble CD4 Therapy for HIV", insert the following:

-- Abstracts from the Third Annual Meeting of the NIH National Cooperative Drug Discovery Groups for the Treatment of AIDS; Washington, D.C., May 15-18, 1990.

Arnold et al., Abstracts from the Third Annual Meeting of the NIH National Cooperative Drug Discovery Groups for the Treatment of AIDS; Washington, D.C., May 15-18, 1990.

Arthos et al., Cell, 57:469-481, 1989.

Bates et al., Protein Engineering, 3(1):13-21, 1989.

Berger et al., PNAS, 86:9539-9543, 1989.

Bertonis et al., "Modern approaches to new vaccines, including prevention of AIDS, 9-13 September, 1987, Cold Spring Harbour, New York, p.42.

UNITED STATES PATENT AND TRADEMARK OFFICE
CERTIFICATE OF CORRECTION

PATENT NO. : 5,767,072

DATED : June 16, 1998

INVENTOR(S) : ELLEN S. VITETTA and JONATHAN W. UHR

It is certified that error appears in the above-identified patent and that said Letters Patent is hereby corrected as shown below:

Biddison and Shaw, *Immunol. Reviews*, 109:5-15, 1989.

Capon *et al.*, *Nature*, 337:525-530, 1989.

Chaudhary *et al.*, *Nature*, 335:369-372, 1988.

Clapham *et al.*, *Nature*, 337:368-370, 1989.

Deen *et al.*, *Nature*, 331:82-84, 1988.

Doyle and Strominger, *Nature*, 330:256-259, 1987.

Doyle *et al.*, *Immunol. Reviews*, 109:17-37, 1989.

Eiden *et al.*, Abstract from the Third Annual Meeting of the NIH National Cooperative Drug Discovery Groups for the Treatment of AIDS; Washington, D.C., May 15-18, 1990.

Fisher *et al.*, *Nature*, 317:76-79, 1988.

UNITED STATES PATENT AND TRADEMARK OFFICE
CERTIFICATE OF CORRECTION

PATENT NO.    :   5,767,072
DATED         :   June 16, 1998
INVENTOR(S)   :   ELLEN S. VITETTA and JONATHAN W. UHR It is certified that error appears in the above-identified patent and that said Letters Patent is hereby corrected as shown below:

Gay *et al.*, *Nature*, 238:626-629, 1987.

Ghetie *et al.*, *Bioconjugate Chemistry*, 1(1):24-31, 1990.

Ghetie *et al.*, *J. Immunol. Methods*, 126:135-141, 1990.

Hussey *et al.*, *Nature*, 331:78-81, 1988.

Ibegbu *et al.*, *J. Immunol.*, 142(7):2250-2256, 1989.

Jameson *et al.*, *Science*, 240:1335-1339, 1988.

Johnson *et al.*, *J. Infectious Diseases*, 159(5):837-844, 1989.

Lamarre *et al.*, *Science*, 245:743-746, 1989.

Landau *et al.*, *Nature*, 334:159-162, 1988.

UNITED STATES PATENT AND TRADEMARK OFFICE
CERTIFICATE OF CORRECTION

PATENT NO. : 5,767,072
DATED : June 16, 1998
INVENTOR(S) : ELLEN S. VITETTA and JONATHAN W. UHR It is certified that error appears in the above-identified patent and that said Letters Patent is hereby corrected as shown below:

Lasky et al., *Cell*, 50:975-985, 1987.

Lifson and Engleman, *Immunol. Reviews*, 109:94-117, 1989.

Lifson et al., *Nature*, 323:725-728, 1986.

Lifson et al., *Science*, 241:712-716, 1988.

Lui & Lui, *J. Clin. Invest.*, 82:2176-2180, 1988.

Matsushita et al., *AIDS Res. Hum. Retrovirus*, 6(2):193-204, 1990.

Palker et al., *J. Immunol.*, 142(10):3612-3619, 1989.

Peterson and Seed, *Cell*, 54:65-72, 1988.

Sattentau and Weiss, *Cell*, 52:631-633, 1988.

UNITED STATES PATENT AND TRADEMARK OFFICE
CERTIFICATE OF CORRECTION

PATENT NO. : 5,767,072

DATED : June 16, 1998

INVENTOR(S) : ELLEN S. VITETTA and JONATHAN W. UHR

It is certified that error appears in the above-identified patent and that said Letters Patent is hereby corrected as shown below:

Sattentau *et al.*, *J. Exp. Med.*, 170:1319-1334, 1989.

Schnittman *et al.*, *Science*, 245:743-746, 1989.

Sleckman *et al.*, *J. Immunol.*, 141(1):49-54, 1988.

Snyder *et al.*, Abstract from the Third Annual Meeting of the NIH National Cooperative Drug Discovery Groups for the Treatment of AIDS; Washington, D.C., May 15-18, 1990.

Sodroski *et al.*, *Nature*, 322:470-474, 1986.

Starich *et al.*, *Cell*, 45:637-648, 1986.

Till *et al.*, *J. Acquired Immune Deficiency Syndromes*, 3:609-614, 1990.

Traunecker *et al.*, *Nature*, 331:84-86, 1988.

Vitetta *et al.*, *Science*, 238:1098-1104, 1987.

UNITED STATES PATENT AND TRADEMARK OFFICE
CERTIFICATE OF CORRECTION

PATENT NO. : 5,767,072

DATED : June 16, 1998

INVENTOR(S) : ELLEN S. VITETTA and JONATHAN W. UHR

It is certified that error appears in the above-identified patent and that said Letters Patent is hereby corrected as shown below:

Watanabe et al., *Nature*, 337:267-270, 1989.

Weiss et al., *Biochem. Soc. Trans.*, 17:644-647, 1989.

Willey et al., *J. Virology*, 62(1):139-147, 1988.

Zarling et al., Abstract from the Third Annual Meeting of the NIH National Cooperative Drug Discovery Groups for the Treatment of AIDS; Washington, D.C., May 15-18, 1990. --

Signed and Sealed this

Fifth Day of January, 1999

Attest:

Attesting Officer

*Acting Commissioner of Patents and Trademarks*